United States Patent [19]
Fujita et al.

[11] Patent Number: 5,962,470
[45] Date of Patent: Oct. 5, 1999

[54] HETEROCYCLIC COMPOUNDS HAVING ANTI-DIABETIC ACTIVITY AND THEIR USE

[75] Inventors: Takashi Fujita; Takao Yoshioka; Toshihiko Fujiwara; Minoru Oguchi; Hiroaki Yanagisawa; Hiroyoshi Horikoshi; Kunio Wada; Koichi Fujimoto, all of Tokyo, Japan

[73] Assignee: Sankyo Company, Limited, Tokyo, Japan

[21] Appl. No.: 09/001,093

[22] Filed: Dec. 30, 1997

Related U.S. Application Data

[62] Division of application No. 08/713,543, Sep. 13, 1996, Pat. No. 5,834,501, which is a division of application No. 08/419,919, Apr. 11, 1995, Pat. No. 5,624,935.

[30] Foreign Application Priority Data

Apr. 11, 1994 [JP] Japan ........................ 6-72083

[51] Int. Cl.$^6$ ................ A61K 31/435; C07D 471/04
[52] U.S. Cl. .................. 514/303; 514/261; 514/266; 514/300; 546/113; 546/118; 546/121; 544/277
[58] Field of Search ............... 546/113, 118, 546/121; 544/277; 514/300, 303, 261, 266

[56] References Cited

U.S. PATENT DOCUMENTS

| 4,572,912 | 2/1986 | Yoshioka et al. | 514/369 |
|---|---|---|---|
| 4,691,027 | 9/1987 | Yoshioka et al. | 514/369 |
| 4,871,762 | 10/1989 | Yoshioka et al. | 514/369 |
| 4,873,225 | 10/1989 | Yoshioka et al. | 514/369 |
| 5,104,888 | 4/1992 | Yoshioka et al. | 514/369 |
| 5,143,930 | 9/1992 | Yoshioka et al. | 514/439 |
| 5,338,855 | 8/1994 | Yoshioka et al. | 514/369 |
| 5,387,596 | 2/1995 | Takebayashi et al. | 549/32 |

FOREIGN PATENT DOCUMENTS

| 0 008 203 | 2/1980 | European Pat. Off. |
| 0 139 421 | 5/1985 | European Pat. Off. |
| 0 177 353 | 4/1986 | European Pat. Off. |
| 0 208 420 | 1/1987 | European Pat. Off. |
| 0 306 228 | 3/1989 | European Pat. Off. |
| 0 356 214 | 2/1990 | European Pat. Off. |
| 0 441 605 | 8/1991 | European Pat. Off. |
| 0 528 734 | 2/1993 | European Pat. Off. |
| WO 91/07107 | 5/1991 | WIPO |
| WO 92/02520 | 2/1992 | WIPO |
| WO 92/03425 | 3/1992 | WIPO |
| WO 92/07839 | 5/1992 | WIPO |
| WO 92/07850 | 5/1992 | WIPO |

OTHER PUBLICATIONS

The Ring Index—2nd Edition, Austin Patterson et al (America Chemical Society), p. 157 (1960).

*Primary Examiner*—Bernard Dentz
*Attorney, Agent, or Firm*—Frishauf, Holtz, Goodman, Langer & Chick, P.C.

[57] ABSTRACT

Compounds of formula (I):

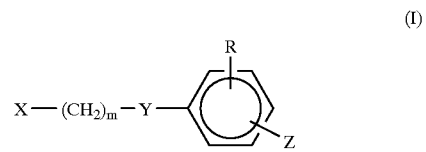

[wherein: X represents an unsubstituted or substituted indolyl, indolinyl, azaindolyl, azaindolinyl, imidazopyridyl or imidazopyrimidinyl group; Y represents an oxygen or sulfur atom; Z represents a 2,4-dioxo-thiazolidin-5-ylidenylmethyl, 2,4-dioxothiazolidin-5-ylmethyl, 2,4-dioxooxazolidin-5-ylmethyl, 3,5-dioxo-oxadiazolidin-2-ylmethyl or N-hydroxyureidomethyl group; R represents a hydrogen atom, an alkyl group, an alkoxy group, a halogen atom, a hydroxy group, a nitro group, an aralkyl group or a unsubstituted or substituted amino group; and m is an integer of from 1 to 5] have hypoglycemic and anti-diabetic activities.

30 Claims, No Drawings

HETEROCYCLIC COMPOUNDS HAVING ANTI-DIABETIC ACTIVITY AND THEIR USE

This is a division of application Ser. No. 08/713,543 filed Sep. 13, 1996, U.S. Pat. No. 5,834,501 which is a divisional application of Ser. No. 08/419,919 filed Apr. 11, 1995 now U.S. Pat. No. 5,624,935 issued Apr. 29, 1997.

BACKGROUND TO THE INVENTION

The present invention relates to a series of heterocyclic compounds having hypoglycemic and anti-diabetic activities, and provides processes for their preparation and methods and compositions for their use.

It is known that compounds which, like those of the present invention, contain, inter alia, a thiazolidinedione or oxazolidinedione group attached, via a methylene or methylidene group, to a benzene ring have this type of activity. Compounds of this general type are disclosed in European Patent Publications No. 008 203, 139 421, 441 605, 208 420, 528 734, 177 353, 306 228 and 356 214, and in WO 92/07850, 92/07839, 91/07107, 92/02520 and 92/03425. We have now discovered that the inclusion in such compounds of certain specific bicyclic nitrogen-containing ring systems results in compounds of much improved activity.

BRIEF SUMMARY OF INVENTION

Thus, it is an object of the present invention to provide a series of new chemical compounds which may be regarded as thiazolidine and oxazolidine derivatives or as ring-opened derivatives thereof.

It is a further, and more specific, object of the invention to provide such compounds, at least some of which may be useful for the treatment and/or prophylaxis of a variety of disorders, including one or more of: hyperlipemia, hyperglycemia, obesity, glucose tolerance insufficiency, insulin resistance and diabetic complications.

Other objects and advantages of the present invention will become apparent as the description proceeds.

Thus, the present invention provides compounds of formula (I):

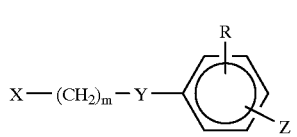

wherein:

X represents an indolyl, indolinyl, azaindolyl, azaindolinyl, imidazopyridyl or imidazopyrimidinyl group which is unsubstituted or is substituted by at least one substituent selected from the group consisting of substituents α, defined below;

Y represents an oxygen atom or a sulfur atom;

Z represents a group of formula (i), (ii), (iii), (iv) or (v):

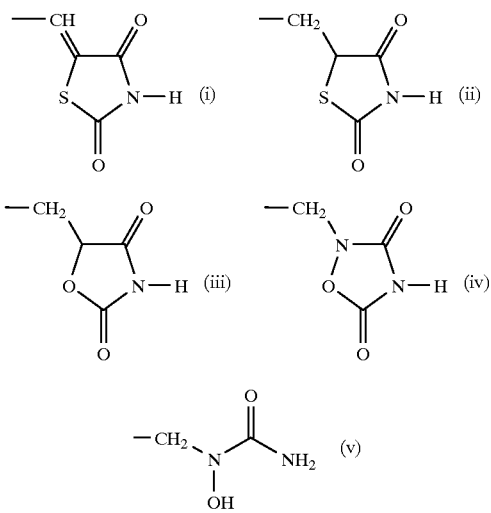

R represents a hydrogen atom, an alkyl group having from 1 to 4 carbon atoms, an alkoxy group having from 1 to 4 carbon atoms, a halogen atom, a hydroxy group, a nitro group, an aralkyl group in which an alkyl group having from 1 to 5 carbon atoms is substituted by an aryl group having from 6 to 10 ring carbon atoms, or a group of formula —NR$^a$R$^b$,
wherein R$^a$ and R$^b$ are the same or different and each represents a hydrogen atom, an alkyl group having from 1 to 8 carbon atoms, an aralkyl group in which an alkyl group having from 1 to 5 carbon atoms is substituted by an aryl group having from 6 to 10 ring carbon atoms, an aryl group having from 6 to 10 ring carbon atoms, an aliphatic carboxylic acyl group having from 1 to 11 carbon atoms, an aliphatic carboxylic acyl group which has from 2 to 6 carbon atoms and which is substituted by an aryl group having from 6 to 10 ring carbon atoms, or an aromatic carboxylic acyl group in which the aryl part has from 6 to 10 ring carbon atoms, m is an integer of from 1 to 5;

each of said substituents α represents an alkyl group having from 1 to 4 carbon atoms, an aryl group having from 6 to 10 carbon atoms, a trifluoromethyl group, an alkylthio group having from 1 to 4 carbon atoms, an alkoxy group having from 1 to 4 carbon atoms, a benzyloxy group, a halogen atom, a hydroxy group, an acetoxy group, a phenylthio group, a nitro group, an aralkyl group, or a group of formula —NR$^a$R$^b$, wherein R$^a$ and R$^b$ are as defined above;

said aryl groups and the aryl parts of said aralkyl groups included in substituents α are carbocyclic aromatic groups having from 6 to 10 ring carbon atoms and are unsubstituted or are substituted at least one substituent selected from the group consisting of substituents β, defined below;

each of said substituents β represents an alkyl group having from 1 to 4 carbon atoms, an alkoxy group having from 1 to 4 carbon atoms, a halogen atom, a hydroxy group, a nitro group, a phenyl group, a trifluoromethyl group, or a group of formula —NR$^a$R$^b$, wherein R$^a$ and R$^b$ are as defined above;

and salts thereof.

The invention also provides a pharmaceutical composition for the treatment or prophylaxis of diabetes or hyperlipemia and complications thereof, which composition comprises an effective amount of an active compound in admixture with a pharmaceutically acceptable carrier or diluent, wherein said active compound is selected from the group consisting of compounds of formula (I), defined above, and salts thereof.

The invention still further provides a method for the treatment or prophylaxis of diabetes or hyperlipemia and complications thereof in a mammal, which may be human, which method comprises administering to said mammal an effective amount of an active compound, wherein said active compound is selected from the group consisting of compounds of formula (I), defined above, and salts thereof.

The invention also provides processes for the preparation of the compounds of the present invention, which processes are described in more detail hereafter.

DETAILED DESCRIPTION OF INVENTION

In the compounds of the present invention, where X represents a group derived from an indole ring, it may be, for example, an indol-1-yl, indol-2-yl, indol-3-yl, indol-4-yl, indol-5-yl, indol-6-yl or indol-7-yl group.

Where X represents a group derived from an indoline ring, it may be, for example, an indolin-1-yl, indolin-2-yl, indolin-3-yl, indolin-4-yl, indolin-5-yl, indolin-6-yl or indolin-7-yl group.

Where X represents a group derived from an azaindole ring, it may be, for example, an 4-azaindol-1-yl, 4-azaindol-2-yl, 4-azaindol-3-yl, 4-azaindol-5-yl, 4-azaindol-6-yl, 4-azaindol-7-yl, 5-azaindol-1-yl, 5-azaindol-2-yl, 5-azaindol-3-yl, 5-azaindol-4-yl, 5-azaindol-6-yl, 5-azaindol-7-yl, 6-azaindol-1-yl, 6-azaindol-2-yl, 6-azaindol-3-yl, 6-azaindol-4-yl, 6-azaindol-5-yl, 6-azaindol-7-yl, 7-azaindol-1-yl, 7-azaindol-2-yl, 7-azaindol-3-yl, 7-azaindol-4-yl, 7-azaindol-5-yl or 7-azaindol-6-yl group.

Where X represents a group derived from an azaindoline ring, it may be, for example, an 4-azaindolin-1-yl, 4-azaindolin-2-yl, 4-azaindolin-3-yl, 4-azaindolin-5-yl-, 4-azaindolin-6-yl, 4-azaindolin-7-yl, 5-azaindolin-1-yl, 5-azaindolin-2-yl, 5-azaindolin-3-yl, 5-azaindolin-4-yl, 5-azaindolin-6-yl, 5-azaindolin-7-yl, 6-azaindolin-1-yl, 6-azaindolin-2-yl, 6-azaindolin-3-yl, 6-azaindolin-4-yl, 6-azaindolin-5-yl, 6-azaindolin-7-yl, 7-azaindolin-1-yl, 7-azaindolin-2-yl, 7-azaindolin-3-yl, 7-azaindolin-4-yl, 7-azaindolin-5-yl or 7-azaindolin-6-yl group.

Where X represents a group derived from an imidazopyridine ring, it may be, for example, an imidazo[4,5-b]pyridin-1-yl, imidazo[4,5-b]pyridin-2-yl, imidazo[4,5-b]pyridin-7-yl, imidazo[4,5-b]pyridin-5-yl, imidazo[4,5-b]pyridin-6-yl, imidazo[4,5-c]pyridin-1-yl, imidazo[4,5-c]pyridin-2-yl, imidazo[4,5-c]pyridin-4-yl, imidazo[4,5-c]pyridin-6-yl, imidazo[4,5-c]pyridin-7-yl, imidazo[5,4-b]pyridin-3-yl, imidazo[5,4-b]pyridin-2-yl, imidazo[5,4-b]pyridin-7-yl, imidazo[5,4-b]pyridin-5-yl, imidazo[5,4-b]pyridin-6-yl, imidazo[5,4-c]pyridin-3-yl, imidazo[5,4-c]pyridin-2-yl, imidazo[5,4-c]pyridin-4-yl, imidazo[5,4-c]pyridin-6-yl, imidazo[5,4-c]pyridin-7-yl, imidazo[1,2-a]pyridin-2-yl, imidazo[1,2-a]pyridin-3-yl, imidazo[1,2-a]pyridin-8-yl, imidazo[1,2-a]pyridin-5-yl, imidazo[1,2-a]pyridin-6-yl or imidazo[1,2-a]pyridin-7-yl group.

Where X represents a group derived from an imidazopyrimidine ring, it may be, for example, an imidazo-[4,5-d]pyrimidine-7-yl, imidazo[4,5-d]pyrimidine-8-yl or imidazo[4,5-d]pyrimidine-9-yl group.

Any of the above groups which may be represented by X may be unsubstituted or it may be substituted by at least one of substituents α, defined above and exemplified below. Where the group is substituted, there is no particular restriction on the number of substituents, except such as may be imposed by the number of substitutable positions, or, occasionally, by steric constraints. In general, however, from 1 to 3 substituents are preferred, 1 or 2 substituents being more preferred. There is also no particular restriction on the position of any such substituent.

Where R, substituent α or substituent β represents an alkyl group, this may be a straight or branched chain alkyl group having from 1 to 4 carbon atoms, and examples include the methyl, ethyl, propyl, isopropyl, butyl, isobutyl, sec-butyl and t-butyl groups, of which we prefer the methyl group.

Where R, substituent α or substituent β represents an alkoxy group, this may be a straight or branched chain alkoxy group having from 1 to 4 carbon atoms, and examples include the methoxy, ethoxy, propoxy, isopropoxy, butoxy, isobutoxy, sec-butoxy and t-butoxy groups, of which we prefer the methoxy group.

Where R, substituent α or substituent β represents a halogen atom, it may be, for example, a bromine, chlorine, fluorine or iodine atom, of which we prefer the bromine, chlorine and fluorine atoms, the chlorine atom being most preferred.

Where R represents an aralkyl group, the alkyl part of this group has from 1 to 5 carbon atoms and may be a straight or branched chain group which is substituted by an aryl group, which itself may be as defined above and exemplified below. In all, the aralkyl group preferably has from 7 to 11 carbon atoms. Examples of the alkyl part of such groups include the methyl, ethyl, propyl, isopropyl, butyl, isobutyl, sec-butyl, t-butyl, pentyl, isopentyl, neopentyl and t-pentyl groups (preferably the methyl and ethyl groups. Examples of aryl groups are given hereafter in relation to substituents α. Specific examples of such aralkyl groups include the benzyl, 2-phenylethyl (=phenethyl), 1-phenylethyl, 3-phenylpropyl, 2-phenylpropyl, 1-phenylpropyl, 4-phenylbutyl, 1-phenylbutyl, 5-phenylpentyl, 1-naphthylmethyl and 2-naphthylmethyl groups, of which the phenethyl and benzyl groups are preferred, the benzyl group being most preferred.

Alternatively, R, substituent α or substituent β may represent an amino group or substituted amino group of formula —NR$^a$R$^b$, where R$^a$ and R$^b$, which may be the same or different are selected from the following:

(1) Hydrogen atoms;

(2) Alkyl groups having from 1 to 8 carbon atoms, which may be straight or branched chain groups, for example the methyl, ethyl, propyl, isopropyl, butyl, isobutyl, sec-butyl, t-butyl, pentyl, 2-pentyl, 3-pentyl, 2-methylbutyl, 3-methylbutyl, 1,1-dimethylpropyl, 1,2-dimethylpropyl, 2,2-dimethylpropyl, hexyl, 2-hexyl, 3-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, heptyl, 2-heptyl, 3-heptyl, 4-heptyl, 3,3-dimethylpentyl, octyl, 1-methylheptyl, 2-ethylhexyl and 1,1,3,3-tetramethylbutyl groups, of which we prefer those straight and branched chain alkyl groups having from 1 to 6 carbon atoms, and most prefer those straight or branched chain alkyl groups having from 1 to 4 carbon atoms; the methyl and ethyl groups are most preferred;

(3) Aralkyl groups as defined and exemplified above in relation to the group which may be represented by R, and preferably such groups having from 7 to 11 carbon atoms;

(4) Aryl groups having from 6 to 10 carbon atoms, for example, the phenyl, 1-naphthyl and 2-naphthyl groups;

(5) Aliphatic carboxylic acyl groups, which may be straight or branched chain groups having from 1 to 11 carbon atoms, for example, the formyl, acetyl, propionyl, butyryl, isobutyryl, pivaloyl, pentanoyl, hexanoyl, heptanoyl, octanoyl, nonanoyl, decanoyl and undecanoyl groups;

(6) Aliphatic carboxylic acyl groups which have from 2 to 6 carbon atoms and which are substituted by an aryl group as defined above, and each of which preferably has a total of from 8 to 12 carbon atoms; examples of the aliphatic acyl part of the group are those acyl groups having from 2 to 6 carbon atoms which are included among the aliphatic acyl groups represented by $R^a$ and $R^b$ above (preferably the acetyl and propionyl groups), and examples of the aryl part are included among those aryl groups listed above (preferably the phenyl and naphthyl groups, especially the phenyl group); specific examples of preferred aromatic-substituted aliphatic acyl groups include the phenylacetyl, 3-phenylpropionyl, 4-phenylbutyryl, 5-phenylpentanoyl, 6-phenylhexanoyl, α-methylphenylacetyl and α,α-dimethylphenylacetyl groups, of which the phenylacetyl group is preferred;

(7) Carbocyclic aromatic carboxylic acyl groups, in which the aryl group is as defined and exemplified above (preferably the phenyl and naphthyl groups, especially the phenyl group); preferred groups are those having a total of from 7 to 11 carbon atoms, and examples include the benzoyl, 1-naphthoyl and 2-naphthoyl groups, of which the benzoyl group is preferred.

Specific examples of such amino groups which may be represented by R, substituent α or substituent β include the following:

(1) Substituted amino groups in which one of $R^a$ and $R^b$ represents a hydrogen atom and the other of $R^a$ and $R^b$ represents an alkyl group, such as the methylamino, ethylamino, propylamino, isopropylamino, butylamino, isobutylamino, sec-butylamino, t-butylamino, pentylamino, 2-pentylamino, 3-pentylamino, 2-methylbutylamino, 3-methylbutylamino, 1,1-dimethylpropylamino, 1,2-dimethylpropylamino, 2,2-dimethylpropylamino, hexylamino, 2-hexylamino, 3-hexylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1,1,2-trimethylpropylamino, 1,2,2-trimethylpropylamino, heptylamino, 2-heptylamino, 3-heptylamino, 4-heptylamino, 3,3-dimethylpentylamino, octylamino, 1-methylheptylamino, 2-ethylhexylamino and 1,1,3,3-tetramethylbutylamino groups;

(2) Substituted amino groups, in which one of $R^a$ and $R^b$ represents a hydrogen atom and the other of $R^a$ and $R^b$ represents an aralkyl group, such as the benzylamino, 2-phenylethylamino, 1-phenylethylamino, 3-phenylpropylamino, 2-phenylpropylamino, 1-phenylpropylamino, 4-phenylbutylamino, 1-phenylbutylamino, 5-phenylpentylamino, 1-naphthylmethylamino and 2-naphthylmethylamino groups;

(3) Substituted amino groups, in which one of $R^a$ and $R^b$ represents a hydrogen atom and the other of $R^a$ and $R^b$ represents an aryl group, such as the phenylamino, 1-naphthylamino and 2-naphthylamino groups;

(4) Substituted amino groups, in which one of $R^a$ and $R^b$ represents a hydrogen atom and the other of $R^a$ and $R^b$ represents an aliphatic acyl group, such as the formamido, acetamido, propionamido, butyramido, isobutyramido, pivaloylamino, pentanoylamino, hexanoylamino, heptanoylamino, octanoylamino, nonanoylamino, decanoylamino and undecanoylamino groups;

(5) Substituted amino groups, in which one of $R^a$ and $R^b$ represents a hydrogen atom and the other of $R^a$ and $R^b$ represents an aromatic-substituted aliphatic acyl group, such as the phenylacetamido, 3-phenylpropionamido, 4-phenylbutyramido, 5-phenylpentanoylamino, 6-phenylhexanoylamino, α-methylphenylacetamido and α,α-dimethylphenylacetamido groups;

(6) Substituted amino groups, in which one of $R^a$ and $R^b$ represents a hydrogen atom and the other of $R^a$ and $R^b$ represents an aromatic acyl group, such as the benzamido, 1-naphthoylamino and 2-naphthoylamino;

(7) Substituted amino groups, in which $R^a$ and $R^b$ both represent alkyl groups, which may be the same as or different from each other, such as the dimethylamino, diethylamino, N-methyl-N-ethylamino and N-methyl-N-pentylamino groups;

(8) Substituted amino groups, in which one of $R^a$ and $R^b$ represents an alkyl group and the other of $R^a$ and $R^b$ represents an aralkyl group, such as the N-ethyl-N-benzylamino, N-t-butyl-N-benzylamino and N-hexyl-N-benzylamino groups;

(9) Substituted amino groups, in which one of $R^a$ and $R^b$ represents an alkyl group and the other of $R^a$ and $R^b$ represents an aryl group, such as the N-methyl-N-phenylamino, N-ethyl-N-phenylamino and N-octyl-N-phenylamino groups;

(10) Substituted amino groups, in which one of $R^a$ and $R^b$ represents an alkyl group and the other of $R^a$ and $R^b$ represents an aliphatic acyl group, such as the N-propyl-N-acetylamino, N-pentyl-N-propionylamino and N-ethyl-N-hexanoylamino groups;

(11) Substituted amino groups, in which one of $R^a$ and $R^b$ represents an alkyl group and the other of $R^a$ and $R^b$ represents an aromatic-substituted carboxylic aliphatic acyl group, such as the N-ethyl-N-phenylacetylamino, N-isopropyl-N-(2-phenylpropionyl)amino and N-methyl-N-(6-phenylhexanoyl)amino groups;

(12) Substituted amino groups, in which one of $R^a$ and $R^b$ represents an alkyl group and the other of $R^a$ and $R^b$ represents an aromatic acyl group, such as the N-methyl-N-benzoylamino, N-sec-butyl-N-benzoylamino and N-heptyl-N-benzoylamino groups;

(13) Substituted amino groups, in which $R^a$ and $R^b$ both represent aralkyl groups, which may be the same as or different from each other, such as the dibenzylamino, N-benzyl-N-(3-phenylpropyl)amino and N-benzyl-N-(2-naphthylmethyl)amino groups;

(14) Substituted amino groups, in which one of $R^a$ and $R^b$ represents an aralkyl group and the other of $R^a$ and $R^b$ represents an aryl group, such as the N-benzyl-N-phenylamino and N-(3-phenylpropyl)-N-phenylamino groups;

(15) Substituted amino groups, in which one of $R^a$ and $R^b$ represents an aralkyl group and the other of $R^a$ and $R^b$ represents an aliphatic acyl group, such as the N-benzyl-N-acetylamino, N-benzyl-N-propionylamino and N-benzyl-N-pentanoylamino groups;

(16) Substituted amino groups, in which one of $R^a$ and $R^b$ represents an aralkyl group and the other of $R^a$ and $R^b$ represents an aromatic-substituted aliphatic carboxylic acyl group, such as the N-benzyl-N-phenylacetylamino and N-benzyl-N-(4-phenylbutyryl)amino groups;

(17) Substituted amino groups, in which one of $R^a$ and $R^b$ represents an aralkyl group and the other of $R^a$ and $R^b$ represents an aromatic acyl group, such as the N-benzyl-N-benzoylamino and N-(2-phenylethyl)-N-benzoylamino groups;

(18) Substituted amino groups, in which $R^a$ and $R^b$ both represent aryl groups, which may be the same as or different from each other, such as the diphenylamino, N-(1-naphthyl)-N-phenylamino and N-(2-naphthyl)-N-phenylamino groups;

(19) Substituted amino groups, in which one of $R^a$ and $R^b$ represents an aryl group and the other of $R^a$ and $R^b$ represents an aliphatic carboxylic acyl group, such as the N-phenyl-N-acetylamino, N-phenyl-N-propionylamino and N-phenyl-N-hexanoylamino groups;

(20) Substituted amino groups, in which one of $R^a$ and $R^b$ represents an aryl group and the other of $R^a$ and $R^b$ represents an aromatic-substituted aliphatic carboxylic acyl group, such as the N-phenyl-N-phenylacetylamino and N-phenyl-N-(4-phenylbutyryl)amino groups;

(21) Substituted amino groups, in which one of $R^a$ and $R^b$ represents an aryl group and the other of $R^a$ and $R^b$ represents an aromatic carboxylic acyl group, such as the N-phenyl-N-benzoylamino and N-phenyl-N-(2-naphthoyl)amino groups;

(22) Substituted amino groups, in which $R^a$ and $R^b$ both represent aliphatic carboxylic acyl groups, which may be the same as or different from each other, such as the N,N-diacetylamino, N-acetyl-N-propionylamino and N-butyryl-N-hexanoylamino groups;

(23) Substituted amino groups, in which one of $R^a$ and $R^b$ represents an aliphatic carboxylic acyl group and the other of $R^a$ and $R^b$ represents an aromatic-substituted aliphatic carboxylic acyl group, such as the N-acetyl-N-phenylacetylamino, N-acetyl-N-(4-phenylbutyryl)amino and N-butyryl-N-phenylacetylamino groups;

(24) Substituted amino groups, in which one of $R^a$ and $R^b$ represents an aliphatic carboxylic acyl group and the other of $R^a$ and $R^b$ represents an aromatic carboxylic acyl group, such as the N-acetyl-N-benzoylamino and N-butyryl-N-(2-naphthoyl)amino groups;

(25) Substituted amino groups, in which $R^a$ and $R^b$ both represent aromatic-substituted aliphatic carboxylic acyl groups, which may be the same as or different from each other, such as the N,N-diphenyl-acetylamino, N-phenylacetyl-N-(2-phenylpropionyl)-amino and N-phenylacetyl-N-(4-phenylbutyryl)amino groups;

(26) Substituted amino groups, in which one of $R^a$ and $R^b$ represents an aromatic-substituted aliphatic carboxylic acyl group and the other of $R^a$ and $R^b$ represents an aromatic carboxylic acyl group, such as the N-phenylacetyl-N-benzoylamino and N-phenylacetyl-N-(2-naphthoyl)amino groups; and

(27) Substituted amino groups, in which $R^a$ and $R^b$ both represent aromatic carboxylic acyl groups, which may be the same as or different from each other, such as the N,N-dibenzoylamino and N-benzoyl-N-(2-naphthoyl) amino groups.

Where substituent α represents an alkylthio group, this may be a straight or branched chain alkylthio group having from 1 to 4 carbon atoms, for example, the methylthio, ethylthio, propylthio, isopropylthio, butylthio, isobutylthio, sec-butylthio and t-butylthio groups.

Where substituent α represents an aryl group having from 6 to 10 carbon atoms, this group may be unsubstituted or may be substituted by at least one substituent selected from the group consisting of substituents β. Examples of the unsubstituted aryl groups include, for example, the phenyl, 1-naphthyl and 2-naphthyl groups.

Where substituent β represents an alkyl group having from 1 to 4 carbon atoms, an alkoxy group having from 1 to 4 carbon atoms, a halogen atom, a hydroxy, nitro, phenyl or trifluoromethyl group or an amino group of formula —NR$^a$R$^b$, the alkyl, alkoxy or amino group and the halogen atom may be as defined and exemplified above in relation to substituents α.

In the case of the substituted aryl groups, there is no particular restriction on the number of substituents β which may be present, the only restrictions being those imposed by the number of substitutable positions and possibly by steric constraints. In general, from 1 to 5 substituents are preferred, from 1 to 3 being more preferred and 1 or 2 being most preferred.

Examples of such substituted aryl groups include the following:

1) aryl groups substituted by at least one alkyl group having from 1 to 4 carbon atoms, such as the 4-methylphenyl, 4-ethylphenyl, 4-propylphenyl, 4-isopropylphenyl, 4-butylphenyl, 4-isobutylphenyl, 4-sec-butylphenyl, 4-t-butylphenyl, 4-methyl-1-naphthyl, 5-ethyl-1-naphthyl, 8-propyl-1-naphthyl, 4-isopropyl-1-naphthyl, 5-butyl-1-naphthyl, 4-isobutyl-1-naphthyl, 4-sec-butyl-1-naphthyl, 4-t-butyl-1-naphthyl, 4-methyl-2-naphthyl, 5-ethyl-2-naphthyl, 8-propyl-2-naphthyl, 4-isopropyl-2-naphthyl, 5-butyl-2-naphthyl, 8-isobutyl-2-naphthyl, 4-sec-butyl-2-naphthyl or 5-t-butyl-2-naphthyl groups;

2) aryl groups substituted by at least one alkoxy group having from 1 to 4 carbon atoms, such as the 4-methoxyphenyl, 4-ethoxyphenyl, 4-propoxyphenyl, 4-isopropoxyphenyl, 4-butoxyphenyl, 4-isobutoxyphenyl, 4-sec-butoxyphenyl, 4-t-butoxyphenyl, 4-methoxy-1-naphthyl, 5-ethoxy-1-naphthyl, 8-propoxy-1-naphthyl, 4-isopropoxy-1-naphthyl, 5-butoxy-1-naphthyl, 4-isobutoxy-1-naphthyl, 4-sec-butoxy-1-naphthyl, 4-t-butoxy-1-naphthyl, 4-methoxy-2-naphthyl, 5-ethoxy-2-naphthyl, 8-propoxy-2-naphthyl, 4-isopropoxy-2-naphthyl, 5-butoxy-2-naphthyl, 8-isobutoxy-2-naphthyl, 4-sec-butoxy-2-naphthyl or 5-t-butoxy-2-naphthyl groups;

3) aryl groups substituted by a halogen atom, such as the 4-bromophenyl, 4-chlorophenyl, 4-fluorophenyl, 4-iodophenyl, 3-chlorophenyl, 3-fluorophenyl, 3-bromophenyl, 3-iodophenyl, 4-bromo-1-naphthyl, 4-chloro-1-naphthyl, 4-fluoro-1-naphthyl, 4-iodo-1-naphthyl, 5-chloro-1-naphthyl, 5-fluoro-1-naphthyl, 5-bromo-1-naphthyl, 8-chloro-1-naphthyl, 4-fluoro-2-naphthyl, 4-bromo-2-naphthyl, 4-chloro-2-naphthyl, 4-iodo-2-naphthyl, 5-bromo-2-naphthyl, 5-chloro-2-naphthyl, 5-fluoro-2-naphthyl or 5-iodo-2-naphthyl groups;

4) aryl groups substituted by a hydroxy group, such as the 2-hydroxyphenyl, 3-hydroxyphenyl, 4-hydroxyphenyl, 4-hydroxy-1-naphthyl, 5-hydroxy-1-naphthyl, 8-hydroxy-1-naphthyl, 4-hydroxy-2-naphthyl, 5-hydroxy-2-naphthyl or 8-hydroxy-2-naphthyl groups;

5) aryl groups substituted by a nitro group, such as the 2-nitrophenyl, 3-nitrophenyl, 4-nitrophenyl, 4-nitro-1-naphthyl, 5-nitro-1-naphthyl, 8-nitro-1-naphthyl, 4-nitro-2-naphthyl, 5-nitro-2-naphthyl or 8-nitro-2-naphthyl groups;

6) aryl groups substituted by a phenyl group, such as the 3-phenylphenyl, 4-phenylphenyl, 4-phenyl-1-naphthyl, 5-phenyl-1-naphthyl, 8-phenyl-1-naphthyl, 4-phenyl-2-naphthyl, 5-phenyl-2-naphthyl or 8-phenyl-2-naphthyl groups;

7) aryl groups substituted by a trifluoromethyl group, such as the 3-trifluoromethylphenyl, 4-trifluoromethylphenyl, 4-trifluoromethyl-1-naphthyl, 5-trifluoromethyl-1-naphthyl, 8-trifluoromethyl-1-naphthyl, 4-trifluoromethyl-2-naphthyl, 5-trifluoromethyl-2-naphthyl or 8-trifluoromethyl-2-naphthyl groups;

8) aryl groups substituted by at least one unsubstituted or substituted amino group, such as those substituted by an unsubstituted amino group, for example the 2-aminophenyl, 3-aminophenyl, 4-aminophenyl, 4-amino-1-naphthyl and 8-amino-2-naphthyl groups and those substituted by a substituted amino group, for example:

i) aryl groups substituted by a substituted amino group in which one of $R^a$ and $R^b$ represents a hydrogen atom and the other of $R^a$ and $R^b$ represents an alkyl group, such as the 3-methylaminophenyl, 4-ethylaminophenyl, 3-propylaminophenyl, 3-isopropylaminophenyl, 4-butylaminophenyl or 3-isobutylaminophenyl groups;

ii) aryl groups substituted by a substituted amino group in which one of $R^a$ and $R^b$ represents a hydrogen atom and the other of $R^a$ and $R^b$ represents an aralkyl group, such as the 4-benzylaminophenyl, 4-(2-phenylethylamino)phenyl, 4-(1-phenylethylamino)phenyl, 4-(4-phenylbutylamino)phenyl or 4-(1-naphthylmethylamino)phenyl groups;

iii) aryl groups substituted by a substituted amino group in which one of $R^a$ and $R^b$ represents a hydrogen atom and the other of $R^a$ and $R^b$ represents an aryl group, such as the 4-phenyl-aminophenyl or 4-(1-naphthylamino)phenyl groups;

iv) aryl groups substituted by a substituted amino group in which one of $R^a$ and $R^b$ represents a hydrogen atom and the other of $R^a$ and $R^b$ represents an aliphatic acyl group, such as the 4-formamidophenyl, 4-acetamidophenyl, 4-butyramidophenyl, 4-pivaloylaminophenyl, 4-hexanoylaminophenyl, 4-octanoylaminophenyl or 4-undecanoylaminophenyl groups;

v) aryl groups substituted by a substituted amino group in which one of $R^a$ and $R^b$ represents a hydrogen atom and the other of $R^a$ and $R^b$ represents an aromatic-substituted aliphatic acyl group, such as the 4-phenylacetylaminophenyl, 4-(4-phenylbutyrylamino)phenyl, 4-(6-phenylhexanoylamino)phenyl, 4-(α-methylphenylacetylamino)phenyl or 4-(α,α-dimethylphenylacetylamino)phenyl groups;

vi) aryl groups substituted by a substituted amino group in which one of $R^a$ and $R^b$ represents a hydrogen atom and the other of $R^a$ and $R^b$ represents an aromatic acyl group, such as the 4-benzoylaminophenyl, 4-(1-naphthoylamino)phenyl or 4-(2-naphthoylamino)phenyl groups;

vii) aryl groups substituted by a substituted amino group in which $R^a$ and $R^b$ both represent alkyl groups, which may be the same as or different from each other, such as the 4-dimethylaminophenyl, 4-diethylaminophenyl or 4-(N-methyl-N-ethylamino)phenyl groups;

viii) aryl groups substituted by a substituted amino group in which one of $R^a$ and $R^b$ represents an alkyl group and the other of $R^a$ and $R^b$ represents an aralkyl group, such as the 4-(N-ethyl-N-benzylamino)phenyl, 4-(N-t-butyl-N-benzylamino)phenyl or 4-(N-hexyl-N-benzylamino)phenyl groups;

ix) aryl groups substituted by a substituted amino group in which one of $R^a$ and $R^b$ represents an alkyl group and the other of $R^a$ and $R^b$ represents an aryl group, such as the 4-(N-methyl-N-phenylamino)phenyl or 4-(N-octyl-N-phenylamino)phenyl groups;

x) aryl groups substituted by a substituted amino group in which one of $R^a$ and $R^b$ represents an alkyl group and the other of $R^a$ and $R^b$ represents an aliphatic acyl group, such as the 4-(N-propyl-N-acetylamino)phenyl or 4-(N-ethyl-N-hexanoylamino)phenyl groups;

xi) aryl groups substituted by a substituted amino group in which one of $R^a$ and $R^b$ represents an alkyl group and the other of $R^a$ and $R^b$ represents an aromatic-substituted aliphatic acyl group, such as the 4-(N-ethyl-N-phenylacetylamino)phenyl or 4-[N-methyl-N-(6-phenylhexanoyl)amino]phenyl groups;

xii) aryl groups substituted by a substituted amino group in which one of $R^a$ and $R^b$ represents an alkyl group and the other of $R^a$ and $R^b$ represents an aromatic acyl group, such as the 4-(N-methyl-N-benzoylamino)phenyl or 4-(N-heptyl-N-benzoylamino)phenyl groups;

xiii) aryl groups substituted by a substituted amino group in which $R^a$ and $R^b$ both represent aralkyl groups, which may be the same as or different from each other, such as the 4-dibenzyl-aminophenyl or 4-[N-benzyl-N-(2-naphthylmethyl)amino]phenyl groups;

xiv) aryl groups substituted by a substituted amino group in which one of $R^a$ and $R^b$ represents an aralkyl group and the other of $R^a$ and $R^b$ represents an aryl group, such as the 4-(N-benzyl-N-phenylamino)phenyl or 4-[N-(3-phenylpropyl)-N-phenylamino]phenyl groups;

xv) aryl groups substituted by a substituted amino group in which one of $R^a$ and $R^b$ represents an aralkyl group and the other of $R^a$ and $R^b$ represents an aliphatic acyl group, such as the 4-(N-benzyl-N-acetylamino)phenyl or 4-(N-benzyl-N-pentanoylamino)phenyl groups;

xvi) aryl groups substituted by a substituted amino group in which one of $R^a$ and $R^b$ represents an aralkyl group and the other of $R^a$ and $R^b$ represents an aromatic-substituted aliphatic acyl group, such as the 4-(N-benzyl-N-phenylacetylamino)phenyl or 4-[N-benzyl-N-(4-phenylbutyryl)amino]phenyl groups;

xvii) aryl groups substituted by a substituted amino group in which one of $R^a$ and $R^b$ represents an aralkyl group and the other of $R^a$ and $R^b$ represents an aromatic acyl group, such as the 4-(N-benzyl-N-benzoylamino)phenyl or 4-[N-(2-phenylethyl)-N-benzoylamino]phenyl groups;

xviii) aryl groups substituted by a substituted amino group in which $R^a$ and $R^b$ both represent aryl groups, which may be the same as or different from each other, such as the 4-diphenylaminophenyl or 4-[N-(2-naphthyl)-N-phenylamino]phenyl groups;

xix) aryl groups substituted by a substituted amino group in which one of $R^a$ and $R^b$ represents an aryl group and the other of $R^a$ and $R^b$ represents an aliphatic acyl group, such as the 4-(N-phenyl-N-acetylamino)phenyl or 4-(N-phenyl-N-hexanoylamino)phenyl groups;

xx) aryl groups substituted by a substituted amino group in which one of $R^a$ and $R^b$ represents an aryl group and the other of $R^a$ and $R^b$ represents an aromatic-substituted aliphatic acyl group, such as the 4-(N-phenyl-N-phenylacetylamino)-phenyl or 4-[N-phenyl-N-(4-phenylbutyryl)amino]-phenyl groups;

xxi) aryl groups substituted by a substituted amino group in which one of $R^a$ and $R^b$ represents an aryl group and the other of $R^a$ and $R^b$ represents an aromatic acyl group, such as the 4-(N-phenyl-N-benzoylamino)phenyl group;

xxii) aryl groups substituted by a substituted amino group in which $R^a$ and $R^b$ both represent aliphatic acyl groups, which may be the same as or different from each other, such as the 4-diacetyl-aminophenyl or 4-(N-butyryl-N-hexanoylamino)phenyl groups;

xxiii) aryl groups substituted by a substituted amino group in which one of $R^a$ and $R^b$ represents an aliphatic acyl group and the other of $R^a$ and $R^b$ represents an aromatic-substituted aliphatic acyl group, such as the 4-(N-acetyl-N-phenylacetylamino)phenyl or 4-(N-butyryl-N-phenylacetylamino)phenyl groups;

xxiv) aryl groups substituted by a substituted amino group in which one of $R^a$ and $R^b$ represents an aliphatic acyl group and the other of $R^a$ and $R^b$ represents an aromatic acyl group, such as the 4-(N-acetyl-N-benzoylamino)phenyl or 4-[N-butyryl-N-(2-naphthoyl)amino]phenyl groups;

xxv) aryl groups substituted by a substituted amino group in which $R^a$ and $R^b$ both represent aromatic-substituted aliphatic acyl groups, which may be the same as or different from each other, such as the 4-(N,N-diphenylacetylamino)phenyl or 4-[N-phenylacetyl-N-(4-phenylbutyryl)amino]phenyl groups;

xxvi) aryl groups substituted by a substituted amino group in which one of $R^a$ and $R^b$ represents an aromatic-substituted aliphatic acyl group and the other of $R^a$ and $R^b$ represents an aromatic acyl group, such as the 4-(N-phenylacetyl-N-benzoylamino) phenyl or 4-[N-phenylacetyl-N-(2-naphthoyl)amino] phenyl groups;

xxvii) aryl groups substituted by a substituted amino group in which $R^a$ and $R^b$ both represent aromatic acyl groups, which may be the same as or different from each other, such as the 4-dibenzoyl-aminophenyl or 4-[N-benzoyl-N-(2-naphthoyl) amino]-phenyl group.

Where substituent α represents an aralkyl group, this may be unsubstituted or it may be substituted by one or more of substituents β, defined and exemplified above. The group (excluding substituents, if any) preferably contains a total of from 7 to 11 carbon atoms. The alkyl part of the aralkyl group is an alkyl group having from 1 to 5 carbon atoms. Examples of such aralkyl groups include the benzyl, 2-phenylethyl, 1-phenylethyl, 3-phenylpropyl, 2-phenylpropyl, 1-phenylpropyl, 4-phenylbutyl, 1-phenylbutyl, 5-phenylpentyl, 1-naphthylmethyl and 2-naphthylmethyl groups.

In the case of the substituted aralkyl groups, there is no particular restriction on the number of substituents β which may be present, the only restrictions being those imposed by the number of substitutable positions and possibly by steric constraints. In general, from 1 to 5 substituents are preferred, from 1 to 3 being more preferred and 1 or 2 being most preferred.

Examples of such substituted aralkyl groups include the following:

1) aralkyl gruops substituted by at least one alkyl group having from 1 to 4 carbon atoms, such as the 4-methylbenzyl, 4-ethylbenzyl, 4-propylbenzyl, 4-isopropylbenzyl, 4-butylbenzyl, 4-isobutylbenzyl, 4-sec-butylbenzyl, 4-t-butylbenzyl, 4-methyl-1-naphthylmethyl, 5-ethyl-1-naphthylmethyl, 8-propyl-1-naphthylmethyl, 4-isopropyl-1-naphthylmethyl, 5-butyl-1-naphthylmethyl, 4-isobutyl-1-naphthylmethyl, 4-sec-butyl-1-naphthylmethyl, 4-t-butyl-1-naphthylmethyl, 4-methyl-2-naphthylmethyl, 5-ethyl-2-naphthylmethyl, 8-propyl-2-naphthylmethyl, 4-isopropyl-2-naphthylmethyl, 5-butyl-2-naphthylmethyl, 8-isobutyl-2-naphthylmethyl, 4-sec-butyl-2-naphthylmethyl or 5-t-butyl-2-naphthylmethyl groups;

2) aralkyl groups substituted by at least one alkoxy group having from 1 to 4 cabon atoms, such as the 4-methoxybenzyl, 4-ethoxybenzyl, 4-propoxybenzyl, 4-isopropoxybenzyl, 4-butoxybenzyl, 4-isobutoxybenzyl, 4-sec-butoxybenzyl, 4-t-butoxybenzyl, 4-methoxy-1-naphthylmethyl, 5-ethoxy-1-naphthylmethyl, 8-propoxy-1-naphthylmethyl, 4-isopropoxy-1-naphthylmethyl, 5-butoxy-1-naphthylmethyl, 4-isobutoxy-1-naphthylmethyl, 4-sec-butoxy-1-naphthylmethyl, 4-t-butoxy-1-naphthylmethyl, 4-methoxy-2-naphthylmethyl, 5-ethoxy-2-naphthylmethyl, 8-propoxy-2-naphthylmethyl, 4-isopropoxy-2-naphthylmethyl, 5-butoxy-2-naphthylmethyl, 8-isobutoxy-2-naphthylmethyl, 4-sec-butoxy-2-naphthylmethyl or 5-t-butoxy-2-naphthylmethyl groups;

3) aralkyl groups substituted by a halogen atom, such as the 4-bromobenzyl, 4-chlorobenzyl, 4-fluorobenzyl, 4-iodobenzyl, 3-chlorobenzyl, 3-fluorobenzyl, 3-bromobenzyl, 3-iodobenzyl, 4-bromo-1-naphthylmethyl, 4-chloro-1-naphthylmethyl, 4-fluoro-1-naphthylmethyl, 4-iodo-1-naphthylmethyl, 5-chloro-1-naphthylmethyl, 5-fluoro-1-naphthylmethyl, 5-bromo-1-naphthylmethyl, 8-chloro-1-naphthylmethyl, 4-fluoro-2-naphthylmethyl, 4-bromo-2-naphthylmethyl, 4-chloro-2-naphthylmethyl, 4-iodo-2-naphthylmethyl, 5-bromo-2-naphthylmethyl, 5-chloro-2-naphthylmethyl, 5-fluoro-2-naphthylmethyl or 5-iodo-2-naphthylmethyl groups;

4) aralkyl groups substituted by a hydroxy group, such as the 2-hydroxybenzyl, 3-hydroxybenzyl, 4-hydroxybenzyl, 4-hydroxy-1-naphthylmethyl, 5-hydroxy-1-naphthylmethyl, 8-hydroxy-1-naphthylmethyl, 4-hydroxy-2-naphthylmethyl, 5-hydroxy-2-naphthylmethyl or 8-hydroxy-2-naphthylmethyl groups;

5) aralkyl groups substituted by a nitro group, such as the 2-nitrobenzyl, 3-nitrobenzyl, 4-nitrobenzyl, 4-nitro-1-naphthylmethyl, 5-nitro-1-naphthylmethyl, 8-nitro-1- naphthylmethyl, 4-nitro-2-naphthylmethyl, 5-nitro-2-naphthylmethyl or 8-nitro-2-naphthylmethyl groups;
6) aralkyl groups substituted by a phenyl group, such as the 3-phenylbenzyl, 4-phenylbenzyl, 4-phenyl-1-naphthylmethyl, 5-phenyl-1-naphthylmethyl, 8-phenyl-1-naphthylmethyl, 4-phenyl-2-naphthylmethyl, 5-phenyl-2-naphthylmethyl or 8-phenyl-2-naphthylmethyl groups;
7) aralkyl groups substituted by a trifluoromethyl group, such as the 3-trifluoromethylbenzyl, 4-trifluoromethylbenzyl, 4-trifluoromethyl-1-naphthylmethyl, 5-trifluoromethyl-1-naphthylmethyl, 8-trifluoromethyl-1-naphthylmethyl, 4-trifluoromethyl-2-naphthylmethyl, 5-trifluoromethyl-2-naphthylmethyl or 8-trifluoromethyl- 2-naphthylmethyl groups;
8) aralkyl groups substituted by at least one unsubstituted or substituted amino group, such as those substituted by an unsubstituted amino group, for example the 2-aminobenzyl, 3-aminobenzyl, 4-aminobenzyl, 4-amino-1-naphthylmethyl or 8-amino-2-naphthylmethyl groups and those-substituted by a substituted amino group, for example:
  i) aralkyl groups substituted by a substituted amino group in which one of $R^a$ and $R^b$ represents a hydrogen atom and the other of $R^a$ and $R^b$ represents an alkyl group, such as the 3-methylaminobenzyl, 4-ethylaminobenzyl, 3-propylaminobenzyl, 3-isopropylaminobenzyl, 4-butylaminobenzyl or 3-isobutylaminobenzyl groups;
  ii) aralkyl groups substituted by a substituted amino group in which one of $R^a$ and $R^b$ represents a hydrogen atom and the other of $R^a$ and $R^b$ represents an aralkyl group, such as the 4-benzylaminobenzyl, 4-(2-phenylethylamino)benzyl, 4-(1-phenylethylamino)benzyl, 4-(4-phenylbutylamino)benzyl or 4-(1-naphthylmethylamino)benzyl groups;
  iii) aralkyl groups substituted by a substituted amino group in which one of $R^a$ and $R^b$ represents a hydrogen atom and the other of $R^a$ and $R^b$ represents an aryl group, such as the 4-phenylaminobenzyl or 4-(1-naphthylamino)benzyl groups;
  iv) aralkyl groups substituted by a substituted amino group in which one of $R^a$ and $R^b$ represents a hydrogen atom and the other of $R^a$ and $R^b$ represents an aliphatic acyl group, such as the 4-formamidobenzyl, 4-acetamidobenzyl, 4-butyramidobenzyl, 4-pivaloylaminobenzyl, 4-hexanoylaminobenzyl, 4-octanoylaminobenzyl or 4-undecanoylaminobenzyl groups;
  v) aralkyl groups substituted by a substituted amino group in which one of $R^a$ and $R^b$ represents a hydrogen atom and the other of $R^a$ and $R^b$ represents an aromatic-substituted aliphatic acyl group, such as the 4-phenylacetamidobenzyl, 4-(4-phenylbutyrylamino)benzyl, 4-(6-phenylhexanoylamino)benzyl, 4-($\alpha$-methylphenylacetylamido)benzyl or 4-($\alpha,\alpha$-dimethylphenylacetamido)benzyl groups;
  vi) aralkyl groups substituted by a substituted amino group in which one of $R^a$ and $R^b$ represents a hydrogen atom and the other of $R^a$ and $R^b$ represents an aromatic acyl group, such as the 4-benzoylaminobenzyl, 4-(1-naphthoylamino)benzyl or 4-(2-naphthoylamino)benzyl groups;
  vii) aralkyl groups substituted by a substituted amino group in which $R^a$ and $R^b$ both represent alkyl groups, which may be the same as or different from each other, such as the 4-dimethylaminobenzyl, 4-diethylaminobenzyl or 4-(N-methyl-N-ethylamino)benzyl groups;
  viii) aralkyl groups substituted by a substituted amino group in which one of $R^a$ and $R^b$ represents an alkyl group and the other of $R^a$ and $R^b$ represents an aralkyl group, such as the 4-(N-ethyl-N-benzylamino)benzyl, 4-(N-t-butyl-N-benzylamino) benzyl or 4-(N-hexyl-N-benzylamino)benzyl groups;
  ix) aralkyl groups substituted by a substituted amino group in which one of $R^a$ and $R^b$ represents an alkyl group and the other of $R^a$ and $R^b$ represents an aryl group, such as the 4-(N-methyl-N-phenylamino) benzyl or 4-(N-octyl-N-phenylamino)benzyl groups;
  x) aralkyl groups substituted by a substituted amino group in which one of $R^a$ and $R^b$ represents an alkyl group and the other of $R^a$ and $R^b$ represents an aliphatic acyl group, such as the 4-(N-propyl-N-acetylamino)benzyl or 4-(N-ethyl-N-hexanoylamino)benzyl groups;
  xi) aralkyl groups substituted by a substituted amino group in which one of $R^a$ and $R^b$ represents an alkyl group and the other of $R^a$ and $R^b$ represents an aromatic-substituted aliphatic acyl group, such as the 4-(N-ethyl-N-phenylacetylamino)benzyl or 4-[N-methyl-N-(6-phenylhexanoyl)amino]-benzyl groups;
  xii) aralkyl groups substituted by a substituted amino group in which one of $R^a$ and $R^b$ represents an alkyl group and the other of $R^a$ and $R^b$ represents an aromatic acyl group, such as the 4-(N-methyl-N-benzoylamino)benzyl or 4-(N-heptyl-N-benzoylamino)benzyl groups;
  xiii) aralkyl groups substituted by a substituted amino group in which $R^a$ and $R^b$ both represent aralkyl groups, which may be the same as or different from each other, such as the 4-dibenzylaminobenzyl or 4-[N-benzyl-N-(2-naphthylmethyl)amino]benzyl groups;
  xiv) aralkyl groups substituted by a substituted amino group in which one of $R^a$ and $R^b$ represents an aralkyl group and the other of $R^a$ and $R^b$ represents an aryl group, such as the 4-(N-benzyl-N-phenylamino)benzyl or 4-[N-(3-phenylpropyl)-N-phenylamino]benzyl groups;
  xv) aralkyl groups substituted by a substituted amino group in which one of $R^a$ and $R^b$ represents an aralkyl group and the other of $R^a$ and $R^b$ represents an aliphatic acyl group, such as the 4-(N-benzyl-N-acetylamino)benzyl or 4-(N-benzyl-N-pentanoylamino)benzyl groups;
  xvi) aralkyl groups substituted by a substituted amino group in which one of $R^a$ and $R^b$ represents an aralkyl group and the other of $R^a$ and $R^b$ represents an aromatic-substituted aliphatic acyl group, such as the 4-(N-benzyl-N-phenylacetylamino)benzyl or 4-[N-benzyl-N-(4-phenylbutyryl)amino]benzyl groups;
  xvii) aralkyl groups substituted by a substituted amino group in which one of $R^a$ and $R^b$ represents aralkyl group and the other of $R^a$ and $R^b$ represents an aromatic acyl group, such as the 4-(N-benzyl-N-benzoylamino)benzyl or 4-[N-(2-phenylethyl)-N-benzoylaminolbenzyl groups;
  xviii) aralkyl groups substituted by a substituted amino group in which $R^a$ and $R^b$ both represent aryl groups, which may be the same as or different from each other, such as the 4-diphenylaminobenzyl or 4-[N-(2-naphthyl)-N-phenylamino]benzyl groups;

xix) aralkyl groups substituted by a substituted amino group in which one of $R^a$ and $R^b$ represents an aryl group and the other of $R^a$ and $R^b$ represents an aliphatic acyl group, such as the 4-(N-phenyl-N-acetylamino)benzyl or 4-(N-phenyl-N-hexanoylamino)benzyl groups;

xx) aralkyl groups substituted by a substituted amino group in which one of $R^a$ and $R^b$ represents an aryl group and the other of $R^a$ and $R^b$ represents an aromatic-substituted aliphatic acyl group, such as the 4-(N-phenyl-N-phenylacetylamino)benzyl or 4-[N-phenyl-N-(4-phenylbutyryl)amino]benzyl groups;

xxi) aralkyl groups substituted by a substituted amino group in which one of $R^a$ and $R^b$ represents an aryl group and the other of $R^a$ and $R^b$ represents an aromatic acyl group, such as the 4-(N-phenyl-N-benzoylamino)benzyl groups;

xxii) aralkyl groups substituted by a substituted amino group in which $R^a$ and $R^b$ both represent aliphatic acyl groups, which may be the same as or different from each other, such as the 4-diacetyl-aminobenzyl or 4-(N-butyryl-N-hexanoylamino)benzyl groups;

xxiii) aralkyl groups substituted by a substituted amino group in which one of $R^a$ and $R^b$ represents an aliphatic acyl group and the other of $R^a$ and $R^b$ represents an aromatic-substituted aliphatic acyl group, such as the 4-(N-acetyl-N-phenylacetylamino)benzyl or 4-(N-butyryl-N-phenylacetylamino)benzyl groups;

xxiv) aralkyl groups substituted by a substituted amino group in which one of $R^a$ and $R^b$ represents an aliphatic acyl group and the other of $R^a$ and $R^b$ represents an aromatic acyl group, such as the 4-(N-acetyl-N-benzoylamino)benzyl or 4-[N-butyryl-N-(2-naphthoyl)amino]benzyl groups;

xxv) aralkyl groups substituted by a substituted amino group in which $R^a$ and $R^b$ both represent aromatic-substituted aliphatic acyl groups, which may be the same as or different from each other, such as the 4-(N,N-diphenylacetylamino)benzyl or 4-[N-phenylacetyl-N-(4-phenylbutyryl)amino]benzyl groups;

xxvi) aralkyl groups substituted by a substituted amino group in which one of $R^a$ and $R^b$ represents an aromatic-substituted aliphatic acyl group and the other of $R^a$ and $R^b$ represents an aromatic acyl group, such as the 4-(N-phenylacetyl-N-benzoylamino) benzyl or 4-[N-phenylacetyl-N-(2-naphthoyl)amino] benzyl groups;

xxvii) aralkyl groups substituted by a substituted amino group in which $R^a$ and $R^b$ both represent aromatic acyl groups, which may be the same as or different from each other, such as the 4-dibenzoylaminobenzyl or 4-[N-benzoyl-N-(2-naphthoyl)amino]benzyl groups.

Specific examples of substituted groups derived from the indole, indoline, azaindole, azaindoline, imidazopyridine and imidazopyrimidine rings, each of which is substituted, preferably by from 1 to 3 of substituents α, which may be represented by X, include, for example:

indole ring groups, such as the
3-triphenylmethylindol-1-yl, 1-methylindol-3-yl, 1-methylindol-2-yl, 1-ethylindol-2-yl, 5-methoxy-1,2-dimethylindol-3-yl, 5-hydroxy-1-methylindol-3-yl, 1-isopropylindol-3-yl, 2-ethyl-1-methylindol-3-yl, 5-methoxy-1-methylindol-3-yl, 5-hydroxy-1,2-dimethylindol--3-yl, 5-butoxy-1-methylindol-3-yl, 1,4,7-trimethylindol-3-yl, 1,6-dimethylindol-3-yl, 5-bromo-6-chloro-1-methylindol-3-yl, 5-bromoindol-3-yl, 5-hydroxy-1-isobutylindol-3-yl, 5-fluoro-1-methylindol-2-yl, 5-chloro-1-methylindol-2-yl, 5-hydroxy-1-methylindol-2-yl, 5-methoxy-1-methylindol-2-yl, 5-bromo-1-methylindol-2-yl, 1-ethyl-5-nitroindol-2-yl, 1,5-dimethylindol-2-yl, 5-amino-1-methylindol-2-yl, 5-acetamido-1-methylindol-2-yl, 5-benzamido-1-ethylindol-2-yl, 1-methyl-5-methyl-aminoindol-2-yl, 5-butylamino-1-methylindol-2-yl, 5-(N-benzoyl-N-methylamino)-1-methylindol-2-yl, 1-methyl-5-phenylaminoindol-2-yl, 5-acetamidoindol-2-yl, 5-benzamido-1-butylindol-2-yl, 4-chloro-1-methylindol-2-yl, 3-methoxy-1-methylindol-2-yl, 6-fluoro-1-methylindol-2-yl, 6-chloro-1-ethylindol-2-yl, 6-methoxy-1-methylindol-2-yl, 5,6-dimethoxy-1-methylindol-2-yl, 7-methoxyindol-2-yl, 1-methylindol-5-yl, 1-butylindol-5-yl, 1-ethylindol-5-yl, 1-methylindol-4-yl, 1-isopropylindol-4-yl and 1-butylindol-4-yl groups;

indoline ring groups, such as the
5-methoxyindolin-1-yl, 1-methylindolin-2-yl, 1-ethylindolin-2-yl, 1-propylindolin-2-yl, 1-butylindolin-2-yl and 1-isopropylindolin-2-yl groups;

azaindole ring groups, such as the
1-methyl-7-azaindol-3-yl, 1-isopropyl-7-azaindol-3-yl, 1-methyl-7-azaindol-2-yl and 1-methyl-6-azaindol-2-yl groups;

azaindoline ring groups, such as the
1-methyl-7-azaindolin-2-yl, 1-ethyl-7-azaindolin-2-yl, 1-isopropyl-7-azaindolin-2-yl and 1-butyl-7-azaindolin-2-yl groups;

imidazopyridine ring groups, such as the
7-methylimidazo[4,5-b]pyridin-2-yl, 1-butylimidazo-[4,5-b]pyridin-2-yl, 1-methylimidazo[4,5-b]pyridin-2-yl, 1-propylimidazo[4,5-b]pyridin-2-yl, 5-chloro-1-methylimidazo[4,5-b]pyridin-2-yl, 5-methoxy-1-methylimidazo[4,5-b]pyridin-2-yl, 6,8-dibromoimidazo[1,2-a]pyridin-2-yl, 8-hydroxyimidazo-[1,2-a]pyridin-2-yl, 6-chloroimidazo[1,2-a]-pyridin-2-yl, 2-methylimidazo[1,2-a]pyridin-7-yl, 2-ethylimidazo[1,2-a]pyridin-8-yl, 3-methylimidazo-[5,4-b]pyridin-2-yl, 3-ethylimidazo[5,4-b]pyridin-2-yl, 3,7-dimethylimidazo[5,4-b]pyridin-2-yl, 5-chloro-3-methylimidazo[5,4-b]pyridin-2-yl, 5-chloro-3-phenylimidazo[5,4-b]pyridin-2-yl, 5-bromo-3-methylimidazo[5,4-b]pyridin-2-yl, 3-methyl-6-trifluoromethylimidazo[5,4-b]pyridin-2-yl, 3-isopropyl-6-trifluoromethylimidazo[5,4-b]pyridin-2-yl, 3-(3-chlorobenzyl)imidazo[5,4-b]pyridin-2-yl, 3-benzylimidazo[5,4-b]pyridin-2-yl, 3-(4-chlorobenzyl)imidazo[5,4-b]pyridin-2-yl, 3-(4-phenylbenzyl)imidazo[5,4-b]pyridin-2-yl, 6-bromo-3-methylimidazo[5,4-b]pyridin-2-yl, 6-bromo-3-ethylimidazo[5,4-b]pyridin-2-yl, 6-bromo-3-phenylimidazo[5,4-b]pyridin-2-yl, 6-chloro-3-methylimidazo[5,4-b]pyridin-2-yl, 3-butyl-6-chloroimidazo[5,4-b]pyridin-2-yl, 5-methoxy-3-methylimidazo[5,4-b]pyridin-2-yl, 3-ethyl-5-methoxyimidazo[5,4-b]pyridin-2-yl, 5-methoxy-3-propylimidazo[5,4-b]pyridin-2-yl, 5-methoxy-3-phenylimidazo[5,4-b]pyridin-2-yl, 3-benzyl-5-methoxyimidazo[5,4-b]pyridin-2-yl, 3-(3- chlorophenyl)-5-methoxyimidazo[5,4-b]pyridin-2-yl, 5-hydroxy-3-methylimidazo[5,4-b]pyridin-2-yl, 3-ethyl-5-hydroxyimidazo[5,4-b]pyridin-2-yl, 3-benzyl-5-hydroxyimidazo[5,4-b]pyridin-2-yl, 3-phenylimidazo[5,4-b]pyridin-2-yl, 3-(4-chlorophenyl)imidazo[5,4-b]pyridin-2-yl, 3-(3-chlorophenyl)imidazo[5,4-b]pyridin-2-yl, 3-(2-methylphenyl)imidazo[5,4-b]pyridin-2-yl, 5-chloro-3-(3-chlorophenyl)imidazo[5,4-b]pyridin-2-yl, 5-methoxy-3-(3-methoxyphenyl)-imidazo[5,4-b]pyridin-2-yl, 5-hydroxy-3,6-dimethylimidazo[5,4-b]pyridin-2-yl, 5-methoxy-3,6-dimethylimidazo[5,4-b]pyridin-2-yl, 3-methylimidazo[5,4-b]pyridin-5-yl, 2,3-dimethylimidazo[5,4-b]pyridin-5-yl, 3-ethyl-2-methylimidazo[5,4-b]pyridin-5-yl, 3-methyl-2-phenylimidazo[5,4-b]pyridin-5-yl, 2-[2-(3,5-di-t-butyl-4-hydroxyphenyl)ethyl]-3-methylimidazo[5,4-b]pyridin-5-yl, 2-(3-chlorophenyl)-3-methylimidazo[5,4-b]pyridin-5-yl, 3-methyl-5-phenylthioimidazo[5,4-b]pyridin-2-yl, 5-butylthio-3-methylimidazo[5,4-b]pyridin-2-yl, 3-methyl-5-phenylimidazo[5,4-b]pyridin-2-yl, 5-(3,5-di-t-butyl-4-hydroxyphenylthio)-3-methylimidazo[5,4-b]-pyridin-2-yl, 5-ethoxy-3-methylimidazo[5,4-b]pyridin-2-yl, 5-isopropoxy-3-methylimidazo[5,4-b]pyridin-2-yl, 5-acetoxy-3-methylimidazo[5,4-b]pyridin-2-yl, 3-ethyl-5-phenoxy-6-trifluoromethylimidazo[5,4-b]pyridin-2-yl, 7-chloro-3-methylimidazo[5,4-b]pyridin-2-yl, 7-chloro-3-propylimidazo[5,4-b]pyridin-2-yl, 6-hydroxy-3,5,7-trimethylimidazo[5,4-b]pyridin-2-yl, 3,5,7-trimethyl-6-nitroimidazo[5,4-b]pyridin-2-yl, 6-amino-3,5,7-trimethylimidazo[5,4-b]pyridin-2-yl, 3-methyl-5-methylaminoimidazo[5,4-b]pyridin-2-yl, 5-dimethylamino-3-methylimidazo[5,4-b]pyridin-2-yl, 5-(N-butyl-N-ethylamino)-3-methylimidazo[5,4-b]pyridin-2-yl, 3-methyl-5-phenylaminoimidazo[5,4-b]pyridin-2-yl, 5-benzylamino-3-methylimidazo[5,4-b]pyridin-2-yl, 5-(N-ethyl-N-phenylamino)-3-methylimidazo[5,4-b]pyridin-2-yl, 5-acetamido-3-methylimidazo[5,4-b]pyridin-2-yl, 5-benzoylamino-3-methylimidazo[5,4-b]pyridin-2-yl, 3-methyl-6-nitroimidazo[5,4-b]pyridin-2-yl, 6-amino-3-methylimidazo[5,4-b]pyridin-2-yl, 6-benzoylamino-3-methylimidazo[5,4-b]pyridin-2-yl, 6-valeryl-3-butylimidazo[5,4-b]pyridin-2-yl, 5-benzyloxy-3-methylimidazo[5,4-b]pyridin-2-yl, 2-hydroxy-3-methylimidazo[5,4-b]pyridin-5-yl, 2-hydroxy-3H-imidazo[5,4-b]pyridin-5-yl, 2-hydroxy-3-phenylimidazo[5,4-b]pyridin-5-yl, 2-methylthio-3H-imidazo[5,4-b]pyridin-5-yl, 3-methyl-2-methylthioimidazo[5,4-b]pyridin-5-yl, 3-benzyl-2-butylthioimidazo[5,4-b]pyridin-5-yl, 5-t-butylamino-3-methylimidazo[5,4-b]pyridin-2-yl, 5-t-butylamino-3-propylimidazo[5,4-b]pyridin-2-yl, 3,5,7-trimethylimidazo[5,4-b]pyridin-2-yl, 3-(3-chlorophenyl)-5,7-dimethylimidazo[5,4-b]pyridin-2-yl, 3-(3,5-di-t-butyl-4-hydroxybenzyl)-5,7-dimethylimidazo[5,4-b]pyridin-2-yl, 5-acetoxy-3-methylimidazo[5,4-b]pyridin-2-yl, 5-acetoxy-3-ethylimidazo[5,4-b]pyridin-2-yl, 6-methoxy-3-methylimidazo[5,4-c]pyridin-2-yl, 1-methylimidazo[4,5-c]pyridin-2-yl, 1-butylimidazo[4,5-c]pyridin-2-yl groups;

imidazopyrimidine ring groups, such as the 3-methylimidazo[5,4-d]pyrimidin-2-yl, 3-ethylimidazo[5,4-d]pyrimidin-2-yl and 3-(3-methylbenzyl)imidazo 5,4-d]pyrimidin-2-yl groups.

Of the compounds of the present invention, we prefer those compounds of formula (I) and s alts thereof, in which:

(A1) X represents an indolyl, indolinyl, azaindolyl, imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, provided that, if R$^a$ or R$^b$ represents an aryl group or represents a group including an aryl group, that aryl group is not itself further substituted by a group of formula —NR$^a$R$^b$;

or an aralkyl group having from 7 to 11 carbon atoms which is unsubstituted or is substituted by at least one substituent selected from the group consisting of substituents β; and/or (A2) Y represents an oxygen or sulfur atom; and/or (A3) Z represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethyl group; and/or (A4) R represents a hydrogen atom, an alkyl group having from 1 to 4 carbon atoms, an alkoxy group having from 1 to 4 carbon atoms or a halogen atom; and/or (A5) m is an integer of from 1 to 5;

and especially compounds in which X is as defined in (A1), Y is as defined in (A2), Z is as defined in (A3), R is as defined in (A4) and m is as defined in (A5).

More preferred compounds of the present invention are those compounds of formula (I) and salts thereof, in which:

(B1) X represents an indolyl, indolinyl, imidazopyridyl or imidazopyrimidinyl group, which is unsubstituted or is substituted by from 1 to 3 of substituents α, defined below;

substituent a represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by at least one substituent selected from the group consisting of substituents β; and/or (B2) Y represents an oxygen atom; and/or (B3) Z represents a 2,4-dioxothiazolidin-5-ylidenylmethyl, 2,4-dioxothiazolidin-5-ylmethyl or 2,4,-dioxooxazolidin-5-ylmethyl group; and/or (B4) R represents a hydrogen atom, an alkyl group having from 1 to 4 carbon atoms, an alkoxy group having from 1 to 4 carbon atoms or a halogen atom; and/or (B5) m is an integer of from 1 to 5;

and especially compounds in which X is as defined in (B1), Y is as defined in (B2), Z is as defined in (B3), R is as defined in (B4) and m is as defined in (B5).

Still more preferred compounds of the present invention are those compounds of formula (I) and salts thereof, in which:

(C1) X represents an indolyl, indolinyl or imidazopyridyl group, which is unsubstituted or is substituted by from 1 to 3 of substituents a, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by from 1 to 3 substituents selected from the group consisting of substituents β; and/or (C2) Y represents an oxygen atom; and/or (C3) Z represents a 2,4-dioxothiazolidin-5-ylidenylmethyl or 2,4-dioxothiazolidin-5-ylmethyl group; and/or (C4) R represents a hydrogen atom, a methoxy group, an ethoxy group, a fluorine atom or a chlorine atom; and/or (C5) m is an integer of from 1 to 5;

and especially compounds in which X is as defined in (C1), Y is as defined in (C2), Z is as defined in (C3), R is as defined in (C4) and m is as defined in (C5).

Still more preferred compounds of the present invention are those compounds of formula (I) and salts thereof, in which:

(D1) X represents an indolinyl or imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group or a phenyl group; and/or (D2) Y represents an oxygen atom; and/or (D3) Z represents a 2,4-dioxothiazolidin-5-ylmethyl group; and/or (D4) R represents a hydrogen atom or a methoxy group; and/or (D5) m is an integer of from 1 to 5;

and especially compounds in which X is as defined in (D1), Y is as defined in (D2), Z is as defined in (D3), R is as defined in (D4) and m is as defined in (D5).

The most preferred compounds of the present invention are those compounds of formula (I) and salts thereof, in which:

(E1) X represents an imidazopyridyl group, which is unsubstituted or is substituted by from 1 to 3 of substituents α, defined below;

substituent α represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group or a phenyl group; and/or (E2) Y represents an oxygen atom; and/or (E3) Z represents a 2,4-dioxothiazolidin-5-ylmethyl group; and/or (E4) R represents a hydrogen atom; and/or (E5) m is an integer of from 1 to 5;

and especially compounds in which X is as defined in (E1), Y is as defined in (E2), Z is as defined in (E3), R is as defined in (E4) and m is as defined in (E5).

The compounds of the present invention each contains a basic group in its molecule, and can thus be converted to salts with acids by conventional methods. There is no particular restriction on the nature of such salts, provided that, where the compounds are to be used medically; the compounds are pharmaceutically acceptable, that is it is not less active, or unacceptably less active, nor more toxic, or unacceptably more toxic, than the parent compound. However, where the compound is to be used for non-medical uses, e.g. as an intermediate in the preparation of other compounds, even this restriction does not apply, and there is then no restriction on the nature of the salts which may be formed. Examples of such salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. We prefer the pharmaceutically acceptable salts.

Also, the compound of the present invention can be converted into a salt with a base by conventional methods. Examples of such salts include: salts with an alkali metal, such as sodium, potassium or lithium; salts with an alkaline earth metal, such as barium or calcium; and salts with another metal, such as magnesium or aluminum. We prefer the pharmaceutically acceptable salts.

The compounds of formula (I) of the present invention can exist in the form of various isomers due to the presence of asymmetric carbon atoms. Thus, where an indoline or azaindoline ring is substituted at the 2-or 3-position, the carbon atoms at these positions are asymmetric and, where Z represents a 2,4-dioxothiazolidin-5-ylmethyl or 2,4-dioxooxazolidin-5-ylmethyl group, the carbon atom at the 5-position is asymmetric. Although these isomers are all represented herein by a single molecular formula (I), the present invention includes both the individual, isolated isomers and mixtures, including racemates, thereof and the isomers may be present in such mixtures in any proportions. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

The compounds of formula (I) wherein Z represents a 2,4-dioxothiazolidin-5-ylmethyl, 2,4-dioxothiazolidin-5-ylidenylmethyl, 2,4-dioxooxazolidin-5-ylmethyl or 3,5-dioxooxadiazolidin-2-ylmethyl group can exist in the form of various tautomeric isomers as shown in the following schemes α, β, γ and δ, respectively:

Scheme α

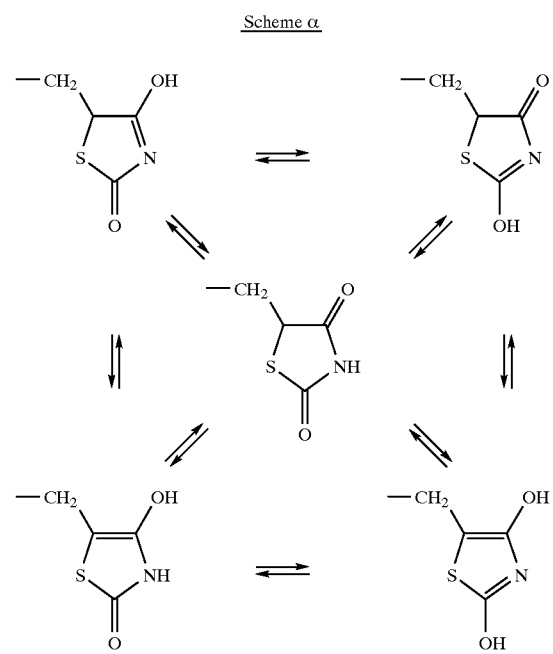

Scheme β

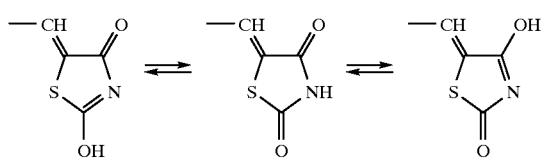

Scheme γ

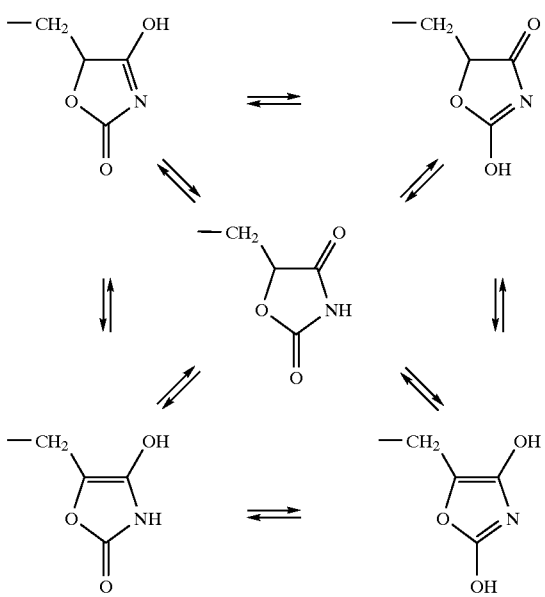

Scheme δ

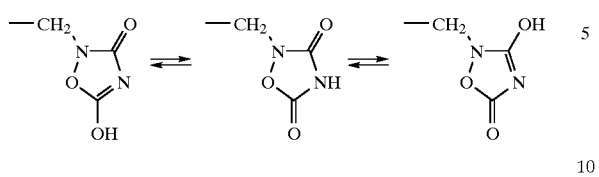

In the above formula (I), all tautomers based thereon and mixtures of equivalent weights or non-equivalent weights of these tautomers are represented by one formula. Thus, all of these isomers and mixtures of these isomers are included in the present invention.

Moreover, the present invention also includes all solvates, for example hydrates, of the compounds of formula (I) and salts thereof, where the relevant compound is capable of forming a solvate.

The invention also embraces all compounds which could be converted in the living mammalian, for example human, body to a compound of formula (I) or a salt thereof by the action of the metabolism, that is so-called "pro-drugs" of the compounds of formula (I) and salts thereof.

Examples of certain compounds of the present invention are given in the following formulae (I-1) to (I-5):

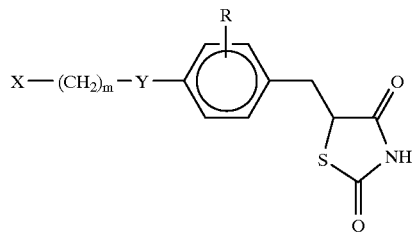
(I-1)

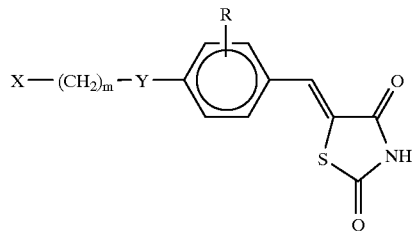
(I-2)

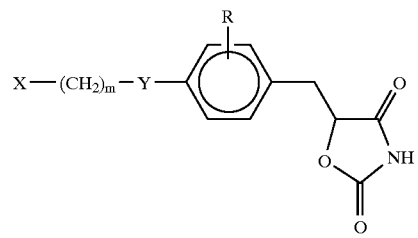
(I-3)

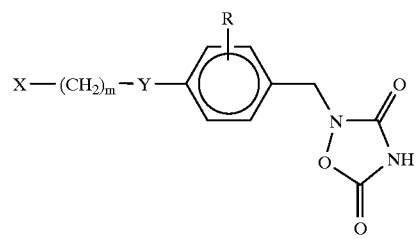
(I-4)

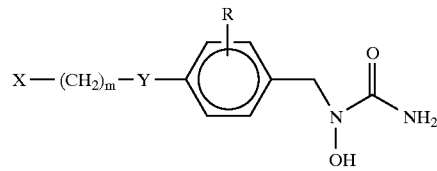
(I-5)

In the formulae, the substituents are as defined in the following one of Tables 1 to 5, respectively. That is, Table 1 relates to formula (I-1), Table 2 relates to formula (I-2), and so on to Table 5, which relates to formula (I-5). In the Tables, the following abbreviations are used:

Ac acetyl
Bu butyl
iBu isobutyl
tBu t-butyl
Bz benzyl
Et ethyl
Me methyl
Ph phenyl
Pr propyl
iPr isopropyl
Prn propionyl

TABLE 1

| Cpd. No. | X | Y | m | R |
|---|---|---|---|---|
| 1-1 | indole (N-methyl) | O | 2 | H |

TABLE 1-continued

| Cpd. No. | X | Y | m | R |
|---|---|---|---|---|
| 1-2 | 3-methyl-1H-indole | O | 2 | H |
| 1-3 | 3-CPh₃-1-methyl-indole | O | 2 | H |
| 1-4 | 3-methyl-1-Me-indole | O | 2 | H |
| 1-5 | 2-methyl-1H-indole | O | 1 | H |
| 1-6 | 2-methyl-1-Me-indole | O | 1 | H |
| 1-7 | 2-methyl-1-Me-indole | O | 2 | H |
| 1-8 | 2-methyl-1-Et-indole | O | 1 | H |
| 1-9 | 3-methyl-1-Me-indole | O | 3 | H |
| 1-10 | 5-MeO-2,3-dimethyl-1-Me-indole | O | 1 | H |

TABLE 1-continued

| Cpd. No. | X | Y | m | R |
|---|---|---|---|---|
| 1-11 | 5-HO, 1-Me, 3-yl indole | O | 5 | Me |
| 1-12 | 1-iPr, 3-yl indole | S | 1 | H |
| 1-13 | 1-Me, 2-Et, 3-yl indole | O | 2 | MeO |
| 1-14 | 5-MeO, 1-Me, 3-yl indole | O | 1 | H |
| 1-15 | 5-HO, 1-Me, 2-Me, 3-yl indole | O | 1 | H |
| 1-16 | 5-BuO, 1-Me, 3-yl indole | O | 1 | H |
| 1-17 | 4-Me, 7-Me, 1-Me, 3-yl indole | S | 4 | Cl |
| 1-18 | 6-Me, 1-Me, 3-yl indole | O | 3 | OH |

TABLE 1-continued
| Cpd. No. | X | Y | m | R |
|---|---|---|---|---|
| 1-19 | 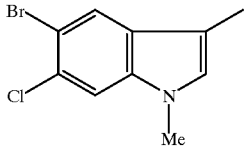 | S | 2 | Bu |
| 1-20 | 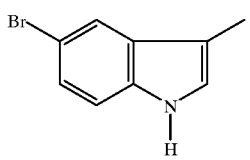 | O | 5 | H |
| 1-21 | 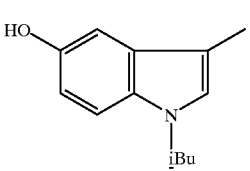 | O | 1 | H |
| 1-22 | 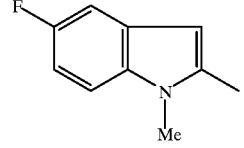 | O | 1 | H |
| 1-23 | 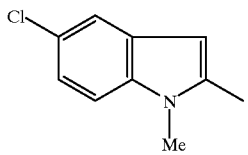 | O | 1 | H |
| 1-24 | 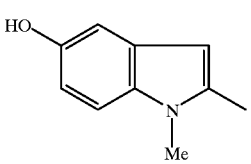 | O | 1 | H |
| 1-25 | 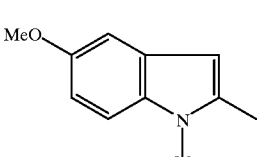 | O | 1 | H |
| 1-26 | 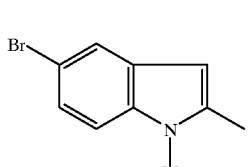 | O | 1 | H |
| 1-27 | 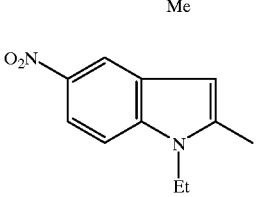 | O | 1 | H |

TABLE 1-continued

| Cpd. No. | X | Y | m | R |
|---|---|---|---|---|
| 1-28 | 5-Me, 1-Me, 2-Me indole | O | 1 | H |
| 1-29 | 5-H₂N, 1-Me, 2-Me indole | O | 1 | H |
| 1-30 | 5-AcHN, 1-Me, 2-Me indole | O | 1 | H |
| 1-31 | 5-(PhC(O)NH), 1-Et, 2-Me indole | O | 1 | H |
| 1-32 | 5-(MeNH), 1-Me, 2-Me indole | O | 1 | H |
| 1-33 | 5-(BuNH), 1-Me, 2-Me indole | O | 1 | H |
| 1-34 | 5-(BzN(Me)), 1-Me, 2-Me indole | O | 1 | H |

TABLE 1-continued

| Cpd. No. | X | Y | m | R |
|---|---|---|---|---|
| 1-35 | 5-(PhNH)-1-Me-2-Me-indole | O | 1 | H |
| 1-36 | 5-(AcHN)-2-Me-indole (NH) | S | 2 | Me |
| 1-37 | 5-(PhC(O)NH)-1-Bu-2-Me-indole | O | 4 | MeO |
| 1-38 | 4-Cl-1-Me-2-Me-indole | O | 1 | H |
| 1-39 | 3-OMe-1-Me-2-Me-indole | O | 1 | H |
| 1-40 | 6-F-1-Me-2-Me-indole | O | 1 | H |
| 1-41 | 6-Cl-1-Et-2-Me-indole | O | 2 | Cl |
| 1-42 | 6-MeO-1-Me-2-Me-indole | O | 1 | H |

TABLE 1-continued
| Cpd. No. | X | Y | m | R |
|---|---|---|---|---|
| 1-43 | 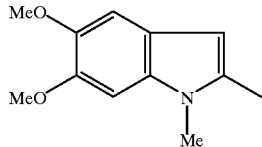 | O | 4 | H |
| 1-44 | 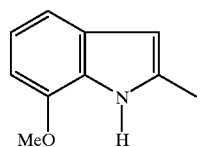 | S | 1 | H |
| 1-45 | 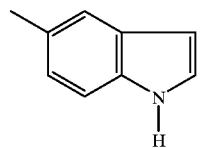 | O | 1 | H |
| 1-46 | 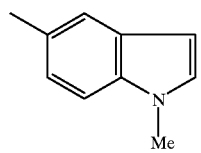 | O | 1 | H |
| 1-47 | 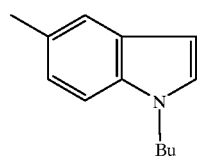 | O | 2 | H |
| 1-48 | 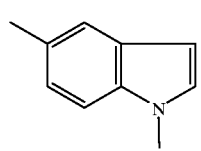 | S | 1 | Me |
| 1-49 | 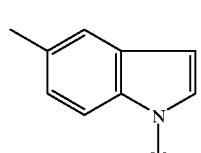 | O | 4 | Me |
| 1-50 | 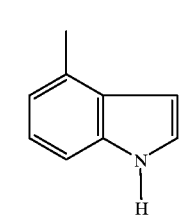 | O | 1 | H |

TABLE 1-continued
| Cpd. No. | X | Y | m | R |
|---|---|---|---|---|
| 1-51 | 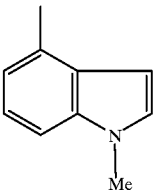 | O | 1 | H |
| 1-52 | 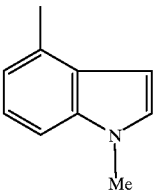 | O | 2 | H |
| 1-53 | 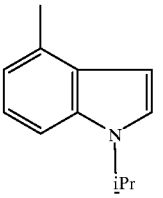 | O | 2 | Me |
| 1-54 | 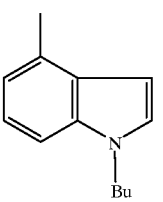 | S | 3 | H |
| 1-55 | 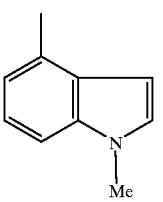 | O | 1 | MeO |
| 1-56 | 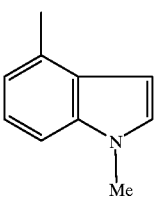 | S | 1 | H |
| 1-57 | 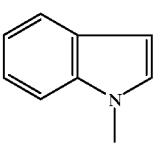 | O | 2 | H |

TABLE 1-continued

| Cpd. No. | X | Y | m | R |
|---|---|---|---|---|
| 1-58 | 5-MeO-1-Me-indole | O | 4 | Me |
| 1-59 | 2-methylindoline (NH) | O | 1 | H |
| 1-60 | 2-methylindoline (NH) | O | 2 | H |
| 1-61 | 2-methylindoline (NH) | S | 3 | H |
| 1-62 | 1,2-dimethylindoline | O | 1 | H |
| 1-63 | 1,2-dimethylindoline | O | 2 | H |
| 1-64 | 1,2-dimethylindoline | O | 3 | H |
| 1-65 | 1,2-dimethylindoline | S | 1 | H |
| 1-66 | 1-Et-2-methylindoline | O | 1 | H |

TABLE 1-continued

| Cpd. No. | X | Y | m | R |
|---|---|---|---|---|
| 1-67 | 2-methylindoline, N-Pr | O | 2 | MeO |
| 1-68 | 2-methylindoline, N-Bu | O | 1 | H |
| 1-69 | 2-methylindoline, N-Me | S | 5 | H |
| 1-70 | 2-methylindoline, N-Me | O | 1 | Cl |
| 1-71 | 2-methylindoline, N-iPr | O | 1 | H |
| 1-72 | 7-azaindole, N-Me | O | 2 | H |
| 1-73 | 7-azaindole, N-Me | S | 3 | H |
| 1-74 | 7-azaindole, N-Me | O | 4 | H |
| 1-75 | 7-azaindole, N-H, 3-methyl | O | 1 | H |

TABLE 1-continued

| Cpd. No. | X | Y | m | R |
|---|---|---|---|---|
| 1-76 | 7-azaindol-3-yl (N-H), methyl at 3 | O | 3 | H |
| 1-77 | 7-azaindol-3-yl (N-Me) | O | 1 | H |
| 1-78 | 7-azaindol-3-yl (N-Me) | O | 2 | H |
| 1-79 | 7-azaindol-3-yl (N-Me) | S | 3 | Me |
| 1-80 | 7-azaindol-3-yl (N-iPr) | O | 2 | Cl |
| 1-81 | 7-azaindol-2-yl (N-Me) | O | 1 | H |
| 1-82 | 7-azaindol-2-yl (N-Me) | O | 2 | H |
| 1-83 | 2,3-dihydro-7-azaindol-2-yl (N-H) | O | 1 | H |
| 1-84 | 2,3-dihydro-7-azaindol-2-yl (N-Me) | S | 1 | H |

TABLE 1-continued

| Cpd. No. | X | Y | m | R |
|---|---|---|---|---|
| 1-85 | (2,3-dihydro-1-methyl-1H-pyrrolo[2,3-b]pyridin-2-yl) | O | 2 | H |
| 1-86 | (2,3-dihydro-1-ethyl-1H-pyrrolo[2,3-b]pyridin-2-yl) | O | 1 | H |
| 1-87 | (2,3-dihydro-1-isopropyl-1H-pyrrolo[2,3-b]pyridin-2-yl) | O | 1 | Me |
| 1-88 | (2,3-dihydro-1-butyl-1H-pyrrolo[2,3-b]pyridin-2-yl) | S | 4 | H |
| 1-89 | (1-methyl-1H-imidazo[4,5-b]pyridin-2-yl) | O | 2 | H |
| 1-90 | (1-methyl-1H-imidazo[4,5-b]pyridin-2-yl) | S | 3 | H |
| 1-91 | (2-methyl-1H-imidazo[4,5-b]pyridin-2-yl) | O | 1 | H |
| 1-92 | (7-methyl-2-methyl-1H-imidazo[4,5-b]pyridin-2-yl) | O | 2 | H |
| 1-93 | (1,2-dimethyl-1H-imidazo[4,5-b]pyridin-2-yl) | O | 1 | H |
| 1-94 | (1-butyl-2-methyl-1H-imidazo[4,5-b]pyridin-2-yl) | O | 1 | H |

TABLE 1-continued
| Cpd. No. | X | Y | m | R |
|---|---|---|---|---|
| 1-95 | 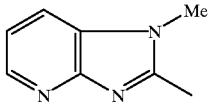 | O | 1 | Me |
| 1-96 | 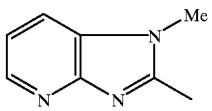 | S | 1 | H |
| 1-97 | 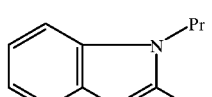 | S | 5 | H |
| 1-98 |  | O | 3 | H |
| 1-99 | 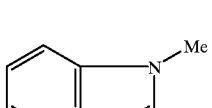 | O | 4 | MeO |
| 1-100 | 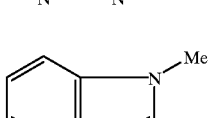 | O | 5 | Cl |
| 1-101 | 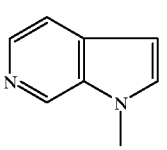 | O | 2 | H |
| 1-102 | 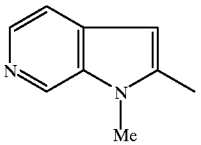 | O | 1 | H |
| 1-103 | 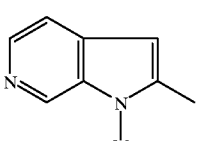 | O | 2 | H |
| 1-104 | 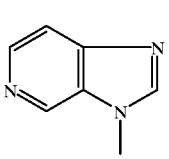 | O | 2 | H |

TABLE 1-continued

| Cpd. No. | X | Y | m | R |
|---|---|---|---|---|
| 1-105 | imidazo[4,5-c]pyridine, N-substituted | O | 4 | H |
| 1-106 | 2-methylimidazo[1,2-a]pyridine | O | 1 | H |
| 1-107 | 2-methylimidazo[1,2-a]pyridine | O | 2 | H |
| 1-108 | 6,8-dibromo-2-methylimidazo[1,2-a]pyridine | O | 3 | H |
| 1-109 | 2-methylimidazo[1,2-a]pyridine | S | 1 | H |
| 1-110 | 8-hydroxy-2-methylimidazo[1,2-a]pyridine | O | 1 | H |
| 1-111 | 6-chloro-2-methylimidazo[1,2-a]pyridine | O | 1 | H |
| 1-112 | 6-chloro-2-methylimidazo[1,2-a]pyridine | O | 2 | H |
| 1-113 | 6-chloro-2-methylimidazo[1,2-a]pyridine | S | 1 | H |
| 1-114 | 7-methylimidazo[1,2-a]pyridine | O | 1 | H |
| 1-115 | 7-methylimidazo[1,2-a]pyridine | O | 3 | H |

TABLE 1-continued

| Cpd. No. | X | Y | m | R |
|---|---|---|---|---|
| 1-116 | 7-methyl-2-methyl-imidazo[1,2-a]pyridine | O | 1 | H |
| 1-117 | 7-methyl-2-methyl-imidazo[1,2-a]pyridine | O | 1 | H |
| 1-118 | 8-methyl-imidazo[1,2-a]pyridine | O | 1 | H |
| 1-119 | 8-methyl-imidazo[1,2-a]pyridine | O | 5 | Me |
| 1-120 | 8-methyl-2-ethyl-imidazo[1,2-a]pyridine | O | 1 | MeO |
| 1-121 | 1-ethyl-2-methyl-imidazo[4,5-b]pyridine | O | 1 | H |
| 1-122 | 1,2-dimethyl-imidazo[4,5-b]pyridine | O | 1 | H |
| 1-123 | 1,2-dimethyl-imidazo[4,5-b]pyridine | O | 3 | H |
| 1-124 | 7,1-dimethyl-2-methyl-imidazo[4,5-b]pyridine | O | 1 | H |

TABLE 1-continued
| Cpd. No. | X | Y | m | R |
|---|---|---|---|---|
| 1-125 | 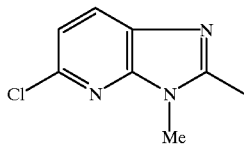 | O | 1 | H |
| 1-126 | 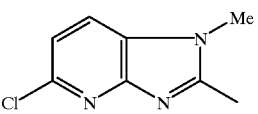 | O | 1 | H |
| 1-127 | 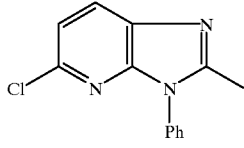 | O | 3 | H |
| 1-128 | 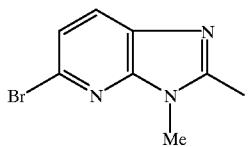 | O | 1 | H |
| 1-129 | 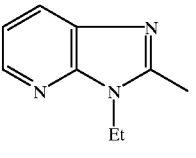 | O | 2 | H |
| 1-130 | 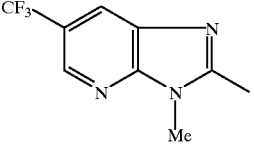 | O | 1 | H |
| 1-131 | 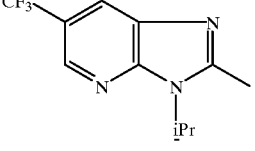 | O | 4 | H |
| 1-132 | 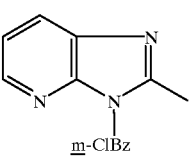 | O | 1 | H |
| 1-133 | 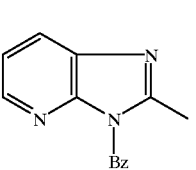 | O | 1 | H |

TABLE 1-continued

| Cpd. No. | X | Y | m | R |
|---|---|---|---|---|
| 1-134 | imidazo[4,5-b]pyridine, N-(p-ClBz), 2-Me | O | 1 | H |
| 1-135 | imidazo[4,5-b]pyridine, N-(p-PhBz), 2-Me | O | 1 | H |
| 1-136 | imidazo[4,5-b]pyridine, N-(p-PhBz), 2-Me | O | 3 | H |
| 1-137 | 6-Br-imidazo[4,5-b]pyridine, N-Me, 2-Me | O | 1 | H |
| 1-138 | 6-Br-imidazo[4,5-b]pyridine, N-Et, 2-Me | O | 3 | H |
| 1-139 | 6-Br-imidazo[4,5-b]pyridine, N-Ph, 2-Me | S | 5 | MeO |
| 1-140 | 6-Cl-imidazo[4,5-b]pyridine, N-Me, 2-Me | O | 1 | H |
| 1-141 | 6-Cl-imidazo[4,5-b]pyridine, N-Bu, 2-Me | O | 3 | H |

TABLE 1-continued

| Cpd. No. | X | Y | m | R |
|---|---|---|---|---|
| 1-142 | 5-MeO, 1-Me, 2-Me imidazo[4,5-b]pyridine | O | 1 | H |
| 1-143 | 5-MeO, 1-Et, 2-Me imidazo[4,5-b]pyridine | O | 1 | H |
| 1-144 | 5-MeO, 1-Pr, 2-Me imidazo[4,5-b]pyridine | O | 1 | H |
| 1-145 | 5-MeO, 1-Me, 2-Me imidazo[4,5-b]pyridine | O | 2 | H |
| 1-146 | 5-MeO, 1-Me, 2-Me imidazo[4,5-b]pyridine | O | 3 | H |
| 1-147 | 5-MeO, 1-Ph, 2-Me imidazo[4,5-b]pyridine | O | 1 | H |
| 1-148 | 5-MeO, 1-Bz, 2-Me imidazo[4,5-b]pyridine | O | 1 | H |
| 1-149 | 5-MeO, 1-Me, 2-Me imidazo[4,5-b]pyridine | S | 1 | H |
| 1-150 | 5-MeO, 1-Me, 2-Me imidazo[4,5-b]pyridine | O | 1 | Me |

TABLE 1-continued

| Cpd. No. | X | Y | m | R |
|---|---|---|---|---|
| 1-151 | 5-MeO, 1-Me, 2-Me imidazo[4,5-b]pyridine | O | 1 | H |
| 1-152 | 6-MeO, 1-(m-ClPh), 2-Me imidazo[4,5-b]pyridine | O | 3 | H |
| 1-153 | 5-HO, 3-Me, 2-Me imidazo[4,5-b]pyridine | O | 1 | H |
| 1-154 | 6-HO, 1-Et, 2-Me imidazo[4,5-b]pyridine | O | 1 | H |
| 1-155 | 6-HO, 3-Bz, 2-Me imidazo[4,5-b]pyridine | O | 1 | H |
| 1-156 | 1-Me, 2-Me imidazo[4,5-c]pyridine | O | 1 | H |
| 1-157 | 1-Bu, 2-Me imidazo[4,5-c]pyridine | S | 3 | H |
| 1-158 | 9-Me, 8-Me purine | O | 1 | H |
| 1-159 | 9-Et, 8-Me purine | O | 3 | H |

TABLE 1-continued

| Cpd. No. | X | Y | m | R |
|---|---|---|---|---|
| 1-160 | imidazo[4,5-d]pyrimidine, N-(m-MeBz) | O | 1 | H |
| 1-161 | imidazo[4,5-b]pyridine, N-Ph | O | 1 | H |
| 1-162 | imidazo[4,5-b]pyridine, N-Ph | O | 2 | H |
| 1-163 | imidazo[4,5-b]pyridine, N-Ph | O | 3 | H |
| 1-164 | imidazo[4,5-b]pyridine, N-(p-ClPh) | O | 1 | H |
| 1-165 | imidazo[4,5-b]pyridine, N-(m-ClPh) | O | 1 | H |
| 1-166 | imidazo[4,5-b]pyridine, N-(o-MePh) | O | 1 | H |
| 1-167 | 5-Cl-imidazo[4,5-b]pyridine, N-(m-ClPh) | O | 3 | H |

TABLE 1-continued

| Cpd. No. | X | Y | m | R |
|---|---|---|---|---|
| 1-168 | (5-MeO, 2-Me imidazo[4,5-b]pyridine, N-m-MeOPh) | O | 1 | H |
| 1-169 | (6-Me, 5-HO, 2-Me imidazo[4,5-b]pyridine, N-Me) | O | 1 | H |
| 1-170 | (6-Me, 5-MeO, 2-Me imidazo[4,5-b]pyridine, N-Me) | O | 1 | H |
| 1-171 | (5-Me imidazo[4,5-b]pyridine, N-Me) | O | 2 | H |
| 1-172 | (5-Me, 2-Me imidazo[4,5-b]pyridine, N-Me) | O | 2 | H |
| 1-173 | (5-Me, 2-Me imidazo[4,5-b]pyridine, N-Et) | O | 2 | H |
| 1-174 | (5-Me, 2-Ph imidazo[4,5-b]pyridine, N-Me) | O | 2 | H |
| 1-175 | (5-Me imidazo[4,5-b]pyridine, N-Me, 2-CH2CH2-(3,5-di-tBu-4-OH-phenyl)) | O | 2 | H |

TABLE 1-continued

| Cpd. No. | X | Y | m | R |
|---|---|---|---|---|
| 1-176 | 5-methyl-1-methyl-2-(m-ClPh)-imidazo[4,5-b]pyridine | O | 2 | H |
| 1-177 | 5-(PhS)-1-methyl-2-methyl-imidazo[4,5-b]pyridine | O | 1 | H |
| 1-178 | 5-(BuS)-1-methyl-2-methyl-imidazo[4,5-b]pyridine | O | 1 | H |
| 1-179 | 5-Ph-1-methyl-2-methyl-imidazo[4,5-b]pyridine | O | 1 | H |
| 1-180 | 5-Ph-1-methyl-2-methyl-imidazo[4,5-b]pyridine | O | 3 | H |
| 1-181 | 5-[(3,5-di-tBu-4-HO-phenyl)S]-1-methyl-2-methyl-imidazo[4,5-b]pyridine | O | 1 | H |
| 1-182 | 5-EtO-1-methyl-2-methyl-imidazo[4,5-b]pyridine | O | 1 | H |
| 1-183 | 5-iPrO-1-methyl-2-methyl-imidazo[4,5-b]pyridine | O | 1 | H |

TABLE 1-continued

| Cpd. No. | X | Y | m | R |
|---|---|---|---|---|
| 1-184 | 6-MeO, 1-Me, 2-Me imidazo[4,5-b]pyridine | O | 1 | H |
| 1-185 | 5-AcO, 1-Me, 2-Me imidazo[4,5-b]pyridine | O | 1 | H |
| 1-186 | 5-AcO, 1-Me, 2-Me imidazo[4,5-b]pyridine | O | 3 | H |
| 1-187 | 6-CF₃, 5-PhO, 1-Et, 2-Me imidazo[4,5-b]pyridine | O | 1 | H |
| 1-188 | 7-Cl, 1-Me, 2-Me imidazo[4,5-b]pyridine | O | 1 | H |
| 1-189 | 7-Cl, 1-Pr, 2-Me imidazo[4,5-b]pyridine | O | 3 | H |
| 1-190 | 1-Me, 2-Me imidazo[4,5-b]pyridine | O | 2 | H |
| 1-191 | 5-Me, 6-HO, 7-Me, 1-Me, 2-Me imidazo[4,5-b]pyridine | O | 1 | H |

TABLE 1-continued

| Cpd. No. | X | Y | m | R |
|---|---|---|---|---|
| 1-192 | 6-HO, 5,7-Me, 2-Me, N-Me imidazo[4,5-b]pyridine | O | 2 | H |
| 1-193 | 6-O₂N, 5,7-Me, 2-Me, N-Me imidazo[4,5-b]pyridine | O | 1 | H |
| 1-194 | 6-H₂N, 5,7-Me, 2-Me, N-Me imidazo[4,5-b]pyridine | O | 1 | H |
| 1-195 | 5-MeNH, 2-Me, N-Me imidazo[4,5-b]pyridine | O | 1 | H |
| 1-196 | 5-Me₂N, 2-Me, N-Me imidazo[4,5-b]pyridine | O | 1 | H |
| 1-197 | 5-(Bu)(Et)N, 2-Me, N-Me imidazo[4,5-b]pyridine | O | 1 | H |
| 1-198 | 5-PhNH, 2-Me, N-Me imidazo[4,5-b]pyridine | O | 1 | H |
| 1-199 | 5-BzNH, 2-Me, N-Me imidazo[4,5-b]pyridine | O | 1 | H |

TABLE 1-continued

| Cpd. No. | X | Y | m | R |
|---|---|---|---|---|
| 1-200 | (Ph)(Et)N-substituted imidazo[4,5-b]pyridine, N-Me, 2-Me | O | 1 | H |
| 1-201 | AcNH-substituted imidazo[4,5-b]pyridine, N-Me, 2-Me | O | 1 | H |
| 1-202 | PhC(O)NH-substituted imidazo[4,5-b]pyridine, N-Me, 2-Me | O | 1 | H |
| 1-203 | O₂N-substituted imidazo[4,5-b]pyridine, N-Me, 2-Me | O | 1 | H |
| 1-204 | H₂N-substituted imidazo[4,5-b]pyridine, N-Me, 2-Me | O | 1 | H |
| 1-205 | PhC(O)NH-substituted imidazo[4,5-b]pyridine, N-Me, 2-Me | O | 1 | H |
| 1-206 | BuCONH-substituted imidazo[4,5-b]pyridine, N-Bu, 2-Me | S | 2 | H |
| 1-207 | BzO-substituted imidazo[4,5-b]pyridine, N-Me, 2-Me | O | 1 | H |
| 1-208 | BzO-substituted imidazo[4,5-b]pyridine, N-Me, 2-Me | S | 1 | H |

TABLE 1-continued

| Cpd. No. | X | Y | m | R |
|---|---|---|---|---|
| 1-209 | 5-methyl-3-methyl-2-hydroxy-imidazo[4,5-b]pyridine | O | 2 | H |
| 1-210 | 5-methyl-2-hydroxy-1H-imidazo[4,5-b]pyridine | O | 2 | H |
| 1-211 | 5-methyl-3-phenyl-2-hydroxy-imidazo[4,5-b]pyridine | O | 2 | H |
| 1-212 | 5-methyl-2-methylthio-1H-imidazo[4,5-b]pyridine | O | 2 | H |
| 1-213 | 5-methyl-3-methyl-2-methylthio-imidazo[4,5-b]pyridine | O | 2 | H |
| 1-214 | 5-methyl-3-benzyl-2-butylthio-imidazo[4,5-b]pyridine | O | 2 | H |
| 1-215 | 5-tBuNH-3-methyl-2-methyl-imidazo[4,5-b]pyridine | O | 1 | H |
| 1-216 | 5-tBuNH-3-propyl-2-methyl-imidazo[4,5-b]pyridine | O | 1 | H |
| 1-217 | 5-tBuNH-3-methyl-2-methyl-imidazo[4,5-b]pyridine | S | 1 | H |

TABLE 1-continued

| Cpd. No. | X | Y | m | R |
|---|---|---|---|---|
| 1-218 | 2,3,7-trimethyl-3H-imidazo[4,5-b]pyridine (Me at 7, Me at 5, Me at 2, N-Me) | O | 1 | H |
| 1-219 | 5,7-dimethyl-2-methyl-3-(mClPh)-3H-imidazo[4,5-b]pyridine | O | 1 | H |
| 1-220 | 5,7-dimethyl-2-methyl-3-(3,5-di-tBu-4-hydroxybenzyl)-3H-imidazo[4,5-b]pyridine | O | 1 | H |
| 1-221 | 5-AcO-2-methyl-3-methyl-3H-imidazo[4,5-b]pyridine | O | 1 | H |
| 1-222 | 5-AcO-2-methyl-3-ethyl-3H-imidazo[4,5-b]pyridine | O | 1 | H |

TABLE 2

| Cpd. No. | X | Y | m | R |
|---|---|---|---|---|
| 2-1 | 1-methylindole | O | 2 | H |

TABLE 2-continued
| Cpd. No. | X | Y | m | R |
|---|---|---|---|---|
| 2-2 | 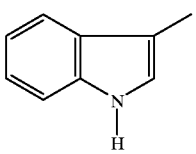 | O | 2 | H |
| 2-3 | 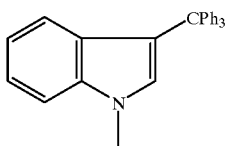 | O | 2 | H |
| 2-4 | 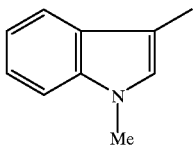 | O | 2 | H |
| 2-5 | 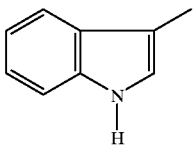 | O | 1 | H |
| 2-6 | 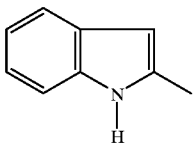 | O | 1 | H |
| 2-7 | 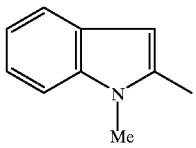 | O | 2 | H |
| 2-8 | 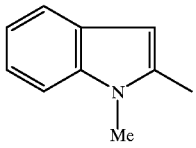 | O | 1 | H |
| 2-9 | 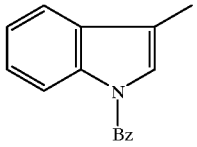 | O | 3 | H |
| 2-10 | 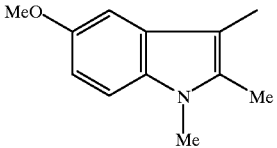 | O | 1 | H |

TABLE 2-continued
| Cpd. No. | X | Y | m | R |
|---|---|---|---|---|
| 2-11 | 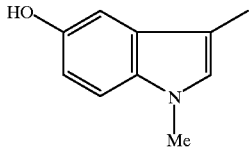 | O | 5 | Me |
| 2-12 | 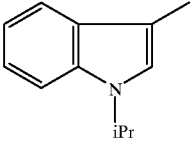 | S | 1 | H |
| 2-13 | 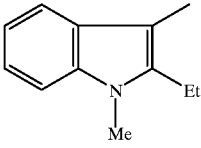 | O | 2 | MeO |
| 2-14 | 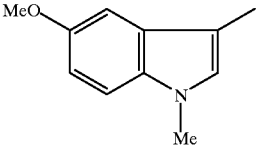 | O | 1 | H |
| 2-15 | 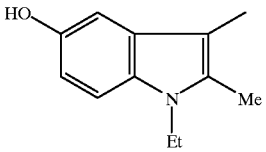 | O | 1 | H |
| 2-16 | 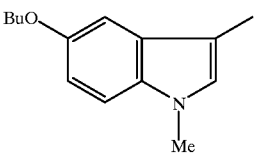 | O | 1 | H |
| 2-17 | 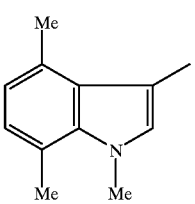 | S | 4 | Cl |
| 2-18 | 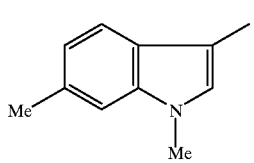 | O | 3 | OH |

TABLE 2-continued
| Cpd. No. | X | Y | m | R |
|---|---|---|---|---|
| 2-19 | 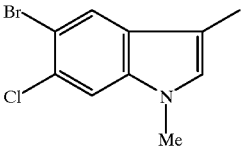 | S | 2 | Bu |
| 2-20 | 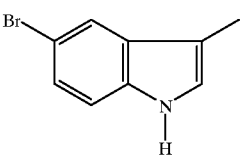 | O | 5 | H |
| 2-21 | 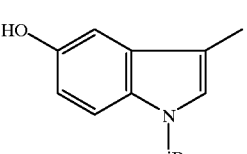 | O | 1 | H |
| 2-22 | 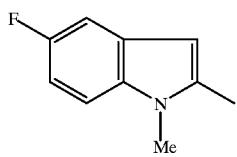 | O | 1 | H |
| 2-23 | 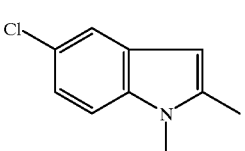 | O | 1 | H |
| 2-24 | 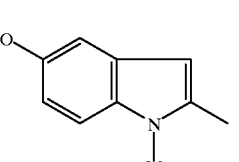 | O | 1 | H |
| 2-25 | 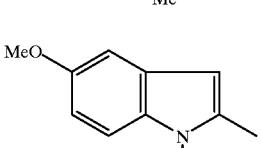 | O | 1 | H |
| 2-26 | 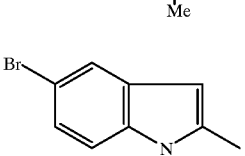 | O | 1 | H |
| 2-27 | 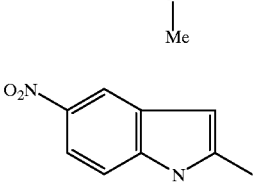 | O | 1 | H |

TABLE 2-continued

| Cpd. No. | X | Y | m | R |
|---|---|---|---|---|
| 2-28 | 5-Me, 2-Me, N-Me indole | O | 1 | H |
| 2-29 | 5-H₂N, 2-Me, N-Me indole | O | 1 | H |
| 2-30 | 5-AcHN, 2-Me, N-Me indole | O | 1 | H |
| 2-31 | 5-PhC(O)NH, 2-Me, N-Et indole | O | 1 | H |
| 2-32 | 5-Me₂N, 2-Me, N-Me indole | O | 1 | H |
| 2-33 | 5-BuNH, 2-Me, N-Me indole | O | 1 | H |
| 2-34 | 5-Bz(Me)N, 2-Me, N-Me indole | O | 1 | H |
| 2-35 | 5-PhNH, 2-Me, N-Me indole | O | 1 | H |

TABLE 2-continued

| Cpd. No. | X | Y | m | R |
|---|---|---|---|---|
| 2-36 | AcNH-(5-indolyl), N-H, 2-Me | S | 2 | Me |
| 2-37 | PhC(O)NH-(5-indolyl), N-Bu, 2-Me | O | 4 | MeO |
| 2-38 | 4-Cl-indolyl, N-Me, 2-Me | O | 1 | H |
| 2-39 | 3-OMe-indolyl, N-tBu, 2-Me | O | 1 | H |
| 2-40 | 6-F-indolyl, N-Me, 2-Me | O | 1 | H |
| 2-41 | 6-Cl-indolyl, N-Et, 2-Me | O | 2 | Cl |
| 2-42 | 6-MeO-indolyl, N-Me, 2-Me | O | 1 | H |
| 2-43 | 5,6-diMeO-indolyl, N-Me, 2-Me | O | 4 | H |

TABLE 2-continued

| Cpd. No. | X | Y | m | R |
|---|---|---|---|---|
| 2-44 | 7-MeO, 2-Me indole (NH) | S | 1 | H |
| 2-45 | 5-Me indole (NH) | O | 1 | H |
| 2-46 | 5-Me indole (N-Me) | O | 1 | H |
| 2-47 | 5-Me indole (N-Bu) | O | 2 | H |
| 2-48 | 5-Me indole (N-Et) | S | 1 | Me |
| 2-49 | 5-Me indole (N-Me) | O | 4 | Me |
| 2-50 | 4-Me indole (NH) | O | 1 | H |
| 2-51 | 4-Me indole (N-Me) | O | 1 | H |

TABLE 2-continued

| Cpd. No. | X | Y | m | R |
|---|---|---|---|---|
| 2-52 | 4-methyl-1-methyl-indole | S | 2 | H |
| 2-53 | 4-methyl-1-iPr-indole | O | 2 | Me |
| 2-54 | 4-methyl-1-Bu-indole | S | 3 | H |
| 2-55 | 4-methyl-1-methyl-indole | O | 1 | MeO |
| 2-56 | 4-methyl-1-methyl-indole | S | 1 | H |
| 2-57 | 1-methyl-indoline | O | 2 | H |
| 2-58 | 5-MeO-1-methyl-indoline | O | 4 | Me |
| 2-59 | 2-methyl-indoline (NH) | O | 1 | H |

TABLE 2-continued
| Cpd. No. | X | Y | m | R |
|---|---|---|---|---|
| 2-60 | 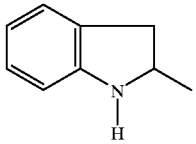 | O | 2 | H |
| 2-61 | 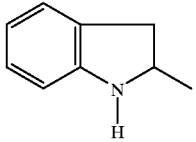 | S | 3 | H |
| 2-62 | 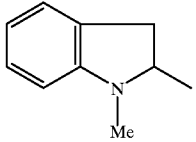 | O | 1 | H |
| 2-63 | 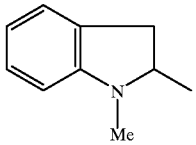 | O | 2 | H |
| 2-64 | 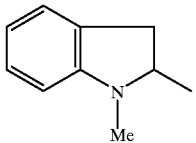 | O | 3 | H |
| 2-65 | 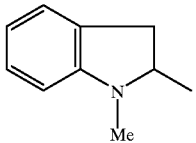 | S | 1 | H |
| 2-66 | 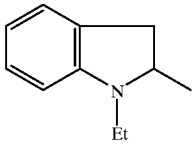 | O | 1 | H |
| 2-67 | 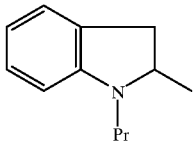 | O | 2 | MeO |
| 2-68 | 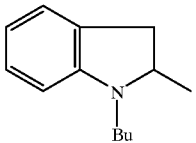 | O | 1 | H |

TABLE 2-continued
| Cpd. No. | X | Y | m | R |
|---|---|---|---|---|
| 2-69 | 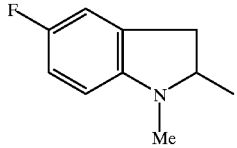 | S | 5 | H |
| 2-70 | 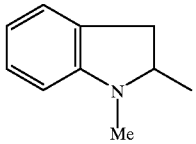 | O | 1 | Cl |
| 2-71 | 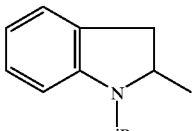 | O | 1 | H |
| 2-72 | 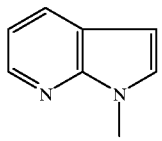 | O | 2 | H |
| 2-73 | 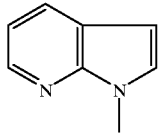 | S | 3 | H |
| 2-74 | 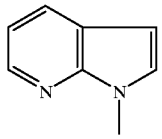 | O | 4 | H |
| 2-75 | 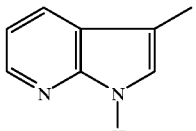 | O | 1 | H |
| 2-76 | 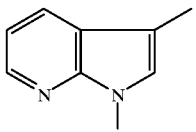 | O | 3 | H |
| 2-77 | 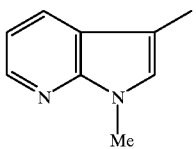 | O | 1 | H |

TABLE 2-continued

| Cpd. No. | X | Y | m | R |
|---|---|---|---|---|
| 2-78 | 7-azaindole, N-Me, 3-Me | O | 2 | H |
| 2-79 | 7-azaindole, N-Me, 3-Me | S | 3 | Me |
| 2-80 | 7-azaindole, N-iPr, 3-Me | O | 2 | Cl |
| 2-81 | 7-azaindole, N-Me, 2-Me | O | 1 | H |
| 2-82 | 7-azaindole, N-Me, 2-Me | O | 2 | H |
| 2-83 | 5-Me-2,3-dihydro-7-azaindole, 2-Me, N-H | O | 1 | H |
| 2-84 | 2,3-dihydro-7-azaindole, N-Me, 2-Me | S | 1 | H |
| 2-85 | 2,3-dihydro-7-azaindole, N-Me, 2-Me | O | 2 | H |
| 2-86 | 2,3-dihydro-7-azaindole, N-Et, 2-Me | O | 1 | H |

TABLE 2-continued
| Cpd. No. | X | Y | m | R |
|---|---|---|---|---|
| 2-87 | 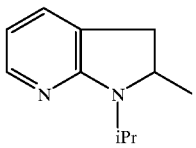 | O | 1 | Me |
| 2-88 | 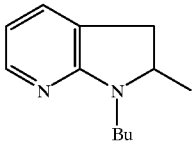 | S | 4 | H |
| 2-89 | 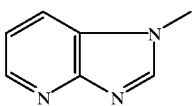 | O | 2 | H |
| 2-90 | 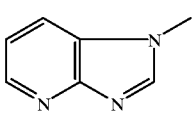 | S | 3 | H |
| 2-91 | 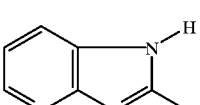 | O | 1 | H |
| 2-92 | 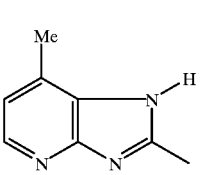 | O | 2 | H |
| 2-93 | 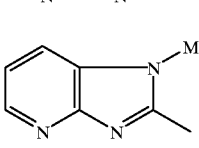 | O | 1 | H |
| 2-94 | 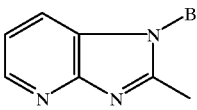 | O | 1 | H |
| 2-95 | 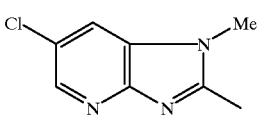 | O | 1 | Me |
| 2-96 | 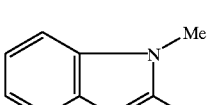 | S | 1 | H |
| 2-97 | 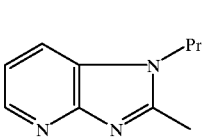 | S | 5 | H |

TABLE 2-continued

| Cpd. No. | X | Y | m | R |
|---|---|---|---|---|
| 2-98 | (1,2-dimethyl-imidazo[4,5-b]pyridine) | O | 3 | H |
| 2-99 | (1,2-dimethyl-imidazo[4,5-b]pyridine) | O | 4 | MeO |
| 2-100 | (1,2-dimethyl-imidazo[4,5-b]pyridine) | O | 1 | H |
| 2-101 | (1H-pyrrolo[2,3-c]pyridine, N-Me) | O | 2 | H |
| 2-102 | (2-methyl-1-Me-pyrrolo[2,3-c]pyridine) | O | 1 | H |
| 2-103 | (1,2-dimethyl-pyrrolo[2,3-c]pyridine) | O | 2 | H |
| 2-104 | (3-methyl-imidazo[4,5-c]pyridine) | O | 2 | H |
| 2-105 | (3-methyl-imidazo[4,5-c]pyridine) | O | 4 | H |
| 2-106 | (2-methyl-imidazo[1,2-a]pyridine) | O | 1 | H |
| 2-107 | (2,5-dimethyl-imidazo[1,2-a]pyridine) | O | 2 | H |

TABLE 2-continued

| Cpd. No. | X | Y | m | R |
|---|---|---|---|---|
| 2-108 | 6,8-dibromo-2-methylimidazo[1,2-a]pyridine | O | 3 | H |
| 2-109 | 2-methylimidazo[1,2-a]pyridine | S | 1 | H |
| 2-110 | 8-hydroxy-2-methylimidazo[1,2-a]pyridine | O | 1 | H |
| 2-111 | 6-chloro-2-methylimidazo[1,2-a]pyridine | O | 1 | H |
| 2-112 | 6-chloro-2-methylimidazo[1,2-a]pyridine | O | 2 | H |
| 2-113 | 6-chloro-2-methylimidazo[1,2-a]pyridine | S | 1 | H |
| 2-114 | 7-methylimidazo[1,2-a]pyridine | O | 1 | H |
| 2-115 | 7-methylimidazo[1,2-a]pyridine | O | 3 | H |
| 2-116 | 2,7-dimethylimidazo[1,2-a]pyridine | O | 1 | H |
| 2-117 | 2,7-dimethylimidazo[1,2-a]pyridine | S | 2 | H |
| 2-118 | 8-methylimidazo[1,2-a]pyridine | O | 1 | H |

TABLE 2-continued
| Cpd. No. | X | Y | m | R |
|---|---|---|---|---|
| 2-119 | 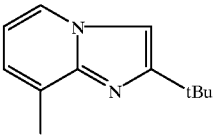 | O | 5 | Me |
| 2-120 | 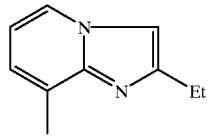 | O | 1 | MeO |
TABLE 3
| Cpd. No. | X | Y | m | R |
|---|---|---|---|---|
| 3-1 | 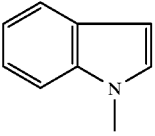 | O | 2 | H |
| 3-2 | 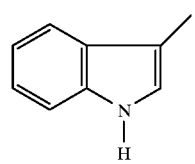 | O | 2 | H |
| 3-3 | 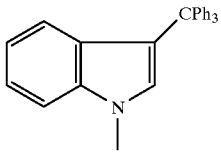 | O | 2 | H |
| 3-4 | 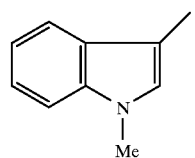 | O | 2 | H |
| 3-5 | 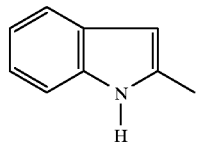 | O | 1 | H |
| 3-6 | 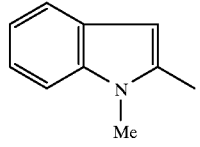 | O | 1 | H |

TABLE 3-continued

| Cpd. No. | X | Y | m | R |
|---|---|---|---|---|
| 3-7 | 2-methyl-1-methylindole | O | 2 | H |
| 3-8 | 2-methyl-1-ethylindole | O | 1 | H |
| 3-9 | 3-methyl-1-methylindole | O | 3 | MeO |
| 3-10 | 5-Me, 2-Me, 3-Me, 1-Me indole | O | 1 | H |
| 3-11 | 5-HO, 3-methyl-1-methylindole | O | 5 | Me |
| 3-12 | 3-methyl-1-iPr indole | S | 1 | H |
| 3-13 | 5-iPrO, 3-methyl, 2-Et, 1-Me indole | O | 2 | MeO |
| 3-14 | 5-MeO, 3-methyl-1-methylindole | O | 1 | H |
| 3-15 | 5-HO, 3-Me, 2-Me, 1-Me indole | O | 1 | H |

TABLE 3-continued

| Cpd. No. | X | Y | m | R |
|---|---|---|---|---|
| 3-16 | 5-BuO, N-Me indole, 3-Me | O | 1 | H |
| 3-17 | 4,7-diMe, N-Me indole, 3-Me | S | 4 | Cl |
| 3-18 | 6-Me, N-Me indole, 3-Me | O | 3 | OH |
| 3-19 | 5-Br, 6-Cl, N-Me indole, 3-Me | S | 2 | Bu |
| 3-20 | 5-Br, N-H indole, 3-Me | O | 5 | H |
| 3-21 | 5-HO, N-iBu indole, 3-Me | O | 1 | H |
| 3-22 | 5-F, N-Me indole, 2-Me | O | 1 | H |
| 3-23 | 5-Cl, N-Me indole, 2-Me | O | 1 | H |

TABLE 3-continued
| Cpd. No. | X | Y | m | R |
|---|---|---|---|---|
| 3-24 | 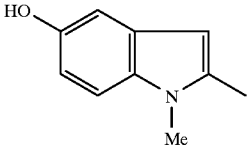 | O | 1 | H |
| 3-25 | 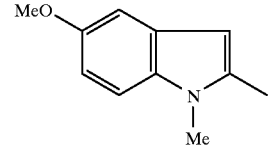 | O | 1 | H |
| 3-26 | 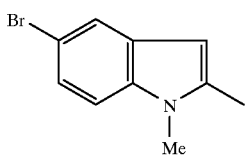 | S | 1 | H |
| 3-27 | 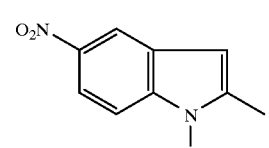 | O | 1 | H |
| 3-28 | 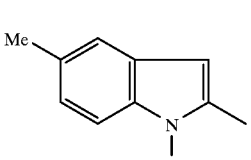 | O | 1 | H |
| 3-29 | 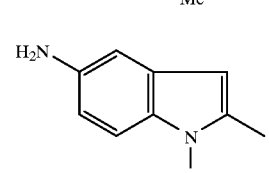 | O | 1 | H |
| 3-30 | 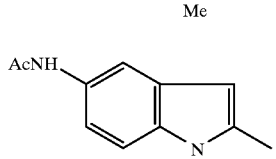 | O | 1 | H |
| 3-31 | 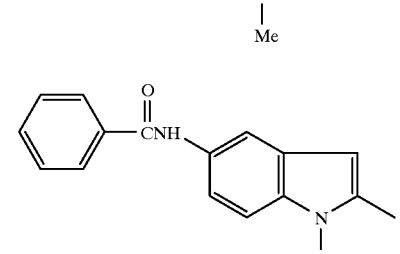 | O | 1 | H |
| 3-32 | 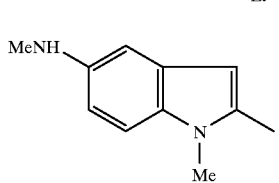 | O | 1 | H |

TABLE 3-continued

| Cpd. No. | X | Y | m | R |
|---|---|---|---|---|
| 3-33 | 5-(BuNH)-1-Me-2-Me-indole (N-H on BuN) | O | 1 | H |
| 3-34 | 5-(Bz(Me)N)-1-Me-2-Me-indole | O | 1 | H |
| 3-35 | 5-(Ph(Me)N)-1-Me-2-Me-indole | O | 1 | H |
| 3-36 | 5-(AcNH)-2-Me-indole (NH) | S | 2 | Me |
| 3-37 | 5-(PhC(O)NH)-1-Bu-2-Me-indole | O | 4 | MeO |
| 3-38 | 4-Cl-1-Me-2-Me-indole | O | 5 | H |
| 3-39 | 3-OMe-1-Me-2-Me-indole | O | 1 | H |

TABLE 3-continued

| Cpd. No. | X | Y | m | R |
|---|---|---|---|---|
| 3-40 | 6-F, 2-Me, N-Me indole | O | 1 | H |
| 3-41 | 6-Cl, 2-Me, N-Et indole | O | 2 | Cl |
| 3-42 | 6-MeO, 2-Me, N-Me indole | O | 1 | H |
| 3-43 | 5,6-diMeO, 2-Me, N-Me indole | O | 4 | H |
| 3-44 | 7-MeO, 2-Me, N-H indole | S | 1 | H |
| 3-45 | 5-Me, N-H indole | O | 1 | H |
| 3-46 | 5-Me, N-Me indole | O | 1 | H |
| 3-47 | 5-Me, N-tBu indole | O | 2 | H |
| 3-48 | 5-Me, N-Et indole | S | 1 | Me |

TABLE 3-continued

| Cpd. No. | X | Y | m | R |
|---|---|---|---|---|
| 3-49 | 5-methyl-1-methylindole | O | 4 | Me |
| 3-50 | 4-methyl-1H-indole | O | 1 | H |
| 3-51 | 4-methyl-1-methylindole | O | 1 | H |
| 3-52 | 4-methyl-1-methylindole | O | 2 | H |
| 3-53 | 4-methyl-1-iPr-indole | O | 2 | Me |
| 3-54 | 4-methyl-1-Bu-indole | S | 3 | H |
| 3-55 | 4-methyl-1-methylindole | O | 1 | MeO |

TABLE 3-continued

| Cpd. No. | X | Y | m | R |
|---|---|---|---|---|
| 3-56 | 4-methyl-5-nitro-1-methylindole | S | 1 | H |
| 3-57 | 1-methylindoline | O | 2 | H |
| 3-58 | 5-methoxy-1-methylindoline | O | 4 | Me |
| 3-59 | 2-methylindoline | O | 1 | H |
| 3-60 | 2-methylindoline | O | 2 | H |
| 3-61 | 2-methylindoline | S | 3 | H |
| 3-62 | 1,2-dimethylindoline | O | 1 | H |
| 3-63 | 1,2-dimethylindoline | O | 2 | H |
| 3-64 | 1,2-dimethylindoline | O | 3 | H |

TABLE 3-continued
| Cpd. No. | X | Y | m | R |
|---|---|---|---|---|
| 3-65 | 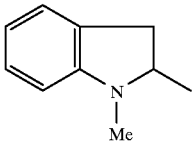 | S | 1 | H |
| 3-66 | 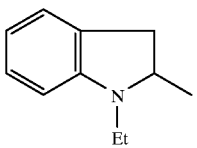 | O | 1 | H |
| 3-67 | 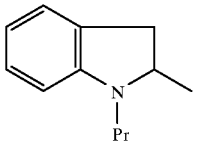 | O | 2 | MeO |
| 3-68 | 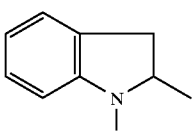 | O | 1 | H |
| 3-69 | 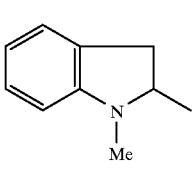 | S | 5 | H |
| 3-70 | 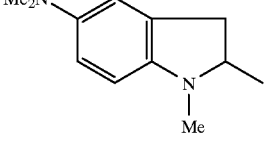 | O | 1 | Cl |
| 3-71 | 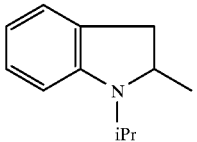 | O | 1 | H |
| 3-72 | 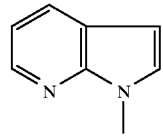 | O | 2 | H |
| 3-73 | 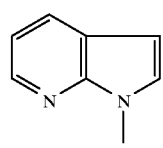 | S | 3 | H |

TABLE 3-continued

| Cpd. No. | X | Y | m | R |
|---|---|---|---|---|
| 3-74 | 7-azaindole, N-Me | O | 4 | H |
| 3-75 | 7-azaindole, N-H | O | 1 | H |
| 3-76 | 7-azaindole, N-H | O | 3 | H |
| 3-77 | 3-methyl-7-azaindole, N-Me | O | 1 | H |
| 3-78 | 3-methyl-7-azaindole, N-Me | O | 2 | H |
| 3-79 | 3-methyl-7-azaindole, N-Me | S | 3 | Me |
| 3-80 | 3-methyl-7-azaindole, N-iPr | O | 2 | Cl |
| 3-81 | 2-methyl-7-azaindole, N-Me | O | 1 | H |
| 3-82 | 2-methyl-7-azaindole, N-Me | O | 2 | H |

TABLE 3-continued

| Cpd. No. | X | Y | m | R |
|---|---|---|---|---|
| 3-83 | 7-azaindole (NH), 2-methyl | O | 1 | H |
| 3-84 | 7-azaindole, 4-Me, N-Me, 2-methyl | S | 1 | H |
| 3-85 | 7-azaindole, N-Me, 2-methyl | O | 2 | H |
| 3-86 | 7-azaindole, N-Et, 2-methyl | O | 1 | H |
| 3-87 | 7-azaindole, N-iPr, 2-methyl | O | 1 | Me |
| 3-88 | 7-azaindole, N-Bu, 2-methyl, 3-Me | S | 4 | H |
| 3-89 | imidazo[4,5-b]pyridine, N-Me | O | 2 | H |
| 3-90 | imidazo[4,5-b]pyridine, N-Me | S | 3 | H |
| 3-91 | imidazo[4,5-b]pyridine, NH, 2-methyl | O | 1 | H |

TABLE 3-continued

| Cpd. No. | X | Y | m | R |
|---|---|---|---|---|
| 3-92 | 7-methyl-2-methyl-1H-imidazo[4,5-b]pyridine | O | 2 | H |
| 3-93 | 1,2-dimethyl-imidazo[4,5-b]pyridine | O | 1 | H |
| 3-94 | 1-butyl-2-methyl-imidazo[4,5-b]pyridine | O | 1 | H |
| 3-95 | 1,2-dimethyl-imidazo[4,5-b]pyridine | O | 1 | Me |
| 3-96 | 1,2-dimethyl-imidazo[4,5-b]pyridine | S | 1 | H |
| 3-97 | 1-propyl-2-methyl-imidazo[4,5-b]pyridine | S | 5 | H |
| 3-98 | 1,2-dimethyl-imidazo[4,5-b]pyridine | O | 3 | H |
| 3-99 | 1,2-dimethyl-imidazo[4,5-b]pyridine | O | 4 | MeO |
| 3-100 | 1,2-dimethyl-imidazo[4,5-b]pyridine | O | 5 | Cl |
| 3-101 | 1-methyl-pyrrolo[2,3-c]pyridine | O | 2 | H |

TABLE 3-continued

| Cpd. No. | X | Y | m | R |
|---|---|---|---|---|
| 3-102 | 1-methyl-2-methyl-pyrrolo[2,3-c]pyridine | O | 1 | H |
| 3-103 | 1-methyl-2-methyl-pyrrolo[2,3-c]pyridine | O | 2 | H |
| 3-104 | 1-methyl-imidazo[4,5-c]pyridine | O | 2 | H |
| 3-105 | 1-methyl-imidazo[4,5-c]pyridine | O | 4 | H |
| 3-106 | 2-methyl-imidazo[1,2-a]pyridine | O | 1 | H |
| 3-107 | 5-methyl-2-methyl-imidazo[1,2-a]pyridine | O | 2 | H |
| 3-108 | 6,8-dibromo-2-methyl-imidazo[1,2-a]pyridine | O | 3 | H |
| 3-109 | 2-methyl-imidazo[1,2-a]pyridine | S | 1 | H |
| 3-110 | 8-hydroxy-2-methyl-imidazo[1,2-a]pyridine | O | 1 | H |
| 3-111 | 6-chloro-2-methyl-imidazo[1,2-a]pyridine | O | 1 | H |

TABLE 3-continued
| Cpd. No. | X | Y | m | R |
|---|---|---|---|---|
| 3-112 | 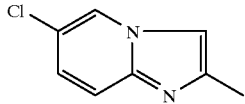 | O | 2 | H |
| 3-113 | 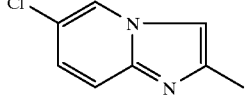 | S | 1 | H |
| 3-114 | 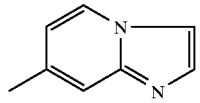 | O | 1 | H |
| 3-115 | 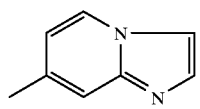 | O | 3 | H |
| 3-116 | 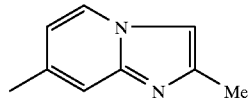 | O | 1 | H |
| 3-117 | 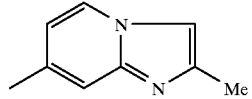 | S | 2 | H |
| 3-118 | 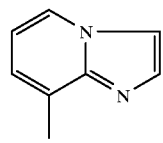 | O | 1 | H |
| 3-119 | 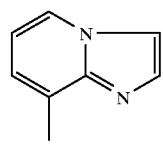 | O | 5 | Me |
| 3-120 | 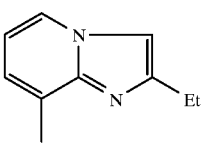 | O | 1 | MeO |

TABLE 4

| Cpd. No. | X | Y | m | R |
|---|---|---|---|---|
| 4-1 | N-methylindole | O | 2 | H |
| 4-2 | 3-methylindole (NH) | O | 2 | H |
| 4-3 | 3-CPh₃, N-methylindole | O | 2 | H |
| 4-4 | 3-methyl-N-methylindole | O | 2 | H |
| 4-5 | 2-methylindole (NH) | O | 1 | H |
| 4-6 | 2-methyl-N-methylindole | O | 1 | H |
| 4-7 | 2-methyl-N-methylindole | O | 2 | H |
| 4-8 | 2-methyl-N-ethylindole | O | 1 | H |
| 4-9 | 3-methyl-N-(3-PhPr)indole | O | 3 | H |
| 4-10 | 5-MeO, 3-methyl, 2-Me, N-Me indole | O | 1 | H |
| 4-11 | 5-HO, 3-methyl, N-Me indole | O | 5 | Me |
| 4-12 | 3-methyl-N-iPr indole | S | 1 | H |
| 4-13 | 3-methyl-2-Et-N-Me indole | O | 2 | MeO |
| 4-14 | 5-MeO, 3-methyl, N-Me indole | O | 1 | H |
| 4-15 | 5-HO, 3-methyl, 2-Me, N-Me indole | O | 1 | H |
| 4-16 | 5-BuO, 3-methyl, N-Me indole | O | 1 | H |
| 4-17 | 4-Me, 7-Me, 3-methyl, N-Me indole | S | 4 | Cl |

TABLE 4-continued

| Cpd. No. | X | Y | m | R |
|---|---|---|---|---|
| 4-18 | 3-Me, 6-Me, N-iBu indole | O | 3 | OH |
| 4-19 | 5-Br, 6-Cl, 3-Me, N-Me indole | S | 2 | Bu |
| 4-20 | 5-Br, 3-Me, N-H indole | O | 5 | H |
| 4-21 | 5-HO, 3-Me, N-iBu indole | O | 1 | H |
| 4-22 | 5-F, 2-Me, N-Me indole | O | 1 | H |
| 4-23 | 5-Cl, 2-Me, N-Me indole | O | 1 | H |
| 4-24 | 5-HO, 2-Me, N-Me indole | O | 1 | H |
| 4-25 | 5-MeO, 2-Me, N-Me indole | O | 1 | H |
| 4-26 | 5-Br, 2-Me, N-Me indole | O | 1 | H |
| 4-27 | 5-NO$_2$, 2-Me, N-Et indole | O | 1 | H |
| 4-28 | 5-Me, 2-Me, N-Me indole | O | 1 | H |
| 4-29 | 5-NH$_2$, 2-Me, N-Me indole | O | 1 | H |
| 4-30 | 5-AcNH, 2-Me, N-Me indole | O | 1 | H |
| 4-31 | 5-(N-Et, N-benzoyl)amino, 2-Me, N-Et indole | O | 1 | H |
| 4-32 | 5-BzNH, 2-Me, N-Me indole | O | 1 | H |
| 4-33 | 5-BuNH, 2-Me, N-Me indole | O | 1 | H |
| 4-34 | 5-(N-Me, N-Bz)amino, 2-Me, N-Me indole | O | 1 | H |

TABLE 4-continued

| Cpd. No. | X | Y | m | R |
|---|---|---|---|---|
| 4-35 | Ph-NH-[5-indolyl, N-Me, 2-Me] | O | 1 | H |
| 4-36 | AcNH-[5-indolyl, NH, 2-Me] | S | 2 | Me |
| 4-37 | PhC(O)NH-[5-indolyl, N-Bu, 2-Me] | O | 4 | MeO |
| 4-38 | 4-Cl-[indolyl, N-Me, 2-Me] | O | 1 | H |
| 4-39 | 3-OMe-[indolyl, N-Me, 2-Me] | O | 1 | H |
| 4-40 | 6-F-[indolyl, N-Me, 2-Me] | O | 1 | H |
| 4-41 | 6-Cl-[indolyl, N-Et, 2-Me] | O | 2 | Cl |
| 4-42 | 6-MeO-[indolyl, N-Me, 2-Me] | O | 1 | H |
| 4-43 | 5,6-diMeO-[indolyl, N-Me, 2-Me] | O | 4 | H |
| 4-44 | 7-MeO-[indolyl, N-Bz, 2-Me] | S | 1 | H |
| 4-45 | 5-Me-[indolyl, NH] | O | 1 | H |
| 4-46 | 5-Me-[indolyl, N-Me] | O | 1 | H |
| 4-47 | 5-Me-[indolyl, N-Bu] | O | 2 | H |
| 4-48 | 5-Me-[indolyl, N-Et] | S | 1 | Me |
| 4-49 | 5-Me-[indolyl, N-Me] | O | 4 | Me |
| 4-50 | 4-Me-[indolyl, NH] | O | 1 | H |

TABLE 4-continued

| Cpd. No. | X | Y | m | R |
|---|---|---|---|---|
| 4-51 | 4-methyl-1-Me-indole | O | 1 | H |
| 4-52 | 4-methyl-1-Me-indole | O | 2 | H |
| 4-53 | 4-methyl-1-iPr-indole | O | 2 | Me |
| 4-54 | 4-methyl-1-Bu-indole | S | 3 | H |
| 4-55 | 4-methyl-1-Me-indole | O | 1 | MeO |
| 4-56 | 4-methyl-1-Bz-indole | S | 2 | H |
| 4-57 | 1-Me-indoline | O | 2 | H |
| 4-58 | 5-MeO-1-Me-indoline | O | 4 | Me |
| 4-59 | 2-methylindoline (N-H) | O | 1 | H |
| 4-60 | 2-methylindoline (N-H) | O | 2 | H |
| 4-61 | 2-methylindoline (N-H) | S | 3 | H |
| 4-62 | 1,2-dimethylindoline | O | 1 | H |
| 4-63 | 1,2-dimethylindoline | O | 2 | H |
| 4-64 | 1,2-dimethylindoline | O | 3 | H |
| 4-65 | 1,2-dimethylindoline | S | 1 | Bu |
| 4-66 | 1-Et-2-methylindoline | O | 1 | H |

TABLE 4-continued

| Cpd. No. | X | Y | m | R |
|---|---|---|---|---|
| 4-67 | indoline, N-Pr, 2-methyl | O | 2 | MeO |
| 4-68 | indoline, N-Bu, 2-methyl | O | 1 | H |
| 4-69 | indoline, N-Me, 2-methyl | S | 5 | H |
| 4-70 | indoline, N-Me, 2-methyl | O | 1 | Cl |
| 4-71 | indoline, N-iPr, 2-methyl | O | 1 | H |
| 4-72 | 7-azaindole, N-Me | O | 2 | H |
| 4-73 | 7-azaindole, N-Me | S | 3 | H |
| 4-74 | 7-azaindole, N-Me | O | 4 | H |
| 4-75 | 7-azaindole, 3-methyl, N-H | O | 1 | H |

TABLE 4-continued

| Cpd. No. | X | Y | m | R |
|---|---|---|---|---|
| 4-76 | 7-azaindole, 3-methyl, N-H | O | 3 | H |
| 4-77 | 7-azaindole, 3-methyl, N-Me | O | 1 | H |
| 4-78 | 7-azaindole, 3-methyl, N-Me | O | 2 | H |
| 4-79 | 7-azaindole, 3-methyl, N-Me | S | 3 | Me |
| 4-80 | 7-azaindole, 3-methyl, N-iPr | O | 2 | Cl |
| 4-81 | 7-azaindole, 2-methyl, N-Me | O | 1 | H |
| 4-82 | 7-azaindole, 2-methyl, N-Me | O | 2 | H |
| 4-83 | 7-azaindoline, 2-methyl, N-H | O | 1 | Et |
| 4-84 | 7-azaindoline, 2-methyl, N-Me | S | 1 | H |

TABLE 4-continued
| Cpd. No. | X | Y | m | R |
|---|---|---|---|---|
| 4-85 | 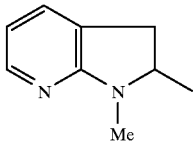 | O | 2 | H |
| 4-86 | 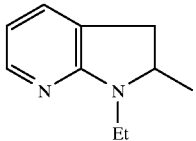 | O | 1 | H |
| 4-87 | 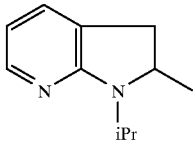 | O | 1 | Me |
| 4-88 | 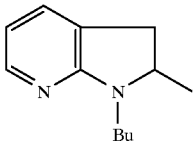 | S | 4 | H |
| 4-89 | 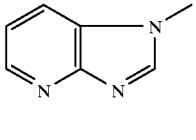 | O | 2 | H |
| 4-90 | 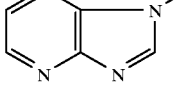 | S | 3 | H |
| 4-91 | 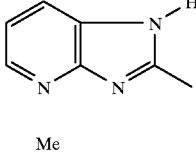 | O | 1 | H |
| 4-92 | 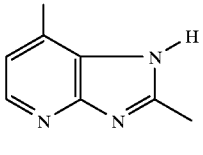 | O | 2 | H |
| 4-93 | 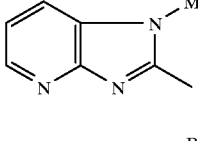 | O | 1 | H |
| 4-94 | 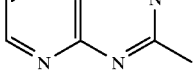 | O | 2 | H |
| 4-95 | 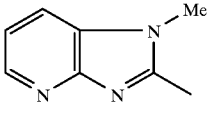 | O | 1 | Me |
| 4-96 | 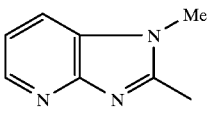 | S | 1 | H |
| 4-97 | 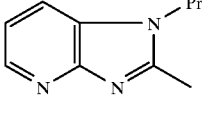 | S | 5 | H |
| 4-98 | 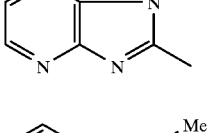 | O | 3 | H |
| 4-99 | 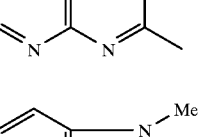 | O | 4 | MeO |
| 4-100 | 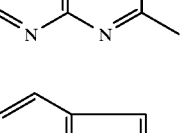 | O | 1 | H |
| 4-101 | 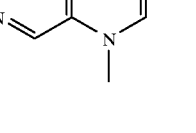 | O | 2 | H |
| 4-102 | 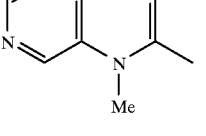 | O | 1 | H |
| 4-103 | 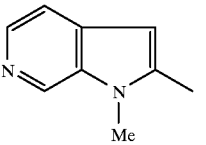 | O | 2 | H |
| 4-104 | 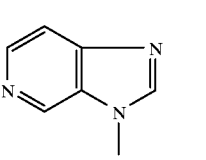 | O | 2 | H |

TABLE 4-continued

| Cpd. No. | X | Y | m | R |
|---|---|---|---|---|
| 4-105 | (imidazo-pyridine with N-Me) | S | 4 | H |
| 4-106 | (2-methylimidazo[1,2-a]pyridine) | O | 1 | H |
| 4-107 | (2-methylimidazo[1,2-a]pyridine) | O | 2 | H |
| 4-108 | (6,8-dibromo-2-methylimidazo[1,2-a]pyridine) | O | 3 | H |
| 4-109 | (2-methylimidazo[1,2-a]pyridine) | S | 1 | H |
| 4-110 | (8-hydroxy-2-methylimidazo[1,2-a]pyridine) | O | 1 | H |
| 4-111 | (6-chloro-2-methylimidazo[1,2-a]pyridine) | O | 1 | H |
| 4-112 | (6-chloro-2-methylimidazo[1,2-a]pyridine) | O | 2 | H |
| 4-113 | (6-chloro-2-methylimidazo[1,2-a]pyridine) | S | 1 | H |
| 4-114 | (7-methylimidazo[1,2-a]pyridine) | O | 1 | H |
| 4-115 | (7-methylimidazo[1,2-a]pyridine) | O | 3 | H |
| 4-116 | (7-methyl-2-methylimidazo[1,2-a]pyridine) | O | 1 | H |
| 4-117 | (5,7-dimethyl-2-methylimidazo[1,2-a]pyridine) | S | 2 | H |
| 4-118 | (8-methylimidazo[1,2-a]pyridine) | O | 1 | H |
| 4-119 | (5,8-dimethylimidazo[1,2-a]pyridine) | O | 5 | Me |
| 4-120 | (8-methyl-2-ethylimidazo[1,2-a]pyridine) | O | 1 | MeO |

TABLE 5
| Cpd. No. | X | Y | m | R |
|---|---|---|---|---|
| 5-1 | 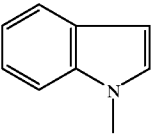 | O | 2 | H |
| 5-2 | 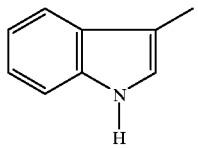 | O | 2 | H |
| 5-3 | 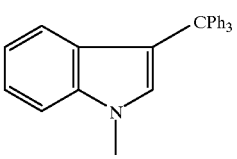 | O | 2 | H |
| 5-4 | 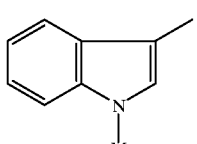 | O | 2 | H |
| 5-5 | 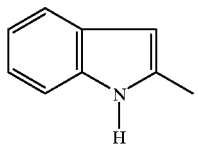 | O | 1 | H |
| 5-6 | 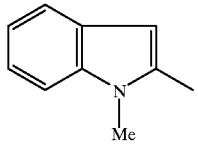 | O | 1 | H |
| 5-7 | 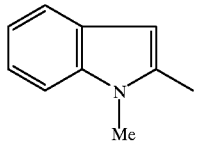 | O | 2 | H |
| 5-8 | 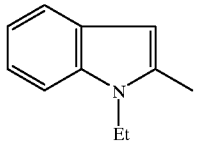 | O | 1 | H |
| 5-9 | 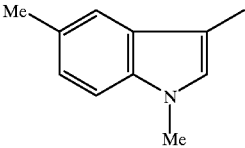 | O | 3 | H |

TABLE 5-continued

| Cpd. No. | X | Y | m | R |
|---|---|---|---|---|
| 5-10 | 5-methoxy-1,2-dimethyl-3-indolyl | O | 1 | H |
| 5-11 | 5-hydroxy-1-methyl-3-indolyl | O | 5 | Me |
| 5-12 | 1-isopropyl-3-indolyl | S | 1 | H |
| 5-13 | 2-ethyl-1-methyl-3-indolyl | O | 2 | MeO |
| 5-14 | 5-methoxy-1-methyl-3-indolyl | O | 1 | H |
| 5-15 | 5-hydroxy-1,2-dimethyl-3-indolyl | O | 1 | H |
| 5-16 | 5-butoxy-1-methyl-3-indolyl | O | 1 | H |
| 5-17 | 1,4,7-trimethyl-3-indolyl | S | 4 | Cl |

TABLE 5-continued
| Cpd. No. | X | Y | m | R |
|---|---|---|---|---|
| 5-18 | 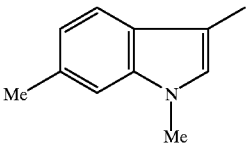 | O | 3 | OH |
| 5-19 | 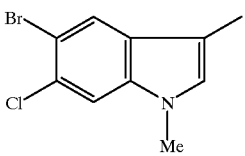 | S | 2 | Bu |
| 5-20 | 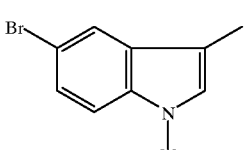 | O | 5 | H |
| 5-21 | 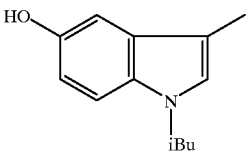 | O | 1 | H |
| 5-22 | 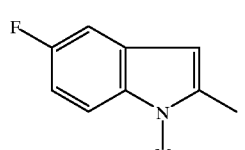 | O | 1 | H |
| 5-23 | 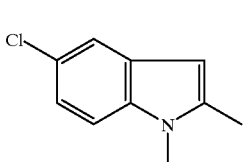 | O | 1 | H |
| 5-24 | 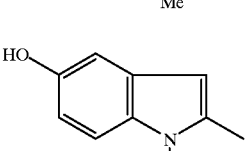 | O | 1 | H |
| 5-25 | 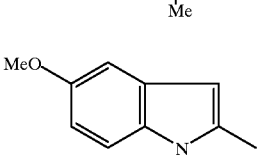 | O | 1 | H |
| 5-26 | 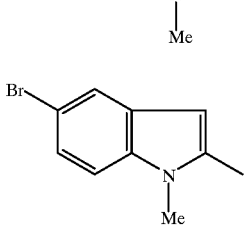 | O | 1 | H |

TABLE 5-continued

| Cpd. No. | X | Y | m | R |
|---|---|---|---|---|
| 5-27 | 5-nitro-1-ethyl-2-methylindole | O | 1 | H |
| 5-28 | 5-methyl-1,2-dimethylindole | O | 1 | H |
| 5-29 | 5-amino-1,2-dimethylindole | O | 1 | H |
| 5-30 | 5-(N-acetyl-N-benzoylamino)-1,2-dimethylindole | O | 1 | H |
| 5-31 | 5-(benzoylamino)-1-ethyl-2-methylindole | O | 1 | H |
| 5-32 | 5-(N-methyl-N-pyrimidinylamino)-1,2-dimethylindole | O | 1 | H |
| 5-33 | 5-(butylamino)-1,2-dimethylindole | O | 1 | H |
| 5-34 | 5-(N-benzoyl-N-methylamino)-1,2-dimethylindole | O | 1 | H |

TABLE 5-continued

| Cpd. No. | X | Y | m | R |
|---|---|---|---|---|
| 5-35 | 5-(PhNH)-1-methyl-2-methylindole | O | 1 | H |
| 5-36 | 5-(AcNH)-2-methylindole (NH) | S | 2 | Me |
| 5-37 | 5-(PhC(O)NH)-1-butyl-2-methylindole | O | 4 | MeO |
| 5-38 | 4-chloro-1-isopropyl-2-methylindole | O | 1 | H |
| 5-39 | 3-methoxy-1-methyl-2-methylindole | O | 1 | H |
| 5-40 | 6-fluoro-1-methyl-2-methylindole | O | 1 | H |
| 5-41 | 6-chloro-1-ethyl-2-methylindole | O | 2 | Cl |
| 5-42 | 6-methoxy-1-methyl-2-methylindole | O | 1 | H |

TABLE 5-continued
| Cpd. No. | X | Y | m | R |
|---|---|---|---|---|
| 5-43 | 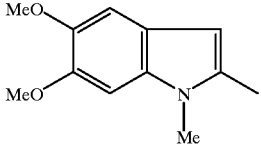 | O | 4 | H |
| 5-44 | 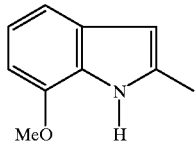 | S | 1 | H |
| 5-45 | 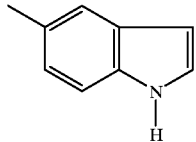 | O | 1 | H |
| 5-46 | 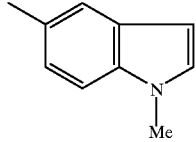 | O | 1 | H |
| 5-47 | 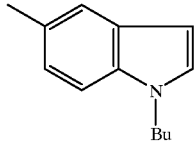 | O | 2 | H |
| 5-48 | 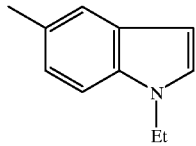 | S | 1 | Me |
| 5-49 | 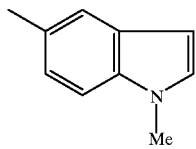 | O | 4 | Me |
| 5-50 | 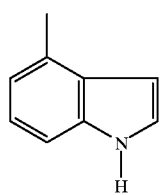 | O | 1 | H |

TABLE 5-continued

| Cpd. No. | X | Y | m | R |
|---|---|---|---|---|
| 5-51 | 4-methyl-1-methylindole | O | 1 | H |
| 5-52 | 4-methyl-1-methylindole | O | 2 | H |
| 5-53 | 4-methyl-1-isopropylindole | O | 2 | Me |
| 5-54 | 4-methyl-7-AcNH-1-butylindole | S | 3 | H |
| 5-55 | 4-methyl-1-methylindole | O | 1 | MeO |
| 5-56 | 4-methyl-7-nitro-1-methylindole | S | 1 | H |
| 5-57 | 1-methylindoline | O | 2 | H |

TABLE 5-continued

| Cpd. No. | X | Y | m | R |
|---|---|---|---|---|
| 5-58 | 5-methoxy-1-methylindoline | O | 4 | Me |
| 5-59 | 2-methylindoline (N-H) | O | 1 | H |
| 5-60 | 2-methylindoline (N-H) | O | 2 | H |
| 5-61 | 2-methylindoline (N-H) | S | 3 | H |
| 5-62 | 1,2-dimethylindoline | O | 1 | H |
| 5-63 | 1,2-dimethylindoline | O | 2 | H |
| 5-64 | 1,2-dimethylindoline | O | 3 | H |
| 5-65 | 1,2-dimethylindoline | S | 1 | H |
| 5-66 | 1-ethyl-2-methylindoline | O | 1 | H |

TABLE 5-continued

| Cpd. No. | X | Y | m | R |
|---|---|---|---|---|
| 5-67 | 2-methyl-1-propyl-indoline | O | 2 | MeO |
| 5-68 | 1-butyl-2-methyl-indoline | O | 1 | H |
| 5-69 | 2-methyl-1-methyl-indoline | S | 5 | H |
| 5-70 | 5-(BzNH)-1,2-dimethyl-indoline | S | 1 | Cl |
| 5-71 | 1-isopropyl-2-methyl-indoline | O | 1 | H |
| 5-72 | 1-methyl-7-azaindole | O | 2 | H |
| 5-73 | 1-methyl-7-azaindole | S | 3 | H |
| 5-74 | 1-methyl-7-azaindole | O | 4 | H |
| 5-75 | 3-methyl-7-azaindole | O | 1 | H |

TABLE 5-continued

| Cpd. No. | X | Y | m | R |
|---|---|---|---|---|
| 5-76 | 3-methyl-7-azaindole (NH) | O | 3 | H |
| 5-77 | 3-methyl-1-methyl-7-azaindole | O | 1 | H |
| 5-78 | 3-methyl-1-methyl-7-azaindole | O | 2 | H |
| 5-79 | 3-methyl-1-methyl-7-azaindole | S | 3 | Me |
| 5-80 | 3-methyl-1-iPr-7-azaindole | O | 2 | Cl |
| 5-81 | 3-methyl-1-methyl-7-azaindole | O | 1 | H |
| 5-82 | 3-methyl-1-methyl-7-azaindole | O | 2 | H |
| 5-83 | 2-methyl-2,3-dihydro-7-azaindole (NH) | O | 1 | H |
| 5-84 | 3-iBu-2-methyl-1-methyl-2,3-dihydro-7-azaindole | S | 1 | H |

TABLE 5-continued
| Cpd. No. | X | Y | m | R |
|---|---|---|---|---|
| 5-85 | 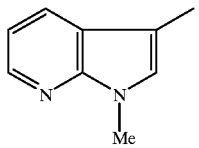 | O | 2 | H |
| 5-86 | 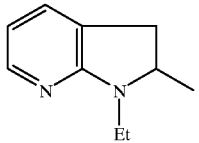 | O | 1 | H |
| 5-87 | 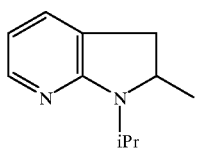 | O | 1 | Me |
| 5-88 | 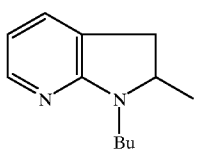 | S | 4 | H |
| 5-89 | 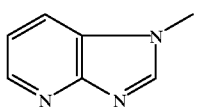 | O | 2 | H |
| 5-90 | 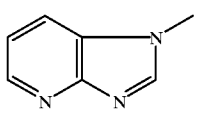 | S | 3 | H |
| 5-91 | 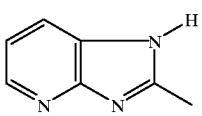 | O | 1 | H |
| 5-92 | 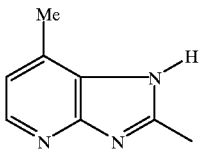 | O | 2 | H |
| 5-93 | 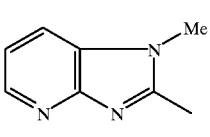 | O | 1 | H |
| 5-94 | 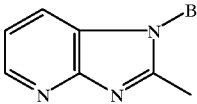 | O | 1 | H |

TABLE 5-continued

| Cpd. No. | X | Y | m | R |
|---|---|---|---|---|
| 5-95 | imidazo[4,5-b]pyridine, 1-Me, 2-Me | O | 1 | Me |
| 5-96 | imidazo[4,5-b]pyridine, 1-Me, 2-Me | S | 1 | H |
| 5-97 | imidazo[4,5-b]pyridine, 1-Pr, 2-Me | S | 5 | H |
| 5-98 | imidazo[4,5-b]pyridine, 1-Me, 2-Me | O | 3 | H |
| 5-99 | imidazo[4,5-b]pyridine, 1-Me, 2-Me | O | 4 | MeO |
| 5-100 | imidazo[4,5-b]pyridine, 1-Me, 2-Me | O | 1 | H |
| 5-101 | pyrrolo[2,3-c]pyridine, N-Me | O | 2 | H |
| 5-102 | pyrrolo[2,3-c]pyridine, N-Me, 2-Me | O | 1 | H |
| 5-103 | pyrrolo[2,3-c]pyridine, N-Me, 2-Me | O | 3 | H |
| 5-104 | imidazo[4,5-c]pyridine, N-Me | O | 2 | H |

TABLE 5-continued
| Cpd. No. | X | Y | m | R |
|---|---|---|---|---|
| 5-105 | 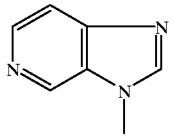 | O | 4 | H |
| 5-106 | 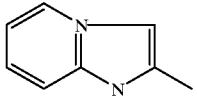 | O | 1 | H |
| 5-107 | 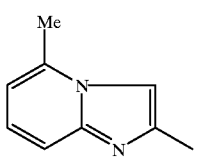 | O | 2 | H |
| 5-108 | 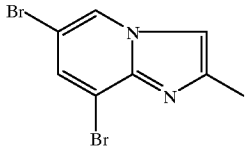 | O | 3 | H |
| 5-109 | 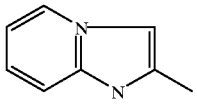 | S | 1 | H |
| 5-110 | 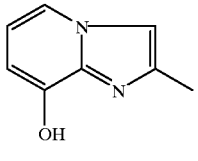 | O | 1 | H |
| 5-111 | 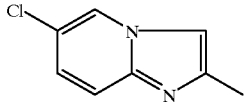 | O | 1 | H |
| 5-112 | 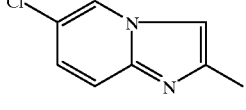 | O | 2 | H |
| 5-113 | 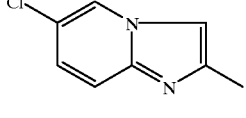 | S | 1 | H |
| 5-114 | 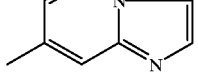 | O | 1 | H |

TABLE 5-continued

| Cpd. No. | X | Y | m | R |
|---|---|---|---|---|
| 5-115 | 7-methylimidazo[1,2-a]pyridine | O | 3 | H |
| 5-116 | 7-methyl-2-methylimidazo[1,2-a]pyridine | O | 1 | H |
| 5-117 | 7-methyl-2-methylimidazo[1,2-a]pyridine | S | 2 | H |
| 5-118 | 8-methylimidazo[1,2-a]pyridine | O | 1 | H |
| 5-119 | 8-methyl-3-methylimidazo[1,2-a]pyridine | O | 5 | Me |
| 5-120 | 8-methyl-2-ethylimidazo[1,2-a]pyridine | O | 1 | MeO |

Of the compounds listed above, we particularly prefer the following, that is to say Compounds No. 1-1, 1-2, 1-3, 1-6, 1-57, 1-59, 1-62, 1-72, 1-81, 1-91, 1-93, 1-106, 1-121, 1-122, 1-125, 1-130, 1-134, 1-135, 1-137, 1-140, 1-142, 1-153, 1-156, 1-158, 1-161, 1-177, 1-179, 1-180, 1-182, 1-183, 1-207, 1-218 and 2-100, of which Compounds No. 1-1, 1-57, 1-62, 1-91, 1-93, 1-106, 1-122, 1-125, 1-130, 1-134, 1-137, 1-140, 1-142, 1-153, 1-156, 1-177, 1-179, 1-180, 1-182, 1-183, 1-207, 1-218 and 2-100 are more preferred. Still more preferred compounds are Compounds No. 1-62, 1-93, 1-125, 1-134, 1-140, 1-142, 1-153, 1-177, 1-179, 1-182, 1-183 and 1-207.

The most preferred compounds are Compounds No.:
1-93. 5-{4-(3-methylimidazo[5,4-b]pyridin-2-ylmethoxy) benzyl}thiazolidine-2,4-dione;
1-125. 5-{4-(5-Chloro-3-methylimidazo[5,4-b]pyridin-2-ylmethoxy)benzyl}thiazolidine-2,4-dione;
1-142. 5-{4-(5-Methoxy-3-methylimidazo[5,4-b]pyridin-2-ylmethoxy)benzyl}thiazolidine-2,4-dione;
1-153. 5-{4-(5-Hydroxy-3-methylimidazo[5,4-b]pyridin-2-ylmethoxy)benzyl}thiazolidine-2,4-dione;
1-182. 5-{4-(5-Ethoxy-3-methylimidazo[5,4-b]pyridin-2-ylmethoxy)benzyl}thiazolidine-2,4-dione;
1-183. 5-{4-(5-Isopropoxy-3-methylimidazo[5,4-b]pyridin-2-ylmethoxy)benzyl}thiazolidine-2,4-dione.

The compounds of the present invention may be prepared by a variety of processes well known in the art for the preparation of compounds of this general type. For example they may be prepared by the following Reaction Schemes A, B, C, D and E:

Reaction Scheme A

This represents a general scheme that may be used to prepare the compounds of the present invention where Z represents a group of formula (i), (ii), (iii) or (iv):

Reaction Scheme A:

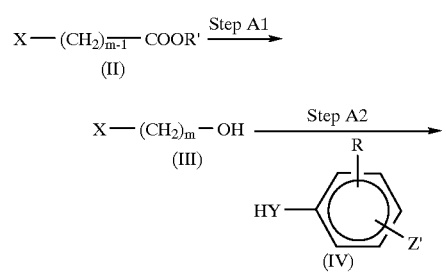

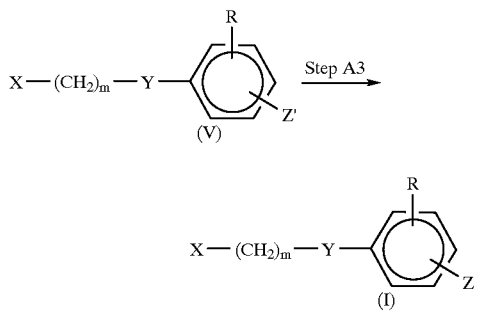

In the above formulae:

X and m are as defined above;

R' represents an alkyl group having from 1 to 5 carbon atoms, which may be a straight or branched chain group, for example any of those groups having from 1 to 5 carbon atoms included in the groups which may be represented by $R^a$ and $R^b$; and Z' represents a group of formula (vi), (vii), (viii) or (ix):

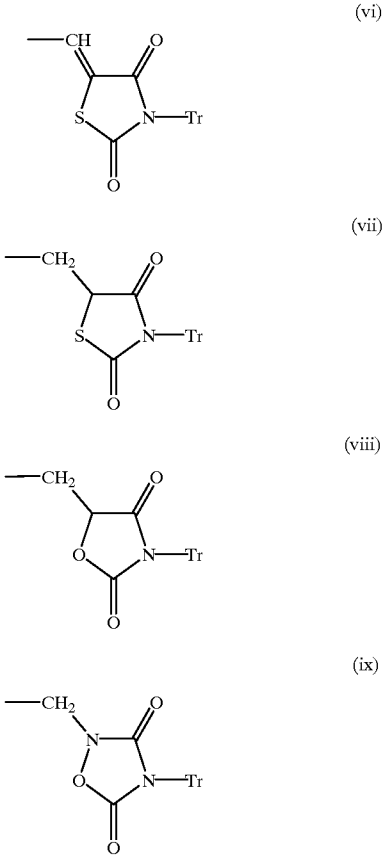

where Tr represents a triphenylmethyl group.

Step A1

In Step A1, a compound of formula (III) is prepared by reducing a compound of formula (II).

The reaction may be carried out using a reducing agent. The nature of the reducing agent employed in this reaction is not critical, and any such agent commonly used in reactions of this type may equally be used here. Examples of such reducing agents include: metal hydrides, such as lithium borohydride, sodium borohydride, sodium cyanoborohydride, lithium aluminum hydride or diisopropylaluminum hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, tetrahydrofuran or dioxane; amides, such as dimethylformamide, dimethylacetamide or hexamethylphosphoric triamide; alcohols, such as methanol, ethanol or isopropanol; and mixtures of any two or more of these solvents.

The reaction can take place over a wide range of temperatures, and the precise reaction temperature is not critical to the invention. In general, we find it convenient to carry out the reaction at a temperature of from that of ice-cooling to heating, e.g. to the reflux temperature of the reaction medium, preferably with ice-cooling or at about room temperature. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

The reaction is preferably carried out in an alcohols or in a mixture of one or more alcohols and other organic solvents in the presence of lithium borohydride at a temperature between room temperature and the reflux temperature of the reaction medium for a period of from 1 hour to 1 day; or in a hydrocarbon or an ether in the presence of lithium aluminum hydride or diisobutylaluminum hydride with cooling or heating for a period of from 1 to 10 hours.

Step A2

In Step A2, a compound of formula (V) is prepared by subjecting a compound of formula (III) and a compound of formula (IV) (in the formula, Y, R and Z' are as defined above) to a Mitsunobu reaction [O. Mitsunobu: Synthesis, 1 (1981)].

The reaction is usually carried out in a solvent in the presence of at least one azo compound and at least one phosphine.

There is no particular restriction on the nature of the azo compounds used, and any azo compounds commonly used in this type of reaction may equally be employed here used. Examples of such azo compounds include diethyl azodicarboxylate and 1,1'-(azodicarbonyl)-dipiperidine. There is likewise no particular restriction on the nature of the phosphines used, and examples include triphenylphosphine and tributylphosphine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or 1,2-dichloroethane; ethers, such as diethyl ether, tetrahydrofuran or dioxane; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from room temperature to heating, e.g. to the reflux temperature of the reaction mixture, more preferably at a temperature of from room temperature to 60° C. The time required for the reaction may also vary widely, depending on many factors, notably the reaction temperature and the nature of the reagents and solvent employed. However, provided that the reaction is effected under the preferred conditions outlined above, a period of from several hours to several days, more preferably from 5 hours to 3 days will usually suffice.

Step A3

In Step A3, a compound of formula (I) is prepared. This may be any of the compounds of the present invention except those in which Z represents a group of the formula (v).

The reaction is effected by reacting a compound of formula (V) with an acid, such as trifluoroacetic acid, trifluoromethanesulfonic acid, acetic acid, hydrochloric acid or sulfuric acid in the presence or absence of a solvent.

Where a solvent is used, there is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; esters, such as ethyl acetate or methyl acetate; water; and mixtures of any two or more of these solvents.

The reaction can take place over a wide range of temperatures, and the precise reaction temperature is not critical to the invention. In general, we find it convenient to carry out the reaction at a temperature of from ice-cooling to room temperature. The time required for the reaction may also vary widely, depending on many factors, notably the reaction temperature and the nature of the reagents and solvent employed. However, provided that the reaction is effected under the preferred conditions outlined above, a period of from several tens of minutes to several tens of hours, more preferably from 0.5 to 10 hours, will usually suffice.

This step can also be achieved by catalytic hydrogenation of a compound of formula (V). There is no particular restriction on the nature of the catalysts used, and any hydrogenation catalysts commonly used in this type of reaction may equally be employed here. Examples of such hydrogenation catalysts include palladium-on-charcoal, palladium black, platinum oxide and platinum black, of which we prefer palladium-on-charcoal.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; alcohols, such as methanol, ethanol or isopropanol; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from room temperature to heating, e.g. at the reflux temperature of the reaction mixture, preferably at room temperature or with heating. The time required for the reaction may also vary widely, depending on many factors, notably the reaction temperature and the nature of the reagents and solvent employed. However, provided that the reaction is effected under the preferred conditions outlined above, a period of from several hours to several days, more preferably from 1 hour to 1 day will usually suffice.

Reaction Scheme B

This is a process which may be used to prepare compounds of formula (I) in which Y represents an oxygen atom and Z represents a group of formula (i) or (ii), that is a 2,4-dioxothiazolidin-5-ylidenylmethyl or 2,4-dioxothiazolidin-5-ylmethyl group, i.e. compounds of formulae (VII) and (VIII), respectively.

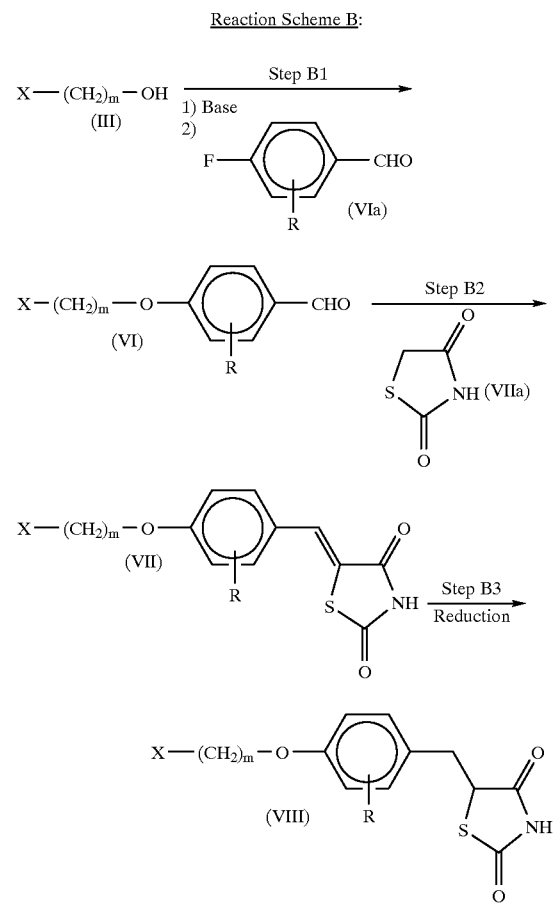

Step B1

In Step B1, a compound of formula (VI) is prepared by treating a compound of formula (III) with a base (the first stage) and then by reacting the resulting product with a p-fluorobenzaldehyde derivative of formula (VIa), such as 2-methoxy--4-fluorobenzaldehyde or 3-methyl-4-fluorobenzaldehyde (the second stage).

There is no particular restriction on the nature of the base used in the first stage, and any base commonly used in this type of reaction may equally be employed here. An example of such a base is sodium hydride.

The reaction in the first stage is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, tetrahydrofuran or dioxane; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to one day, more preferably from 1 to 10 hours, will usually suffice.

After completion of the first stage reaction, the second stage can be carried out by adding a p-fluorobenzaldehyde derivative of formula (VIa) to the reaction mixture and then by allowing the mixture to react.

The reaction of the second stage can take place over a wide range of temperatures, and the precise reaction temperature is not critical to the invention. In general, we find it convenient to carry out the reaction at a temperature of from room temperature to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to several days will usually suffice.

Step B2

In Step B2, a compound of formula (VII) is prepared by reacting a compound of formula (VI) with thiazolidine-2,4-dione of formula (VIIa).

The reaction may be carried out in the presence or absence of a catalyst. Where the reaction is carried out in the presence of a catalyst, there is no particular restriction on the nature of the catalyst used, and any catalyst commonly used in this type of reaction may equally be employed here. Examples of such catalysts include sodium acetate, piperidinium acetate and piperidinium benzoate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, tetrahydrofuran or dioxane; alcohols, such as methanol, ethanol or isopropanol; amides, such as dimethylformamide, dimethylacetamide or hexamethylphosphoric triamide; halogenated hydrocarbons, such as methylene chloride, chloroform or 1,2-dichloroethane; nitrites, such as acetonitrile or propionitrile; esters, such as ethyl formate or ethyl acetate; and mixtures of any two or more of these solvents.

The reaction can take place over a wide range of temperatures, and the precise reaction temperature is not critical to the invention. In general, we find it convenient to carry out the reaction with heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 1 to 50 hours will usually suffice.

Step B3

In Step B3, a compound of formula (VIII) is prepared by reducing a compound of formula (VII) by means of catalytic hydrogenation. There is no particular restriction on the nature of the catalysts used, and any hydrogenation catalysts commonly used in this type of reaction may equally be employed here. Examples of such hydrogenation catalysts include palladium-on-charcoal and palladium black, preferably palladium-on-charcoal.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, dioxane or tetrahydrofuran; alcohols, such as methanol, ethanol or isopropanol; organic acids, such as formic acid, acetic acid or propionic acid; amides such dimethylformamide, dimethylacetamide or hexamethylphosphoric triamide; and mixtures of any two or more of these solvents.

The reaction is normally carried out at atmospheric pressure or under superatmospheric pressure; preferably under superatmospheric pressure.

The reaction can take place over a wide range of temperatures, and the precise reaction temperature is not critical to the invention. In general, we find it convenient to carry out the reaction at a temperature of from room temperature or with heating, e.g. to the reflux temperature of the reaction mixture. The time required for the reaction may also vary widely, depending on many factors, notably the reaction pressure and temperature and the nature of the reagents and solvent employed. However, provided that the reaction is effected under the preferred conditions outlined above, a period of from several hours to several days, more preferably from 1 hour to 1 day, will usually suffice.

This step can also be effected by treating the compound of formula (VII) with a metal hydride according to the procedure disclosed in WO 93/1309A.

Reaction Scheme C

This is a process which may be used to prepare compounds of formula (I) in which Y represents an oxygen atom and Z represents a group of formula (iv) or (v), that is a 3,5-dioxooxadiazolidin-2-ylmethyl or N-hydroxyureidomethyl group, i.e. compounds of formulae (X) and (XI), respectively.

Reaction Scheme C:

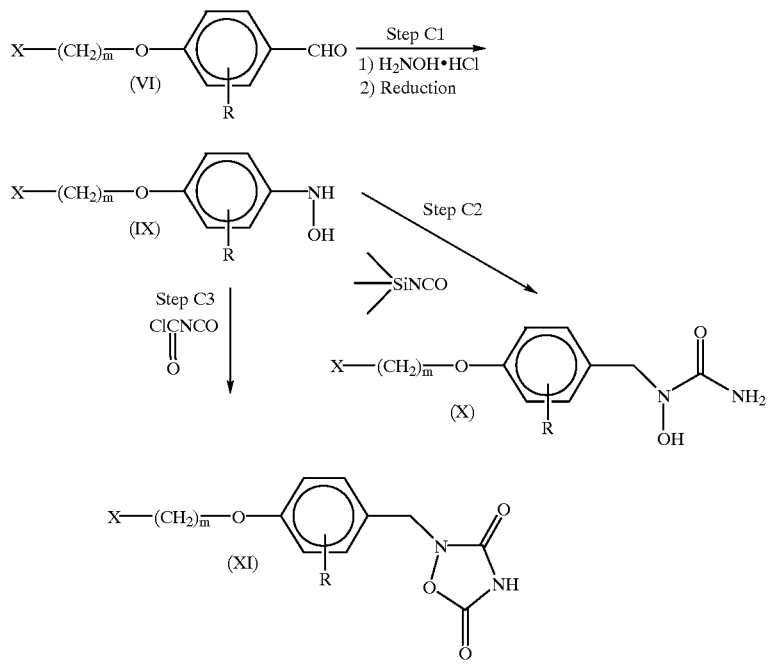

In the above formulae, X, R and m are as defined above.

Step C1

In Step C1, a compound of formula (IX) is prepared by reacting a compound of formula (VI) (which may have been prepared as described in Reaction Scheme B) with hydroxylamine (preferably as the hydrochloride), in a first stage, followed, in a second stage, by reducing the product.

The reaction of the compound of formula (VI) with hydroxylamine (hydrochloride) is, in general, preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, dioxane or tetrahydrofuran; alcohols, such as methanol, ethanol or isopropanol; amides, such as dimethylformamide, dimethylacetamide or hexamethylphosphoric triamide; halogenated hydrocarbons, such as methylene chloride, chloroform or 1,2-dichloroethane; nitriles, such as acetonitrile or propionitrile; esters, such as ethyl formate or ethyl acetate; amines, such as pyridine, triethylamine or N,N-diisopropyl-N-ethylamine; and mixtures of any two or more of these solvents.

The reaction can take place over a wide range of temperatures, and the precise reaction temperature is not critical to the invention. In general, we find it convenient to carry out the reaction at a temperature of from room temperature to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several hours to several tens of hours will usually suffice.

The subsequent reduction in the second stage of this step may be carried out by hydrogenation in the presence of a reducing agent. There is no particular restriction on the nature of the reducing agent used, and any reducing agent commonly used in this type of reaction may equally be employed here. Examples of such reducing agents include metal hydrides, such as lithium aluminum hydride, diisobutylaluminum hydride, lithium borohydride, sodium borohydride or sodium cyanoborohydride.

The second stage reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, dioxane or tetrahydrofuran; amides, such as dimethylformamide, dimethylacetamide or hexamethylphosphoric triamide; alcohols, such as methanol, ethanol or isopropanol; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction-is effected under the preferred conditions outlined above, a period of from several tens of minutes to one day, more preferably from 1 to 10 hours, will usually suffice.

Step C2

In Step C2, a compound of formula (X) is prepared by reacting a compound of formula (IX) with trimethylsilyl isocyanate.

181

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, dioxane or tetrahydrofuran; amides, such as dimethylformamide, dimethylacetamide or hexamethylphosphoric triamide; halogenated hydrocarbons, such as methylene chloride, chloroform or 1,2-dichloroethane; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to several days will usually suffice.

The resulting compound of formula (X) is a compound of the present invention.

Step C3

In Step C3, a compound of formula (XI) is prepared by reacting a compound of formula (IX) with N-(chlorocarbonyl) isocyanate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran or dioxane; amides, such as dimethylformamide, dimethylacetamide or hexamethylphosphoric triamide; halogenated hydrocarbons, such as methylene chloride, chloroform or 1,2-dichloroethane; nitriles, such as acetonitrile or propionitrile; esters, such as ethyl formate or ethyl acetate; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to several tens of hours will usually suffice.

Reaction Scheme D

This is a process which may be used to prepare compounds of formula (I) in which Z represents a group of formula (ii) or (iii), that is a 2,4-dioxothiazolidin-5-ylmethyl or 2,4-dioxooxazolidin-5-ylmethyl group, i.e. compounds of formula (XV).

182

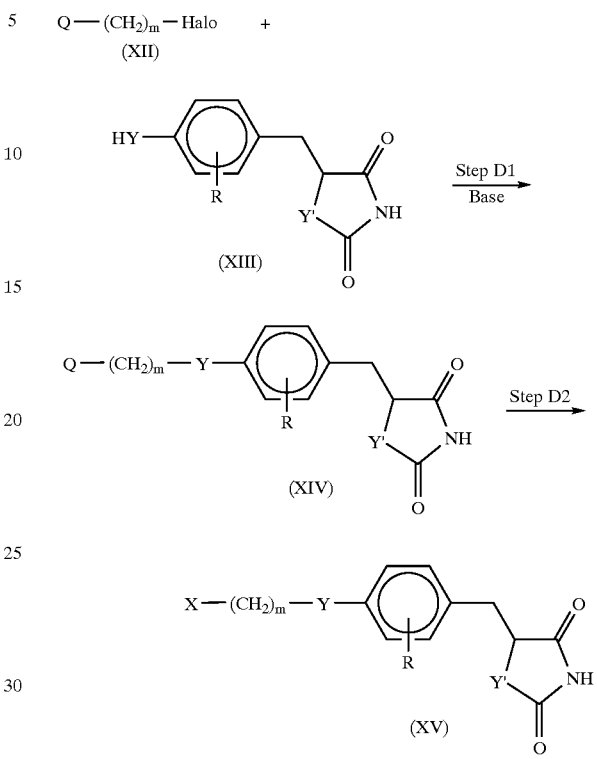

Reaction Scheme D:

In the above formulae:
X is as defined above, but preferably represents an imidazopyridyl or imidazopyrimidinyl group;
Y, R and m are as defined above;
Y' represents an oxygen or sulfur atom;
Q represents a lower alkoxycarbonyl group, a formyl group, a protected formyl group, a carboxyl group or a hydroxy group; and
Halo represents a halogen atom.

Step D1

In Step D1, a compound of formula (XIV) is prepared by reacting a compound of formula (XII) with a compound of formula (XIII) in the presence of a base.

There is no particular restriction on the nature of the base used, and any base commonly used in this type of reaction may equally be employed here. Examples of such bases include: inorganic bases, for example hydrides (such as sodium hydride or potassium hydride) and carbonates (such as potassium carbonate or sodium carbonate); and organic bases, such as triethylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran or dioxane; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

The reaction is most preferably carried out with cooling or heating or at room temperature in an amides or a mixture of at least one amide with at least one other organic solvent, in the presence of sodium hydride for a period of from 1 to 10 hours.

The compounds of formula (XIV), which are prepared by this method, are new compounds and are important intermediates for the preparation of the compounds of formula (I) of the present invention. These compounds of formula (XIV) thus also form part of the present invention.

Step D2

In Step D2, a compound of formula (XV) is prepared by one of the following two methods (a) and (b).

Step D2(a)

The compound of formula (XV) can be produced by reacting a compound of formula (XIV), in which Q represents a lower alkoxycarbonyl group, with a 2,3-diaminopyridine derivative or a 4,5-diaminopyrimidine derivative.

Where Q represents a lower alkoxycarbonyl group, this preferably has a total of from 2 to 7 carbon atoms (i.e. the alkoxy part has from 1 to 6 carbon atoms), and may be a straight or branched chain group. Examples of such groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methylpentoxycarbonyl, 3-methylpentoxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups. Of these, we prefer those alkoxycarbonyl groups having from 1 to 4 carbon atoms, preferably the methoxycarbonyl, ethoxycarbonyl, propoxycarbonyl, isopropoxycarbonyl, butoxycarbonyl and isobutoxycarbonyl groups, and most preferably the methoxycarbonyl and ethoxycarbonyl groups.

The reaction is normally and preferably effected in the presence or the absence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, preferably aromatic hydrocarbons, such as benzene, toluene or xylene; ethers, such as diethyl ether, tetrahydrofuran or dioxane; amides, such as dimethylformamide, dimethylacetamide or hexamethylphosphoric triamide; alcohols, such as methanol, ethanol or butanol; acids, such as acetic acid or propionic acid; and mixtures of any two or more of these solvents.

The reaction can take place over a wide range of temperatures, and the precise reaction temperature is not critical to the invention. In general, we find it convenient to carry out the reaction with heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 3 hours to several days will usually suffice.

The reaction is most preferably carried out in the absence of a solvent with heating at a temperature of from 50° C. to 150° C. for a period of from 5 hours to 2 days.

Step D2(b)

As an alternative, the compound of formula (XV) can be produced by reacting a compound of formula (XIV), in which Q represents a formyl group, in a first stage, with a 2,3-diaminopyridine derivative or a 4,5-diaminopyrimidine derivative, and then, in a second stage, treating the product with an oxidizing agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran, dioxane or 1,2-dimethoxyethane; amides, such as dimethylformamide, dimethylacetamide or hexamethylphosphoric triamide; alcohols, such as methanol, ethanol or isopropanol; acids, such as acetic acid or propionic acid; sulfoxides, such as dimethyl sulfoxide; and mixtures of any two or more of these solvents.

The reaction can take place over a wide range of temperatures, and the precise reaction temperature is not critical to the invention. In general, we find it convenient to carry out the reaction at about room temperature or with heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 1 hour to several days will usually suffice.

The product is then treated, in the second stage, with an oxidizing agent. There is no particular restriction on the nature of the oxidizing agent used, and any oxidizing agent commonly used in this type of reaction may equally be employed here. Examples of such oxidizing agents include iodine, silver oxide and lead tetraacetate, of which we prefer iodine.

The treatment with the oxidizing agent is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include the solvents cited above for use in the first stage, preferably the ethers.

The reaction can take place over a wide range of temperatures, and the precise reaction temperature is not critical to the invention. In general, we find it convenient to carry out the reaction with heating. The time required for the reaction may also vary widely, depending on many factors, notably the reaction temperature and the nature of the reagents and solvent employed. However, provided that the reaction is effected under the preferred conditions outlined above, a period of from 1 hour to several days will usually suffice.

In the compound of formula (XIV), where Q represents a protected formyl group, the formyl-protecting group may be removed prior to subjecting the compound to the reaction of Step D2. Examples of such protected formyl groups include: for example, the dimethoxymethyl, diethoxymethyl, 1,3-dioxan-2-yl, 1,3-dioxolan-2-yl, 1,3-dithian-2-yl and 1,3-dithiolan-2-yl groups. The formyl-protecting group can be removed by conventional methods well known in the art, for example by contacting the compound of formula (XIV) with a conventional deprotecting agent under the conditions conventionally used for deprotection. These conditions are described in T. W. Green: Protective Groups in Organic Synthesis (John Wiley & Sons Ed.) or J. F. W. McOmie: Protective Groups in Organic Chemistry (Plenum Press Ed.).

Reaction Scheme E

This is a process which may be used to prepare compounds of formula (I) in which Z represents a group of formula (ii) or (iii), that is a 2,4-dioxothiazolidin-5-ylmethyl or 2,4-dioxooxazolidin-5-ylmethyl group, i.e. compounds of formula (XV).

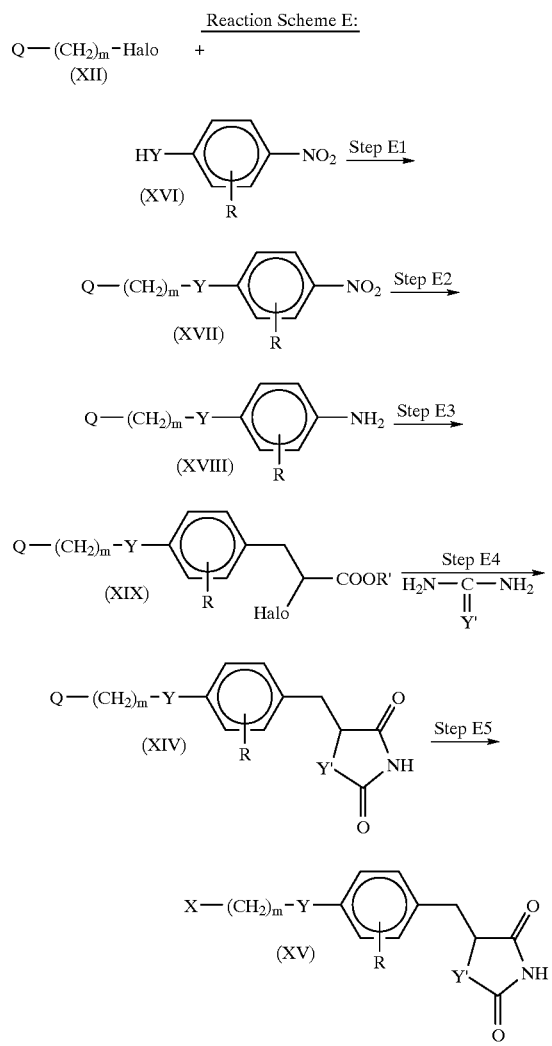

In the above formulae, Q, Y, Y', R' and m are as defined above;

Step E1

In Step E1, a compound of formula (XVII) is prepared by reacting a compound of formula (XII) with a compound of formula (XVI) with a base. This reaction is essentially the same as that described in Step D1 of Reaction Scheme D, and may be carried out using the same reagents and reaction conditions.

Step E2

In Step E2, a compound of formula (XVIII) is prepared by reducing a compound of formula (XVII).

The reaction may be carried out by a conventional catalytic hydrogenation or by using any reducing agent capable of reducing a nitro group, such as zinc-acetic acid or tin-hydrochloric acid.

Step E3

In Step E3, a compound of formula (XIX) is prepared by subjecting a compound of formula (XVIII) to a Meerwein arylation reaction.

The conditions employed for the reaction are well known and are generally similar to those disclosed in Japanese Patent Kokai Application No. Sho 55-22657 or reported by S. Oae et al.: Bull. Chem. Soc. Japan, 53 1065 (1980).

Step E4

In Step E4, a compound of formula (XIV) is prepared by reacting a compound of formula (XIX) with urea or thiourea and then subjecting the product to hydrolysis.

The conditions employed for this reaction are well known and are generally similar to those disclosed in Japanese Patent Kokai Application No. Sho 55-22657.

Step E5

In Step E5, a compound of formula (XV) is prepared from the compound (XIV), by one of Steps D(a) and D(b). The reaction is exactly the same as that shown in those Steps and may be carried out using the same reagents and reaction conditions.

In the steps described above, the products of each step can, if desired, be recovered from the reaction mixture by conventional means at the end of each reaction and, if necessary, the compounds obtained can be further purified by conventional means, for example, by column chromatography, recrystallization, reprecipitation or similar well known procedures. An example of one such technique comprises: adding a solvent to the reaction mixture; extracting the desired compound; and finally distilling off the solvent from the extract. The residue obtained may be purified by column chromatography through silica gel or like adsorbent to afford the desired compound as a pure specimen.

BIOLOGICAL ACTIVITY

The compounds of formula (I) and salts thereof possess the ability to lower blood glucose levels, to relieve obesity, to alleviate impaired glucose tolerance, to inhibit hepatic glucose neogenesis, to lower blood lipid levels and to inhibit aldose reductase. They are thus useful for the prevention and/or therapy of hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis.

The compounds of the present invention can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The activity of the compounds of the present invention is illustrated by the following Experiments.

Experiment 1
Hypoglycemic activity

The test animals used were hyperglycemic male mice of the KK strain, each having a body weight of at least 40 g. The compounds under test were mixed with a 1:1 by volume mixture of polyethylene glycol 400 and water. Each animal was orally administered a test compound in the amount shown in the following Table 6 and then allowed to feed freely for 18 hours. At the end of this time, blood was collected from the tail veins without anesthesia. The blood glucose level (BGL) was determined by means of a glucose analyzer (GL-101, manufactured by Mitsubishi Kasei Co. or a Glucoroder-F manufactured by Shino Test Co.).

The hypoglycemic effect was calculated by the following equation:

Hypoglycemic effect (%)=[(BGL$_s$−BGL$_t$)/BGL$_s$]×100 where:

BGL$_s$ is the blood glucose level in the group administered a solvent only, but no active compound; and BGL$_t$ is the blood glucose level in the group administered a test compound.

The results are shown in the following Table 6, in which each compound of the present invention is identified by the number of one of the following Examples in which its preparation is illustrated.

TABLE 6

| Cpd. of Example No. | Dose (mg/kg) | Hypoglycemic effect (%) |
|---|---|---|
| 1 | 10 | 13.2 |
| 2 | 1 | 27.7 |
| 3 | 10 | 27.0 |
| 5 | 10 | 16.2 |
| 6 | 10 | 20.9 |
| 7 | 1 | 24.7 |
| 9 | 10 | 27.6 |
| 10 | 1 | 11.6 |
| 13 | 1 | 34.0 |
| 15 | 1 | 13.8 |
| 17 | 1 | 37.1 |
| 20 | 1 | 24.5 |
| 22 | 1 | 10.2 |
| 23 | 1 | 21.7 |

As is apparent from Table 6, the compounds of the present invention exhibited excellent activity.

Experiment 2
Inhibition of Aldose reductase

Bovine lens aldose reductase was separated and partially purified by the method of S. Hyman and J. H. Kinoshita [J. Biol. Chem., 240, 877 (1965)] and K. Inagaki, I. Miwa and J. Okuda [Arch. Biochem. Biophys., 316, 337 (1982)], and its activity was determined photometrically by the method of Varma et al. [Biochem. Pharmac., 25, 2505 (1976)]. Inhibition of enzyme activity was measured for the compounds of the present invention at a concentration of 5 μg/ml, and the measured values were used to calculate the IC$_{50}$ values. The results are shown in the following Table 7.

TABLE 7

| Cpd. of Example No. | Inhibition (%) at 5 μg/ml | IC$_{50}$ (μg/ml) |
|---|---|---|
| 1 | 54.5 | — |
| 2 | 58.1 | 3.2 |
| 3 | — | 3.7 |
| 4 | — | 2.3 |
| 6 | 47 | — |
| 7 | — | 1.0 |
| 9 | 53.3 | — |
| 12 | — | 1.7 |
| 13 | — | 2.6 |
| 14 | 53.9 | — |
| 15 | — | 2.4 |
| 16 | 59.1 | 3.7 |
| 17 | — | 1.8 |
| 18 | 76.3 | 0.88 |
| 20 | 61.6 | 1.8 |
| 22 | 77.2 | 1.8 |
| 23 | 94.9 | 1.3 |
| 25 | 81.6 | 0.89 |
| 27 | 91.8 | 0.85 |

Experiment 3
Toxicity

The toxicity of the compounds of the present invention was tested on male F344 rats, divided into groups of 5. The test compound was adminstered orally to each test animal at a dose of 50 mg/kg of body weight per day for 2 weeks. The test compounds used were those of Examples 7 and 17. The animals were observed for 2 successive weeks, and, during that period, they showed no abnormalities which could be attributed to the test coumpounds. In view of the substantial dose adminstered to each animal, the zero mortality rate indicates that the compounds of the present invention have very low toxicity.

The compounds of the present invention thus have excellent activities combined with a very low toxicity, rendering them ideally suited to therapeutic use.

The present invention is further illustrated by the following non-limiting Examples. In these Examples, where Compound Nos. are given, they are those numbers assigned in the foregoing Tables 1 to 5. Preparation of certain of the starting materials used in some of these Examples is illustrated by the subsequent Preparations.

EXAMPLE 1

5-[4-(Indolin-2-ylmethoxy)benzyl]thiazolidine-2,4-dione (Compound No. 1-59)

A mixture of 3.55 g of 5-[4-(1-t-butoxycarbonylindolin-2-ylmethoxy)benzyl]-3-triphenylmethylthiazolidine-2,4-dione (prepared as described in Preparation 4) and 30 ml of trifluoroacetic acid was stirred at room temperature for 1 hour. At the end of this time, the reaction mixture was poured into water and the aqueous mixture was neutralized by the addition of sodium hydrogencarbonate, after which it was extracted with ethyl acetate. The extract was washed with an aqueous solution of sodium chloride and dried over anhydrous sodium sulfate, after which the solvent was removed by distillation under reduced pressure. The residue thus obtained was purified by column chromatography through silica gel, using a 2:1 by volume mixture of hexane and ethyl acetate as the eluent, to give 0.41 g of the title compound. This product was dissolved in ethanol and precipitated by adding water, to give a powder melting at 55.8–58.2° C.

EXAMPLE 2

5-[4-(1-Methylindolin-2-ylmethoxy)benzyl]thiazolidine-2,4-dione (Compound No. 1-62)

3.1 ml of trifluoroacetic acid were added to a solution of 2.50 g of 5-[4-(1-methylindolin-2-ylmethoxy)benzyl]-3-triphenylmethylthiazolidine-2,4-dione (prepared as described in Preparation 7) in 25 ml of methylene chloride, and the resulting mixture was stirred at room temperature for 1 hour. At the end of this time, the reaction mixture was worked up following the procedure described in Example 1, to give 1.20 g of the title compound, melting at 46.1–48.9° C.

EXAMPLE 3

5-{4-[2-(Indolin-1-yl)ethoxy]benzyl}thiazolidine-2,4-dione (Compound No. 1-57)

A procedure similar to that described in Example 2 was repeated, except that 470 mg of 5-{4-[2-(indolin-1-yl)ethoxy]benzyl}-3-triphenylmethylthiazolidine-2,4-dione (prepared as described in Preparation 10) and 3 ml of trifluoroacetic acid were used, to give 170 mg of the title compound, melting at 132.8–135.6° C.

EXAMPLE 4

5-{4-[2-(Indol-3-yl)ethoxy]benzyl}thiazolidine-2,4-dione (Compound No. 1-2)

A procedure similar to that described in Example 2 was repeated, except that 1.77 g of 5-{4-[2-(indol-3-yl)ethoxy]benzyl}-3-triphenylmethylthiazolidine-2,4-dione (prepared as described in Preparation 11), 53 ml of methylene chloride and 0.3 ml of trifluoroacetic acid were used, to give 0.67 g of the title compound, melting at 42.6–44.5° C.

EXAMPLE 5

5-{4-[2-(3-Triphenylmethylindol-1-yl)ethoxy]benzyl}thiazolidine-2,4-dione (Compound No. 1-3)

A procedure similar to that described in Example 2 was repeated, except that 2.33 g of 5-{4-[2-(indol-1-yl)ethoxy]benzyl}-3-triphenylmethylthiazolidine-2,4-dione (prepared as described in Preparation 14), 25 ml of methylene chloride and 3.1 ml of trifluoroacetic acid were used, to give 2.20 g of the title compound, melting at 66.6–70.0° C.

EXAMPLE 6

5-{4-[2-(Indol-1-yl)ethoxy]benzyl}thiazolidine-2,4-dione (Compound No. 1-1)

A solution of 2.05 g of 5-{4-[2-(indol-1-yl)-ethoxy]benzyl}-3-triphenylmethylthiazolidine-2,4-dione (prepared as described in Preparation 14) in 100 ml of dioxane was stirred in an atmosphere of hydrogen and in the presence of 3.1 g of 10% w/w palladium-on-charcoal, first at room temperature for 30 minutes, then at 60° C. for 2 hours and then at 80° C. for 3 hours. At the end of this time, the reaction mixture was filtered to remove the catalyst and the filtrate was concentrated by evaporation under reduced pressure. The concentrate was then purified by column chromatography through silica gel, using a 2:1 by volume mixture of hexane and ethyl acetate as the eluent, to give 1.06 g of the title compound, melting at 42.3–44.6° C.

EXAMPLE 7

5-{4-(3-Methylimidazo[5,4-b]pyridin-2-ylmethoxy)benzyl}thiazolidine-2,4-dione (Compound No. 1-93)

A procedure similar to that described in Example 6 was repeated, except that 500 mg of 5-[4-(3-methyl-imidazo[5,4-b]pyridin-2-ylmethoxy)benzyl]-3-triphenylmethylthiazolidine-2,4-dione (prepared as described in Preparation 16), 1 g of 10% w/w palladium-on-charcoal and 100 ml of methanol were used, to give 77 mg of the title compound, melting at 223–225° C.

EXAMPLE 8

5-{4-[2-(7-Azaindol-1-yl)ethoxy]benzyl}thiazolidine-2,4-dione (Compound No. 1-72)

A procedure similar to that described in Example 2 was repeated, except that 2.50 g of 5-{4-[2-(7-azaindol-1-yl)ethoxy]benzyl}-3-triphenylmethylthiazolidine-2,4-dione (prepared as described in Preparation 19), 50 ml of methylene chloride and 3.1 ml of trifluoroacetic acid were used, to give 0.84 g of the title compound, melting at 200.0–202.4° C.

EXAMPLE 9

5-{4-(Imidazo[1,2-a]pyridin-2-ylmethoxy)benzyl}-thiazolidine-2,4-dione (Compound No. 1-106)

A procedure similar to that described in Example 1 was repeated, except that 3.0 g of 5-{4-(imidazo-[1,2-a]pyridin-2-ylmethoxy)benzyl}-3-triphenylmethylthiazolidine-2,4-dione (prepared as described in Preparation 21) were reacted with 30 ml of trifluoroacetic acid for 1 hour. At the end of this time, the reaction mixture was freed from trifluoroacetic acid by distillation under reduced pressure. An aqueous solution of potassium carbonate and ethyl acetate were added to the residue, and the resulting precipitated insoluble material was collected by filtration, dried over anhydrous sodium sulfate and recrystallized from ethanol, to give 0.8 g of the title compound, melting at 197–202° C.

EXAMPLE 10

5-[4-(1-Methylindol-2-ylmethoxy)benzyl]thiazolidine-2,4-dione (Compound No. 1-6)

A procedure similar to that described in Example 6 was repeated, except that 3.24 g of 5-[4-(1-methylindol-2-ylmethoxy)benzyl]-3-triphenylmethylthiazolidine-2,4-dione (prepared as described in Preparation 24), 4.86 g of 10% w/w palladium-on-charcoal and 100 ml of dioxane were used, to give 1.49 g of the title compound, melting at 174.3–175.5° C.

EXAMPLE 11

5-[4-{2-(Imidazo[1,2-a]pyridin-2-yl)ethoxy}benzyl]-thiazolidine-2,4-dione (Compound No. 1-107)

A procedure similar to that described in Example 2 was repeated, except that 0.94 g of 5-[4-{2-(imidazo-[1,2-a]

pyridin-2-yl)ethoxy}benzyl]-3-triphenylmethylthiazolidine-2,4-dione (prepared as described in Preparation 27), 4 ml of methylene chloride and 1 ml of trifluoroacetic acid were used, to give the title compound as a crude product. This product was purified by column chromatography through silica gel, using a 2:1 by volume mixture of hexane and ethyl acetate and subsequently a 1:2 by volume mixture of ethyl acetate and tetrahydrofuran, as the eluents, to give 287 mg of the title compound, melting at 205.9–207.0° C. (with decomposition).

EXAMPLE 12

5-{4-(3-Ethylimidazo[5,4-b]pyridin-2-ylmethoxy)-benzyl}thiazolidine-2,4-dione (Compound No. 1-121)

12 ml of a 3:1 by volume mixture of acetic acid and water were added to 300 mg of 5-{4-(3-ethylimidazo[5,4-b]pyridin-2-ylmethoxy)benzyl}-3-triphenylmethylthiazolidine-2,4-dione (prepared as described in Preparation 29), and the resulting mixture was stirred at 60° C. for 2 hours. At the end of this time, the reaction mixture was neutralized by the addition of sodium hydrogencarbonate, after which it was extracted with ethyl acetate. The extract was washed with an aqueous solution of sodium chloride and dried over anhydrous sodium sulfate, after which the solvent was removed by distillation under reduced pressure. The residue was purified by column chromatography through silica gel, using ethyl acetate as the eluent, to give 85 mg of the title compound, melting at 210–212° C.

EXAMPLE 13

5-{4-(1-Methylimidazo[4,5-b]pyridin-2-ylmethoxy)-benzyl}thiazolidine-2,4-dione (Compound No. 1-122)

A procedure similar to that described in Example 12 was repeated, except that 4.1 g of 5-{4-(1-methylimidazo[4,5-b]pyridin-2-ylmethoxy)benzyl}-3-triphenylmethylthiazolidine-2,4-dione (prepared as described in Preparation 31) and 160 ml of a 3:1 by volume mixture of acetic acid and water were used, to give the title compound as a crude product. This crude product was crystallized by trituration with ethyl acetate, to give 1.45 g of the title compound, melting at 231–232° C.

EXAMPLE 14

5-[4-{3-(3-Methylimidazo[5,4-b]pyridin-2-yl)propoxy}-benzyl]thiazolidine-2,4-dione (Compound No. 1-123)

A procedure similar to that described in Example 12 was repeated, except that 240 mg of 5-[4-{3-(3-methylimidazo[5,4-b]pyridin-2-yl)propoxy}benzyl]-3-triphenylmethylthiazolidine-2,4-dione (prepared as described in Preparation 35) and 10 ml of a 3:1 by volume mixture of acetic acid and water were used, to give the title compound as a crude product. This crude product was purified by column chromatography through silica gel, using a gradient elution method, with mixtures of hexane and ethyl acetate in ratios ranging from 1:3 to 0:1 by volume as the eluent, to give 93 mg of the title compound, melting at 185–186° C.

EXAMPLE 15

5-{4-(1H-Imidazo[4,5-b]pyridin-2-ylmethoxy)benzyl}-thiazolidine-2,4-dione (Compound No. 1-91)

1.13 g of 4-(ethoxycarbonylmethoxy)-benzylthiazolidine-2,4-dione (prepared as described in Preparation 39) were added to 200 mg of 2,3-diaminopyridine, and the resulting mixture was stirred at 110° C. for 2 days. At the end of this time, the reaction mixture was treated with 3 N aqueous hydrochloric acid and subsequently made alkaline by the addition of aqueous ammonia. The aqueous mixture was evaporated to dryness under reduced pressure, and then the residue was purified by column chromatography through silica gel, using a gradient elution method, with mixtures of ethyl acetate and methanol in ratios ranging from 1:0 to 10:1 by volume as the eluent. The product was crystallized by trituration with ethyl acetate, to give 400 mg of the title compound, melting at 247–248° C.

EXAMPLE 16

5-{4-(3,7-Dimethylimidazo[5,4-b]pyridin-2-ylmethoxy)-benzyl}thiazolidine-2,4-dione (Compound No. 1-124)

A procedure similar to that described in Example 12 was repeated, except that 1.07 g of 5-{4-(3,7-dimethylimidazo[5,4-b]pyridin-2-ylmethoxy)benzyl}-3-triphenylmethylthiazolidine-2,4-dione (prepared as described in Preparation 41) and 16 ml of a 3:1 by volume mixture of acetic acid and water were used, to give the title compound as a crude product. This crude product was purified by column chromatography through silica gel, using a gradient elution method, with mixtures of hexane and ethyl acetate in ratios ranging from 1:1 to 1:2 by volume as the eluent. The product was crystallized by trituration with ethyl acetate, to give 0.28 g of the title compound, melting at 205–207° C.

EXAMPLE 17

5-{4-(5-Chloro-3-methylimidazo[5,4-b]pyridin-2-ylmethoxy)benzyl}thiazolidine-2,4-dione (Compound No. 1-125)

A procedure similar to that described in Example 12 was repeated, except that 1.16 g of 5-{4-(5-chloro-3-methylimidazo[5,4-b]pyridin-2-ylmethoxy)benzyl}-3-triphenylmethylthiazolidine-2,4-dione (prepared as described in Preparation 45) and 16 ml of a 3:1 by volume mixture of acetic acid and water were used, to give the title compound as a crude product. The product was crystallized by trituration with ethyl acetate, to give 0.38 g of the title compound, melting at 222–223° C.

EXAMPLE 18

5-{4-(3-Methyl-6-trifluoromethylimidazo[5,4-b]pyridin-2-ylmethoxy)benzyl}thiazolidine-2,4-dione (Compound No. 1-130)

4.16 g of 5-(4-(2-oxcethoxy)benzyl)thiazolidine-2,4-dione (prepared as described in Preparation 47) were added to a solution of 3.00 g of 3-amino-2-methylamino-5-trifluoromethylpyridine in a mixture of 6 ml of ethanol and 6 ml of acetic acid, and the resulting mixture was stirred at room temperature for 4 hours. At the end of this time, the reaction mixture was freed from the solvent by distillation under reduced pressure. 50 ml of 1,2-dimethoxyethane and 5.2 g of iodine were added to the residue, and the resulting mixture was stirred at 60° C. for one day. At the end of this time, the reaction mixture was poured into water, after which it was extracted with ethyl acetate. The extract was washed with an aqueous solution of sodium chloride and dried over anhydrous sodium sulfate, after which the solvent was removed by distillation under reduced pressure. The residue was purified by column chromatography through silica gel, using a 1:1 by volume mixture of hexane and ethyl acetate as the eluent. The product was crystallized by trituration with ethyl acetate, to give 520 mg of the title compound, melting at 212–214° C.

EXAMPLE 19

5-{4-(3-Methylimidazo[5,4-d]pyrimidin-2-ylmethoxy)benzyl}thiazolidine-2,4-dione (Compound No. 1-158)

A procedure similar to that described in Example 12 was repeated, except that 0.24 g of 5-{4-(3-methylimidazo[5,4-d]pyrimidin-2-ylmethoxy)benzyl}-3-triphenylmethylthiazolidine-2,4-dione (prepared as described in Preparation 51) and 8 ml of a 3:1 by volume mixture of acetic acid and water were used, to give the title compound as a crude product. This crude product was purified by column chromatography through silica gel, using a gradient elution method, with mixtures of ethyl acetate and ethanol in ratios ranging from 1:0 to 10:1 by volume as the eluent, to give 30 mg of the title compound, melting at 244–246° C.

EXAMPLE 20

5-(4-{3-(4-Chlorobenzyl)imidazo[5,4-b]pyridin-2-ylmethoxy}benzyl)thiazolidine-2,4-dione (Compound No. 1-134)

A procedure similar to that described in Example 18 was repeated, except that 1.20 g of 3-amino-2-(4-chlorobenzyl) aminopyridine (prepared as described in Preparation 53), 1.36 g of 5-[4-(2-oxoethoxy)benzyl]-thiazolidine-2,4-dione (prepared as described in Preparation 47), 3 ml of ethanol, 3 ml of acetic acid, 1.69 g of iodine and 25 ml of 1,2-dimethoxyethane were used, to give the title compound as a crude product. This crude product was purified by column chromatography through silica gel, using a gradient elution method, with mixtures of hexane and ethyl acetate in ratios ranging from 1:1 to 1:2 by volume as the eluent, to give 0.40 g of the title compound, melting at 211–213° C.

EXAMPLE 21

5-(4-{3-(4-Phenylbenzyl)imidazo[5,4-b]pyridin-2-ylmethoxy}benzyl)thiazolidine-2,4-dione (Compound No. 1-135)

A procedure similar to that described in Example 12 was repeated, except that 0.9 g of 5-(4-{3-(4-phenylbenzyl) imidazo[5,4-b]pyridin-2-ylmethoxy}benzyl)-3-triphenylmethylthiazolidine-2,4-dione (prepared as described in Preparation 55) and 36 ml of a 3:1 by volume mixture of acetic acid and water were used, to give the title compound as a crude product. This crude product was purified by column chromatography through silica gel, using a 1:3 by volume mixture of hexane and ethyl acetate as the eluent, to give 450 mg of the title compound, melting at 189–191° C.

EXAMPLE 22

5-{4-(6-Bromo-3-methylimidazo[5,4-b]pyridin-2-ylmethoxy)benzyl}thiazolidine-2,4-dione (Compound No. 1-137)

A procedure similar to that described in Example 12 was repeated, except that 3.00 g of 5-{4-(6-bromo-3-methylimidazo[5,4-b]pyridin-2-ylmethoxy)benzyl}-3-triphenylmethylthiazolidine-2,4-dione (prepared as described in Preparation 60) and 40 ml of a 3:1 by volume mixture of acetic acid and water were used, to give the title compound as a crude product. This crude product was crystallized by trituration with ethyl acetate, to give 1.75 g of the title compound, melting at 204–205° C.

EXAMPLE 23

5-{4-(6-Chloro-3-methylimidazo[5,4-b]pyridin-2-ylmethoxy)benzyl}thiazolidine-2,4-dione (Compound No. 1-140)

A procedure similar to that described in Example 12 was repeated, except that 1.40 g of 5-{4-(6-chloro-3-methylimidazo[5,4-b]pyridin-2-ylmethoxy)benzyl}-3-triphenylmethylthiazolidine-2,4-dione (prepared as described in Preparation 65) and 20 ml of a 3:1 by volume mixture of acetic acid and water were used, to give the title compound as a crude product. This crude product was crystallized by trituration with ethyl acetate, to give 0.75 g of the title compound, melting at 203–205° C.

EXAMPLE 24

5-{4-(5-Methoxy-3-methylimidazo[5,4-b]pyridin-2-ylmethoxy)benzyl}thiazolidine-2,4-dione (Compound No. 1-142) and the hydrochloride and fumarate thereof (1) A procedure similar to that described in Example 12 was repeated, except that 680 mg of 5-{4-(5-methoxy-3-methylimidazo[5,4-b]pyridin-2-ylmethoxy)-benzyl}-3-triphenylmethylthiazolidine-2,4-dione (prepared as described in Preparation 70) and 10 ml of a 3:1 by volume mixture of acetic acid and water were used, to give the title compound as a crude product. This crude product was crystallized by trituration with ethyl acetate, to give 325 mg of the title compound, melting at 258–260° C.

(2) 100 mg of 5-{4-(5-methoxy-3-methylimidazo[5,4-b] pyridin-2-ylmethoxy)benzyl}thiazolidine-2,4-dione [prepared as described in step (1) above] were added to 6 ml of a 4 N solution of hydrogen chloride in ethyl acetate, and the mixture was treated with ultrasound for 30 minutes. At the end of this time, the resulting crystals were collected by filtration and dried by evaporation under reduced pressure, to give 87 mg of the hydrochloride of the title compound, melting at 255–262° C.

(3) 100 mg of 5-{4-(5-methoxy-3-methylimidazo[5,4-b] pyridin-2-ylmethoxy)benzyl}thiazolidine-2,4-dione [prepared as described in step (1) above] were dissolved in 30 ml of methanol, and then 29 mg of fumaric acid were added to the resulting solution. The resulting mixture was treated with ultrasound for 30 minutes. At the end of this time, the solvent was removed by distillation under reduced pressure. The residue was triturated with ethanol and the resulting crystals were collected by filtration, to give 85 mg of the fumarate ethanol hemi-solvate of the title compound, melting at 245–253° C.

EXAMPLE 25

5-{4-(1-Methylimidazo[4,5-c]pyridin-2-ylmethoxy)-benzyl}thiazolidine-2,4-dione (Compound No. 1-156)

A procedure similar to that described in Example 12 was repeated, except that 3.40 g of S-{4-(1-methylimidazo[4,5- c]pyridin-2-ylmethoxy)benzyl}-3-triphenylmethylthiazolidine-2,4-dione (prepared as described in Preparation 74) and 24 ml of a 3:1 by volume mixture of acetic acid and water were used, to give the title compound as a crude product. This crude product was crystallized by trituration with ethyl acetate, to give 1.01 g of the title compound, melting at 264–265° C.

EXAMPLE 26

5-[4-(1-Methyl-7-azaindol-2-ylmethoxy)benzyl]thiazolidine-2,4-dione (Compound No. 1-81)

A procedure similar to that described in Example 12 was repeated, except that the reaction was conducted using 270 mg of 5-[4-(1-methyl-7-azaindol-2-ylmethoxy)-benzyl]-3-triphenylmethylthiazolidine-2,4-dione (prepared as described in Preparation 82) and 3 ml of a 2:1:3 by volume mixture of acetic acid, water and 1,4-dioxane. After the period allowed for the reaction had elapsed, the reaction mixture was freed from the solvent by distillation under reduced pressure. The residue was purified by column chromatography through silica gel, using a 1:1 by volume mixture of hexane and ethyl acetate as the eluent, to give 157 mg of the title compound, melting at 183–185° C.

EXAMPLE 27

5-{4-(3-Phenylimidazo[5,4-b]pyridin-2-ylmethoxy)-benzyl}thiazolidine-2,4-dione (Compound No. 1-161)

A procedure similar to that described in Example 18 was repeated, except that 2.78 g of 3-amino-2-phenyl-aminopyridine (prepared as described in Preparation 84), 3.98 g of 5-[4-(2-oxcethoxy)benzyl)thiazolidine-2,4-dione (prepared as described in Preparation 47), 4.9 g of iodine, 6 ml of ethanol, 6 ml of acetic acid and 50 ml of 1,2-dimethoxyethane were used. After working up the product as described in Example 18, the resulting crude product was purified by column chromatography through silica gel, using a 1:2 by volume mixture of hexane and ethyl acetate as the eluent, to give 400 mg of the title compound, melting at 88–91° C.

EXAMPLE 28

5-{4-(3,5,7-Trimethylimidazo[5,4-b]pyridin-2-ylmethoxy)benzyl}thiazolidine-2,4-dione (Compound No. 1-218) and its trifluoroacetate A procedure similar to that described in Example 2 was repeated, except that 3.5 g of 5-{4-(3,5,7-trimethylimidazo[5,4-b]pyridin-2-ylmethoxy)benzyl}-3-triphenylmethylthiazolidine-2,4-dione (prepared as described in Preparation 87), 100 ml of methylene chloride and 20 ml of trifluoroacetic acid were used. After the period allowed for the reaction had elapsed, the reaction mixture was freed from the methylene chloride and trifluoroacetic acid by distillation under reduced pressure. The crude product thus obtained was recrystallized from a mixture of ethyl acetate and hexane, to give 2.4 g of the trifluoroacetate of the title compound, melting at 226–228° C.

The trifluoroacetate (2.3 g) prepared as described above was suspended in a mixture of ethyl acetate (50 ml) and an aqueous solution of sodium hydrogencarbonate (50 ml), and the suspension was stirred at room temperature for 30 minutes. At the end of this time, the crystals which had precipitated were collected by filtration and washed with water, after which they were dried under reduced pressure, to give 1.47 g of the title compound, melting at 229–230° c.

EXAMPLE 29

5-{4-(3-Methyl-5-phenylthioimidazo[5,4-b]pyridin-2-ylmethoxy)benzyl}thiazolidine-2,4-dione (Compound No. 1-177)

A procedure similar to that described in Example 12 was repeated, except that 1.58 g of 5-[4-(3-methyl-5-phenylthioimidazo[5,4-b]pyridin-2-ylmethoxy)benzyl]-3-triphenylmethylthiazolidine-2,4-dione (prepared as described in Preparation 91) were treated with 20 ml of a 3:1 by volume mixture of acetic acid and water. After working up the product as described in Example 12, the resulting crude product was crystallized by trituration with ethyl acetate, to give 1.02 g of the title compound, melting at 166–168° C.

EXAMPLE 30

5-{4-(5-Benzyloxy-3-methylimidazo[5,4-b]pyridin-2-ylmethoxy)benzyl}thiazolidine-2,4-dione (Compound No. 1-207)

A procedure similar to that described in Example 12 was repeated, except that 1.00 g of 5-{4-(5-benzyloxy-3-methylimidazo[5,4-b]pyridin-2-ylmethoxy)benzyl}-3-triphenylmethylthiazolidine-2,4-dione (prepared as described in Preparation 95) was treated with 12 ml of a 3:1 by volume mixture of acetic acid and water. After working up the product as described in Example 12, the resulting crude product was crystallized by trituration with ethyl acetate, to give 0.63 g of the title compound, melting at 210–211° C.

EXAMPLE 31

5-{4-(5-Hydroxy-3-methylimidazo[5,4-b]pyridin-2-ylmethoxy)benzyl}thiazolidine-2,4-dione (Compound No. 1-153)

A procedure similar to that described in Example 6 was repeated, except that 1.20 g of 5-{4-(5-benzyloxy-3-methylimidazo[5,4-b]pyridin-2-ylmethoxy)benzyl}-3-triphenylmethylthiazolidine-2,4-dione (prepared as described in Preparation 95), 1.80 g of 10% w/w palladium-on-charcoal and 50 ml of methanol were used, and that the product was purified by column chromatography through silica gel, using a gradient elution method, with mixtures of ethyl acetate and methanol in ratios ranging from 1:0 to 10:1 by volume as the eluent, to give 0.10 g of the title compound, melting at 240–242° C.

EXAMPLE 32

5-{4-(5-Ethoxy-3-methylimidazo[5,4-b]pyridin-2-ylmethoxy)benzyl}thiazolidine-2,4-dione (Compound No. 1-182)

A procedure similar to that described in Example 12 was repeated, except that 2.75 g of 5-{4-(5-ethoxy-3-methylimidazo[5,4-b]pyridin-2-ylmethoxy)benzyl}-3-triphenylmethylthiazolidine-2,4-dione (prepared as described in Preparation 99) were treated with 24 ml of a 3:1 by volume mixture of acetic acid and water. After working up the product as described in Example 12, the resulting crude product was crystallized by trituration with ethyl acetate, to give 1.57 g of the title compound, melting at 245–246° C.

EXAMPLE 33

5-{4-(5-Isopropoxy-3-methylimidazo[5,4-b]pyridin-2-ylmethoxy)benzyl}thiazolidine-2,4-dione (Compound No. 1-183)

A procedure similar to that described in Example 12 was repeated, except that 0.78 g of 5-{4-(5-isopropoxy-3-methylimidazo[5,4-b]pyridin-2-ylmethoxy)benzyl}-3-triphenylmethylthiazolidine-2,4-dione (prepared as described in Preparation 103) was treated with 12 ml of a 3:1 by volume mixture of acetic acid and water. After working up the product as described in Example 12, the resulting crude product was crystallized by trituration with ethyl acetate, to give 0.40 g of the title compound, melting at 210–212° C.

EXAMPLE 34

5-{4-[2-(3-Methylimidazo[5,4-b]pyridin-2-yl)ethoxy]benzyl}thiazolidine-2,4-dione (Compound No. 1-190)

A procedure similar to that described in Example 18 was repeated, except that 0.94 g of 3-amino-2-methyl-aminopyridine (prepared as described in Preparation 105), 2.10 g of 5-[4-(3-oxopropoxy)benzyl]thiazolidine-2,4-dione (prepared as described in Preparation 107), 6 ml of ethanol, 3 ml of acetic acid, 2.32 g of iodine and 30 ml of 1,2-dimethoxyethane were used. After working up the product as described in Example 18, the resulting crude product was purified by column chromatography through silica gel, using ethyl acetate as the eluent, to give 85 mg of the title compound, melting at 96–100° C.

EXAMPLE 35

5-{4-(3-Methyl-5-phenylimidazo[5,4-b]pyridin-2-ylmethoxy)benzyl}thiazolidine-2,4-dione (Compound No. 1-179)

A procedure similar to that described in Example 12 was repeated, except that 0.9 g of 5-{4-(3-methyl-5-phenylimidazo[5,4-b]pyridin-2-ylmethoxy)benzyl}-3-triphenylmethylthiazolidine-2,4-dione (prepared as described in Preparation 111) was treated with 36 ml of a 3:1 by volume mixture of acetic acid and water. After working up the product as described in Example 12, the resulting crude product was crystallized by trituration with ethyl acetate, to give 420 mg of the title compound, melting at 211–213° C.

EXAMPLE 36

5-{4-(3-Methylimidazo[5,4-b]pyridin-2-ylmethoxy)benzylidene}thiazolidine-2,4-dione (Compound No. 2-100)

A mixture of 0.35 g of 2-(4-formylphenoxymethyl)-3-methylimidazo[5,4-b]pyridine (prepared as described in Preparation 112), 0.31 g of 2,4-thiazolidinedione, 0.26 ml of piperidine and 10 ml of ethanol was heated under reflux for 4 hours. At the end of this time, the solvent was removed by distillation under reduced pressure and the residue was crystallized by trituration with water. The crystals were collected by filtration and washed with water and then with ethyl acetate, to give 0.38 g of the title compound, melting at 279–281° C.

PREPARATION 1

Ethyl indoline-2-carboxylate

A mixture of 25.2 g of indoline-2-carboxylic acid, 50 ml of ethanol and 200 ml of a 4 N solution of hydrogen chloride in dioxane was stirred at room temperature for 3 days. At the end of this time, the reaction mixture was poured into an aqueous solution of potassium carbonate, after which it was extracted with ethyl acetate. The extract was washed with an aqueous solution of sodium chloride and dried over anhydrous sodium sulfate. The solvent was removed by distillation under reduced pressure, and the residue thus obtained was purified by column chromatography through silica gel, using a 2:1 by volume mixture of hexane and ethyl acetate as the eluent, to give 28.1 g of the title compound having Rf=0.81 (on silica gel thin layer chromatography using a 2:1 by volume mixture of hexane and ethyl acetate as the developing solvent).

PREPARATION 2

Indolin-2-ylmethanol

A solution of 5.12 g of ethyl indoline-2-carboxylate (prepared as described in Preparation 1) in 20 ml of anhydrous tetrahydrofuran was added dropwise, whilst ice-cooling, to a mixture of 1.20 g of lithium aluminum hydride and 80 ml of anhydrous tetrahydrofuran, and the resulting mixture was stirred at room temperature for 2 hours. After this, an excess of sodium sulfate decahydrate was added to the mixture, which was then stirred for 20 minutes. At the end of this time, insoluble materials were filtered off and the filtrate was concentrated by evaporation under reduced pressure. The concentrate was purified by column chromatography through silica gel, using a 3:1 by volume mixture of hexane and ethyl acetate as the eluent, to give 3.81 g of the title compound having Rf=0.16 (on silica gel thin layer chromatography using a 2:1 by volume mixture of hexane and ethyl acetate as the developing solvent).

PREPARATION 3

1-t-Butoxycarbonyl-2-hydroxymethylindoline 6.2 ml of di-t-butyl dicarbonate were added dropwise to a solution of 4.0 g of indolin-2-ylmethanol (prepared as described in Preparation 2) and 3.8 ml of triethylamine in 40 ml of anhydrous tetrahydrofuran, and the resulting mixture was stirred at room temperature for 10 hours. At the end of this time, the reaction mixture was poured into water, after which it was extracted with ethyl acetate. The extract was washed with an aqueous solution of sodium chloride and dried over anhydrous sodium sulfate. The solvent was then removed by distillation under reduced pressure, and the resulting residue was purified by column chromatography through silica gel, using a 5:1 by volume mixture of hexane and ethyl acetate as the eluent, to give 5.57 g of the title compound having Rf=0.46 (on silica gel thin layer chromatography using a 2:1 by volume mixture of hexane and ethyl acetate as the developing solvent).

PREPARATION 4

5-[4-(1-t-Butoxycarbonylindolin-2-ylmethoxy)benzyl]-3-triphenylmethylthiazolidine-2,4-dione A solution of 6.6 g of 1,1'-(azodicarbonyl)dipiperidine in 10 ml of anhydrous tetrahydrofuran and 20 ml of anhydrous dimethylformamide was added dropwise to a mixture of 6.5 g of 1-t-butoxycarbonyl-2-hydroxy-methylindoline (prepared as described in Preparation 3), 6.5 ml of tributylphosphine, 12.2 g of 5-(4-hydroxybenzyl)-3-triphenylmethylthiazolidine-2,4-dione [prepared as described in European Patent Publication No. 549 365A1]

and 100 ml of anhydrous tetrahydrofuran, and the resulting mixture was stirred at room temperature for about 20 hours. At the end of this time, insoluble materials were filtered off and the filtrate was concentrated by evaporation under reduced pressure. The concentrate thus obtained was purified by column chromatography through silica gel, using a 10:1 by volume mixture of hexane and ethyl acetate as the eluent, to give 3.70 g of the title compound, melting at 85.4–87.2° C.

PREPARATION 5

Methyl 1-methylindoline-2-carboxylate 11.7 ml of methyl iodide were added dropwise to a mixture of 10.3 g of (±)-indoline-2-carboxylic acid, 200 ml of dimethylformamide and 25.4 g of anhydrous potassium carbonate, and the resulting mixture was stirred at room temperature for 3 hours. At the end of this time, the reaction mixture was poured into water, after which it was extracted with ethyl acetate. The extract was washed with an aqueous solution of sodium chloride and dried over anhydrous sodium sulfate. The solvent was then removed by distillation under reduced pressure, and the resulting residue was purified by column chromatography through silica gel, using a 7:1 by volume mixture of hexane and ethyl acetate as the eluent, to give 9.12 g of the title compound having Rf=0.77 (on silica gel thin layer chromatography using a 2:1 by volume mixture of hexane and ethyl acetate as the developing solvent).

PREPARATION 6

1-Methylindolin-2-ylmethanol

A procedure similar to that described in Preparation 2 was repeated, except that 8.0 g of methyl 1-methylindoline-2-carboxylate (prepared as described in Preparation 5), 1.91 g of lithium aluminum hydride and 250 ml of tetrahydrofuran were used, to give 6.85 g of the title compound having Rf=0.35 (on silica gel thin layer chromatography using a 2:1 by volume mixture of hexane and ethyl acetate as the developing solvent).

PREPARATION 7

5-[4-(1-Methylindolin-2-ylmethoxy)benzyl]-3-triphenylmethylthiazolidine-2,4-dione A procedure similar to that described in Preparation 4 was repeated, except that 2.0 g of 1-methylindolin-2-ylmethanol (prepared as described in Preparation 6), 4.73 g of 5-(4-hydroxybenzyl)-3-triphenylmethylthiazolidine-2,4-dione, 2.53 ml of tributylphosphine, 2.57 g of 1,1'-(azodicarbonyl)dipiperidine and 55 ml of benzene were used, to give 4.39 g of the title compound, melting at 62.5–65.5° C.

PREPARATION 8

Methyl indolin-1-ylacetate 0.40 ml of methyl bromoacetate was added dropwise to a mixture of 0.25 g of indoline, 2 ml of dimethylformamide and 0.87 g of anhydrous potassium carbonate, and the resulting mixture was stirred at room temperature for 1 hour. At the end of this time, the reaction mixture was poured into water, after which it was extracted with ethyl acetate. The extract was washed with an aqueous solution of sodium chloride and dried over anhydrous sodium sulfate. The solvent was removed by distillation under reduced pressure, and the resulting residue was purified by column chromatography through silica gel, using a 5:1 by volume mixture of hexane and ethyl acetate as the eluent, to give 0.30 g of the title compound having Rf=0.63 (on silica gel thin layer chromatography using a 2:1 by volume mixture of hexane and ethyl acetate as the developing solvent).

PREPARATION 9

2-(Indolin-1-yl)ethanol

A procedure similar to that described in Preparation 2 was repeated, except that 780 mg of methyl indolin-1-ylacetate (prepared as described in Preparation 8), 200 mg of lithium aluminum hydride and 12 ml of anhydrous tetrahydrofuran were used, to give 580 mg of the title compound having Rf=0.31 (on silica gel thin layer chromatography using a 2:1 by volume mixture of hexane and ethyl acetate as the developing solvent).

PREPARATION 10

5-{4-[2-(Indolin-1-yl)ethoxy]benzyl}-3-triphenylmethylthiazolidine-2,4-dione

A procedure similar to that described in Preparation 4 was repeated, except that 240 mg of 2-(indolin-1-yl)ethanol (prepared as described in Preparation 9), 690 mg of 5-(4-hydroxybenzyl)-3-triphenylmethylthiazolidine-2,4-dione, 0.37 ml of tributylphosphine, 370 mg of 1,1'-(azodicarbonyl)dipiperidine and 5 ml of anhydrous tetrahydrofuran were used, to give 530 mg of the title compound having Rf=0.88 (on silica gel thin layer chromatography using a 2:1 by volume mixture of hexane and ethyl acetate as the developing solvent).

PREPARATION 11

5-{4-[2-(Indol-3-yl)ethoxy]benzyl}-3-triphenylmethylthiazolidine-2,4-dione

A procedure similar to that described in Preparation 4 was repeated, except that 5.0 g of 2-(indol-3 -yl)-ethanol, 14.4 g of 5-(4-hydroxybenzyl)-3-triphenylmethylthiazolidine-2,4-dione, 7.73 ml of tributylphosphine, 7.83 g of 1,1'-(azodicarbonyl)dipiperidine and 150 ml of anhydrous benzene were used, to give 3.03 g of the title compound, melting at 81.0–82.5° C.

PREPARATION 12

Methyl indol-1-ylacetate

A solution of 5.0 g of indole in 20 ml of dimethylformamide was added dropwise, whilst ice-cooling, to a mixture of 2.0 g of sodium hydride (as a 55% by weight dispersion in mineral oil, and which had previously been washed with hexane) and 80 ml of dimethylformamide, and the resulting mixture was stirred at room temperature for 1 hour. At the end of this time, 4.5 ml of methyl bromoacetate were added dropwise, whilst ice-cooling, to the mixture, which was then stirred at room temperature for 2 hours. After it had been stirred for this time, the reaction mixture was poured into ice-water, and then it was extracted with ethyl acetate. The extract was washed with an aqueous solution of sodium chloride and dried over anhydrous sodium sulfate. The solvent was then removed by distillation under reduced pressure, and the resulting residue was purified by column chromatography through silica gel, using a 10:1 by volume mixture of hexane and ethyl acetate as the eluent, to give 6.52 g of the title compound having Rf=0.66 (on silica gel thin layer chromatography using a 2:1 by volume mixture of hexane and ethyl acetate as the developing solvent).

PREPARATION 13

2-(Indol-1-yl)ethanol

A procedure similar to that described in Preparation 2 was repeated, except that 6.20 g of methyl indol-1-ylacetate (prepared as described in Preparation 12), 1.50 g of lithium aluminum hydride and 220 ml of anhydrous tetrahydrofuran were used, to give 5.25 g of the title compound having Rf=0.33 (on silica gel thin layer chromatography using a 2:1 by volume mixture of hexane and ethyl acetate as the developing solvent).

PREPARATION 14

5-{4-[2-(Indol-1-yl)ethoxy]benzyl}-3-triphenylmethylthiazolidine-2,4-dione

A procedure similar to that described in Preparation 4 was repeated, except that 2.0 g of 2-(indol-1-yl)-ethanol (prepared as described in Preparation 13), 4.81 g of 5-(4-hydroxybenzyl)-3-triphenylmethylthiazolidine-2,4-dione, 3.1 ml of tributylphosphine, 3.20 g of 1,1'-(azodicarbonyl) dipiperidine and 60 ml of anhydrous benzene were used, to give 5.69 g of the title compound, melting at 63.5–65.9° C.

PREPARATION 15

3-Methylimidazo[5,4-b]pyridin-2-ylmethanol 3.35 g of imidazo[5,4-b]pyridin-2-ylmethanol were added to a mixture of 0.98 g of sodium hydride (as a 55% by weight dispersion in mineral oil, and which had previously been washed with hexane) and 100 ml of dimethylformamide, and the resulting mixture was stirred at room temperature for 6 hours, after which 3.51 g of methyl iodide were added to the mixture, whilst ice-cooling. The mixture was then stirred at room temperature for 15 hours. At the end of this time, the reaction mixture was freed from dimethylformamide by distillation under reduced pressure. The residue thus obtained was purified by column chromatography through silica gel, using a gradient elution method, with mixtures of ethyl acetate and ethanol in ratios ranging from 1:0 to 10:1 by volume as the eluent, to give 1.7 g of the title compound, melting at 229–231° C.

PREPARATION 16

5-{4-(3-Methylimidazo[5,4-b]pyridin-2-ylmethoxy) benzyl}-3-triphenylmethylthiazolidine-2,4-dione A procedure similar to that described in Preparation 4 was repeated, except that 0.5 g of 3-methylimidazo[5,4-b] pyridin-2-ylmethanol (prepared as described in Preparation 15), 1.43 g of 5-(4-hydroxybenzyl)-3-triphenylmethylthiazolidine-2,4-dione, 0.83 ml of tributylphosphine, 0.773 g of 1,1'-(azodicarbonyl) dipiperidine and 80 ml of benzene were used, to give 0.3 g of the title compound, melting at 97–102° C.

PREPARATION 17

Methyl 7-azaindol-1-acetate

A procedure similar to that described in Preparation 12 was repeated, except that 1.90 g of sodium hydride (as a 55% by weight dispersion in mineral oil), 4.95 g of 7-azaindol, 100 ml of dimethylformamide and 4.2 ml of methyl bromoacetate were used, to give 7.70 g of the title compound having Rf=0.33 (on silica gel thin layer chromatography using a 2:1 by volume mixture of hexane and ethyl acetate as the developing solvent).

PREPARATION 18

2-(7-Azaindol-1-yl)ethanol

A procedure similar to that described in Preparation 2 was repeated, except that 7.50 g of methyl 7-azaindol-1-acetate (prepared as described in Preparation 17), 1.80 g of lithium aluminum hydride and 260 ml of anhydrous tetrahydrofuran were used, to give 5.57 g of the title compound, melting at 52.7–53.3° C.

PREPARATION 19

5-{4-[2-(7-Azaindol-1-yl)ethoxy]benzyl}-3-triphenylmethylthiazolidine-2,4-dione

A procedure similar to that described in Preparation 4 was repeated, except that 1.77 g of 2-(7-azaindol-1-yl)ethanol (prepared as described in Preparation 18), 4.40 g of 5-(4-hydroxybenzyl)-3-triphenylmethylthiazolidine-2,4-dione, 2.35 ml of tributylphosphine, 2.39 g of 1,1'-(azodicarbonyl) dipiperidine and 45 ml of anhydrous benzene were used, to give 4.58 g of the title compound, melting at 167.5–168.9° C.

PREPARATION 20

Imidazo[1,2-a]pyridin-2-ylmethanol 3.68 g of lithium borohydride were added at room temperature to a solution of 9.17 g of ethyl imidazo[1,2-a] pyridine-2-carboxylate [described in J. Org. Chem., 30, 2403–2407 (1965)] in 200 ml of tetrahydrofuran, and then 20 ml of methanol were added dropwise to the mixture, which was then allowed to stand overnight at room temperature. At the end of this time, the reaction mixture was diluted with 10 ml of water and then concentrated by evaporation under reduced pressure. The concentrate was mixed with an aqueous solution of sodium chloride, after which it was extracted with ethyl acetate. The extract was dried over anhydrous sodium sulfate, after which the solvent was removed by distillation under reduced pressure. The resulting residue was purified by column chromatography through silica gel, using a 5:1 by volume mixture of ethyl acetate and ethanol as the eluent. The product was then recrystallized from a mixture of ethyl acetate and hexane, to give 0.56 g of the title compound, melting at 126–128° C.

PREPARATION 21

5-{4-(Imidazo[1,2-a]pyridin-2-ylmethoxy)benzyl}-3-triphenylmethylthiazolidine-2,4-dione A procedure similar to that described in Preparation 4 was repeated, except that 920 mg of imidazo(1,2-a]-pyridin-2-ylmethanol (prepared as described in Preparation 20), 2.9 g of 5-(4-hydroxybenzyl)-3-triphenylmethylthiazolidine-2,4-dione, 1.4 g of tributylphosphine, 1.65 g of 1,1'-(azodicarbonyl)dipiperidine and 60 ml of benzene were used, to give 3.1 g of the title compound having Rf=0.71 (on silica gel thin layer chromatography using a 10:1 by volume mixture of ethyl acetate and ethanol as the developing solvent).

PREPARATION 22

Methyl 1-methylindole-2-carboxylate 6.0 ml of methyl iodide were added dropwise to a mixture of 5.00 g of indole-2-carboxylic acid, 100 ml of dimethylformamide and 13.0 g of anhydrous potassium carbonate, and the resulting mixture was stirred at 100° C. for 6 hours. At the end of this time, the reaction mixture was worked up following the procedure described in Preparation 5, to give 5.12 g of the title compound, melting at 91.3–92.8° C.

PREPARATION 23

1-Methylindol-2-ylmethanol

A solution of 5.05 g of methyl 1-methylindole-2-carboxylate (prepared as described in Preparation 22) in 20 ml of anhydrous tetrahydrofuran was added dropwise to a mixture of 1.85 g of lithium borohydride and 80 ml of anhydrous tetrahydrofuran, and the resulting mixture was heated under reflux for 4 hours. At the end of this time, the reaction mixture was poured into water, after which it was extracted with ethyl acetate. The extract was washed with an aqueous solution of sodium chloride and dried over anhydrous sodium sulfate. The solvent was then removed by distillation under reduced pressure, to give 4.30 g of the title compound, melting at 92.8–95.2° C.

PREPARATION 24

5-[4-(1-Methylindol-2-ylmethoxy)benzyl]-3-triphenylmethylthiazolidine-2,4-dione

A procedure similar to that described in Preparation 4 was repeated, except that 4.30 g of 1-methylindol-2-ylmethanol (prepared as described in Preparation 23), 10.3 g of 5-(4-hydroxybenzyl)-3-triphenylmethylthiazolidine-2,4-dione, 6.65 ml of tributylphosphine, 6.73 g of 1,1'-(azodicarbonyl)dipiperidine and 120 ml of benzene were used, to give 6.28 g of the title compound, melting at 134.3–136.0° C.

PREPARATION 25

Ethyl imidazo[1,2-a]pyridin-2-ylacetate

A solution of 14.6 g of 2-aminopyridine and 25.5 g of ethyl 4-chloroacetoacetate in 200 ml of acetonitrile was heated under reflux for 14.5 hours. At the end of this time, the reaction mixture was freed from the solvent by distillation under reduced pressure. The residue thus obtained was mixed with an aqueous solution of potassium carbonate, after which it was extracted with ethyl acetate. The extract was washed with an aqueous solution of sodium chloride and dried over anhydrous sodium sulfate, after which the solvent was removed by distillation under reduced pressure. The residue was purified by column chromatography through silica gel, using ethyl acetate as the eluent, to give 2.65 g of the title compound having Rf=0.33 (on silica gel thin layer chromatography using ethyl acetate as the developing solvent).

PREPARATION 26

2-(2-Hydroxyethyl)imidazo[1,2-a]pyridine

A procedure similar to that described in Preparation 2 was repeated, except that 2.65 g of ethyl imidazo[1,2-a]pyridin-2-ylacetate (prepared as described in Preparation 25), 0.5 g of lithium aluminum hydride and 100 ml of tetrahydrofuran were used, to give the title compound as a crude product. This crude product was purified by column chromatography through silica gel, using a gradient elution method, with mixtures of ethyl acetate and ethanol in ratios ranging from 20:1 to 4:1 by volume as the eluent, to give 1.32 g of the title compound, melting at 120.3–126.9° C.

PREPARATION 27

5-[4-{2-(Imidazor[1,2-a]pyridin-2-yl)ethoxy}benzyl]-3-triphenylmethylthiazolidine-2,4-dione A procedure similar to that described in Preparation 4 was repeated, except that 0.80 g of 2-(2-hydroxyethyl)imidazo[1,2-a]pyridine (prepared as described in Preparation 26), 2.79 g of 5-(4-hydroxybenzyl)-3-triphenylmethylthiazolidine-2,4-dione, 1.7 ml of tributylphosphine, 1.51 g of 1,1'-(azodicarbonyl)dipiperidine and 30 ml of benzene were used, to give the title compound as a crude product. This crude product was purified by column chromatography through silica gel, using a gradient elution method, with mixtures of hexane and ethyl acetate in ratios ranging from 1:4 to 0:1 by volume as the eluent, to give 0.97 g of the title compound, melting at 135.5–142.4° C. (with decomposition).

PREPARATION 28

3-Ethyl-2-hydroxymethylimidazo[5,4-b]pyridine 3 g of 2-hydroxymethyl-3H-imidazo[5,4-b]pyridine were added to a suspension of 0.87 g of sodium hydride (as a 55% by weight dispersion in mineral oil, and which had previously been washed with hexane) in 80 ml of dimethylformamide, and the resulting mixture was stirred at room temperature for 2 hours. After that, 1.78 ml of ethyl iodide were added dropwise to the mixture while cooling with ice, and the resulting mixture was stirred at room temperature for 2 hours, after which it was allowed to stand overnight. At the end of this time, the reaction mixture was freed from dimethylformamide by distillation under reduced pressure. The residue was purified by column chromatography through silica gel, using a gradient elution method, with mixtures of ethyl acetate and ethanol in ratios ranging from 1:0 to 5:1 by volume as the eluent, to give 570 mg of the title compound, melting at 117–121° C.

PREPARATION 29

5-{4-(3-Ethylimidazo[5,4-b]pyridin-2-ylmethoxy)-benzyl}-3-triphenylmethylthiazolidine-2,4-dione A procedure similar to that described in Preparation 4 was repeated, except that 0.5 g of 3-ethyl-2-hydroxymethylimidazo[5,4-b]pyridine (prepared as described in Preparation 28), 1.313 g of 5-(4-hydroxybenzyl)-3-triphenylmethylthiazolidine-2,4-dione, 0.77 ml of tributylphosphine, 0.712 g of 1,1'-(azodicarbonyl)dipiperidine and 80 ml of benzene were used, to give the title compound as a crude product. This crude product was purified by column chromatography through silica gel, using a 1:3 by volume mixture of hexane and ethyl acetate as the eluent, to give 300 mg of the title compound having Rf=0.55 (on silica gel thin layer chromatography using a 1:3 by volume mixture of hexane and ethyl acetate as the developing solvent).

PREPARATION 30

2-Hydroxymethyl-1-methylimidazo[4,5-b]pyridine

A procedure similar to that described in Preparation 15 was repeated, except that 45 g of 2-hydroxymethyl-3H- imidazo[5,4-b]pyridine, 13.17 g of sodium hydride (as a 55% by weight dispersion in mineral oil), 20.7 ml of methyl iodide and 1.43 liter of dimethylformamide were used, to give the title compound as a crude product. This crude product was purified by column chromatography through silica gel, using a gradient elution method, with mixtures of ethyl acetate and methanol in ratios ranging from 1:0 to 1:1 by volume as the eluent, to give 3.24 g of the title compound, melting at 130–132° C.

PREPARATION 31

5-{4-(1-Methylimidazo[4,5-b]pyridin-2-ylmethoxy) benzyl}-3-triphenylmethylthiazolidine-2,4-dione A procedure similar to that described in Preparation 4 was repeated, except that 2.5 g of 2-hydroxymethyl-1-methylimidazo[4,5-b]pyridine (prepared as described in Preparation 30), 6.5 g of 5-(4-hydroxybenzyl)-3-triphenylmethylthiazolidine-2,4-dione, 3.47 ml of tributylphosphine, 3.52 g of 1,1'-(azodicarbonyl) dipiperidine and 250 ml of 1,4-dioxane were used, to give the title compound as a crude product. This crude product was purified by column chromatography through silica gel, using a gradient elution method, with mixtures of hexane and ethyl acetate in ratios ranging from 1:1 to 0:1 by volume and subsequently mixtures of ethyl acetate and methanol in ratios ranging from 20:1 to 10:1 by volume as the eluent, to give 4.1 g of the title compound.

PREPARATION 32

4-Hydroxybutyric acid

A 2 N aqueous solution of sodium hydroxide was added to a solution of 10.0 g of γ-butyrolactone in 100 ml of methanol, and the resulting mixture was allowed to stand overnight. At the end of this time, the reaction mixture was neutralized by adding 2 N aqueous hydrochloric acid, after which it was extracted with ethyl acetate. The extract was washed with an aqueous solution of sodium chloride and dried over anhydrous sodium sulfate. The solvent was then removed by distillation under reduced pressure, to give 3.70 g of the title compound as an oil.

PREPARATION 33

2-(3-Hydroxypropyl)-3H-imidazo[5,4-b]pyridine 0.83 g of 4-hydroxybutyric acid (prepared as described in Preparation 32) was added to 0.77 g of 2,3-diaminopyridine, and the resulting mixture was stirred at 150° C. for 4 hours. At the end of this time, the reaction mixture was treated with 3 N aqueous hydrochloric acid and subsequently made alkaline by the addition of aqueous ammonia. The aqueous mixture was evaporated to dryness under reduced pressure, and then the resulting residue was purified by column chromatography through silica gel, using a 5:1 by volume mixture of ethyl acetate and methanol as the eluent. The product was crystallized by trituration with ethyl acetate, to give 0.83 g of the title compound, melting at 151–153° C.

PREPARATION 34

2-(3-Hydroxypropyl)-3-methylimidazo[5,4-b] pyridine

A procedure similar to that described in Preparation 15 was repeated, except that 3.40 g of 2-(3-hydroxypropyl)-3H-imidazo[5,4-b]pyridine (prepared as described in Preparation 33), 0.81 g of sodium hydride (as a 55% by weight dispersion in mineral oil), 1.2 ml of methyl iodide and 100 ml of dimethylformamide were used, to give the title compound as a crude product. This crude product was purified by column chromatograpy through silica gel, using a 10:1 by volume mixture of ethyl acetate and methanol as the eluent. The product was crystallized by trituration with ethyl acetate, to give 3.10 g of the title compound, melting at >300° C.

PREPARATION 35

5-[4-{3-(3-Methylimidazo[5,4-b]pyridin-2-yl) propoxy}benzyl]-3-triphenylmethylthiazolidine-2,4-dione A procedure similar to that described in Preparation 4 was repeated, except that 750 mg of 2-(3-hydroxypropyl)-3-methylimidazo[5,4-b]pyridine (prepared as described in Preparation 34), 1.83 g of 5-(4-hydroxybenzyl)-3-triphenylmethylthiazolidine-2,4-dione, 0.98 ml of tributylphosphine, 990 mg of 1,1'-(azodicarbonyl) dipiperidine and 20 ml of toluene were used, to give the title compound as a crude product. This crude product was purified by column chromatography through silica gel, using a gradient elution method, with mixtures of hexane and ethyl acetate in ratios ranging from 1:1 to 0:1 by volume as the eluent, to give 550 mg of the title compound, melting at 76–81° C.

PREPARATION 36

Methyl 4-nitrophenoxyacetate

A solution of 56 g of 4-nitrophenol, 90 g of methyl bromoacetate and 100 g of potassium carbonate in 500 ml of dimethylformamide was stirred at room temperature for 2 days. At the end of this time, the reaction mixture was freed from dimethylformamide by distillation under reduced pressure. The residue thus obtained was diluted with water, after which it was extracted with ethyl acetate. The extract was washed with water and dried over anhydrous sodium sulfate, after which the solvent was removed by distillation under reduced pressure. The resulting residue was crystallized by trituration with hexane, to give 63.3 g of the title compound, melting at 98–99° C.

PREPARATION 37

Methyl 4-aminophenoxyacetate

A procedure similar to that described in Example 6 was repeated, except that 30.8 g of methyl 4-nitrophenoxyacetate (prepared as described in Preparation 36), 5.0 g of 10% w/w palladium-on-charcoal and 500 ml of methanol were used, to give 25.8 g of the title compound having Rf=0.79 (on silica gel thin layer chromatography using ethyl acetate as the developing solvent).

PREPARATION 38

Methyl 4-(2-bromo-2-butoxycarbonylethyl) phenoxyacetate 99 g of 47% w/v aqueous hydrobromic acid and subsequently 33 ml of an aqueous solution containing 12.8 g of sodium nitrite were added dropwise to a solution of 25.8 g of methyl 4-aminophenoxyacetate (prepared as described in Preparation 37) in 263 ml of a 2:5 by volume mixture of methanol and acetone, whilst cooling with ice, and the resulting mixture was stirred for 30 minutes whilst cooling with ice. 18.2 g of butyl acrylate were then added. The mixture was then stirred for 30 minutes while cooling with ice, after which 3.2 g of copper(I) bromide were added and the resulting mixture was stirred overnight at room temperature. At the end of this time, the reaction mixture was freed from the solvent by distillation under reduced pressure. The residue was diluted with an aqueous solution of sodium chloride and extracted with ethyl acetate. The extract was washed with an aqueous solution of sodium chloride and dried over anhydrous sodium sulfate, after which the solvent was removed by distillation under reduced pressure, to give 51.7 g of a crude product containing the title compound and having Rf=0.46 (on silica gel thin layer chromatography using a 5:1 by volume mixture of hexane and ethyl acetate as the developing solvent).

PREPARATION 39

5-[4-(Ethoxycarbonylmethoxy)benzyl]-thiazolidine-2,4-dione

A solution of 100 g of methyl 4-(2-bromo-2-butoxycarbonylethyl)phenoxyacetate (prepared as described in Preparation 38) and 22 g of thiourea in 200 ml of ethanol was heated under reflux for 2.5 hours. After that, 2 N aqueous hydrochloric acid was added to the mixture, and the resulting mixture was heated under reflux for 5 hours. At the end of this time, the reaction mixture was freed from the solvent by distillation under reduced pressure. The resulting residue was diluted with water, after which it was extracted with ethyl acetate. The extract was dried over anhydrous magnesium sulfate, and the solvent was removed by distillation under reduced pressure. The resulting residue was purified by column chromataography through silica gel, using a 2:5 by volume mixture of ethyl acetate and hexane as the eluent, to give 19.4 g of the title compound, melting at 105–106° C.

PREPARATION 40

3,7-Dimethyl-2-hydroxymethylimidazo[5,4-b] pyridine

A procedure similar to that described in Preparation 15 was repeated, except that 5.00 g of 2-hydroxymethyl-7-methyl-3H-imidazo[5,4-b]pyridine, 1.34 g of sodium hydride (as a 55% by weight dispersion in mineral oil), 2.0 ml of methyl iodide and 120 ml of dimethylformamide were used, to give the title compound as a crude product. This crude product was purified by column chromatography through silica gel, using a gradient elution method, with mixtures of ethyl acetate and methanol in ratios ranging from 1:0 to 10:1 by volume as the eluent, to give 4.4 g of the title compound, melting at >300° C.

PREPARATION 41

5-{4-(3,7-Dimethylimidazo[5,4-b]pyridin-2-ylmethoxy)benzyl}-3-triphenylmethylthiazolidine-2,4-dione A procedure similar to that described in Preparation 4 was repeated, except that 1.50 g of 3,7-dimethyl-2-hydroxymethylimidazo[5,4-b]pyridine (prepared as described in Preparation 40), 3.94 g of 5-(4-hydroxybenzyl)-3-triphenylmethylthiazolidine-2,4-dione, 2.11 ml of tributylphosphine, 2.14 g of 1,1'-(azodicarbonyl) dipiperidine and 30 ml of toluene were used, to give the title compound as a crude product. This crude product was purified by column chromatography through silica gel, using a gradient elution method, with mixtures of hexane and ethyl acetate in ratios ranging from 1:1 to 1:2 by volume as the eluent, to give 1.11 g of the title compound, melting at 92–105° C. (softening).

PREPAPATION 42

6-Chloro-2,3-diaminopyridine

A mixture of 12.0 g of 2-amino-6-chloro-3-nitropyridine, 78.0 g of tin(II) chloride dihydrate and 360 ml of a 9:1 by volume mixture of ethyl acetate and 2-methyl-2-propanol was stirred at 60° C. for 1 hour, after which 1.32 g of sodium borohydride were added at 60° C., and the mixture was stirred for 3 hours at the same temperature. At the end of this time, the reaction mixture was freed from the solvent by distillation under reduced pressure. The resulting residue was diluted with water and neutralized by adding an aqueous solution of potassium carbonate, after which it was extracted with ethyl acetate. The extract was washed with an aqueous solution of sodium chloride and dried over anhydrous sodium sulfate, after which the solvent was removed by distillation under reduced pressure. The residue thus obtained was crystallized by trituration with a mixture of ethyl acetate and hexane, to give 6.50 g of title compound, melting at 120–122° C.

PREPARATION 43

5-Chloro-2-hydroxymethyl-3H-imidazo[5,4-b] pyridine 6.60 g of glycolic acid were added to 5.00 g of 6-chloro-2,3-diaminopyridine (prepared as described in Preparation 42), and the resulting mixture was stirred at 150° C. for 4 hours. At the end of this time, the reaction mixture was treated with 3 N aqueous hydrochloric acid and subsequently made alkaline by the addition of aqueous ammonia. The aqueous mixture was evaporated to dryness, and the resulting residue was purified by column chromatography through silica gel, using a gradient elution method, with mixtures of ethyl acetate and methanol in ratios ranging from 1:0 to 10:1 by volume as the eluent. The product was then crystallized by trituration with ethyl acetate, to give 5.33 g of the title compound, melting at 224–226° C.

PREPARATION 44

5-Chloro-2-hydroxymethyl-3-methylimidazo[5,4-b] pyridine

A procedure similar to that described in Preparation 15 was repeated, except that 3.00 g of 5-chloro-2-hydroxymethyl-3H-imidazo[5,4-b]pyridine (prepared as described in Preparation 43), 0.71 g of sodium hydride (as a 55 by weight dispersion in mineral oil), 1.1 ml of methyl iodide and 70 ml of dimethylformamide were used, to give the title compound as a crude product. This crude product was purified by column chromatography through silica gel, using a gradient elution method, with mixtures of ethyl acetate and methanol in ratios ranging from 1:0 to 10:1 by volume as the eluent, to give 1.60 g of the title compound, melting at 204–210° C.

PREPARATION 45

5-{4-(5-Chloro-3-methylimidazo[5,4-b]pyridin-2-ylmethoxy)benzyl}-3-triphenylmethylthiazolidine-2,4-dione A procedure similar to that described in Preparation 4 was repeated, except that 1.20 g of 5-chloro-2-hydroxymethyl- 3-methylimidazo[5,4-b]pyridine (prepared as described in Preparation 44), 2.83 g of 5-(4-hydroxybenzyl)-3-triphenylmethylthiazolidine-2,4-dione, 1.51 ml of tributylphosphine, 1.53 g of 1,1'-(azodicarbonyl) dipiperidine and 25 ml of toluene were used, to give the title compound as a crude product. This crude product was purified by column chromatography through silica gel, using a gradient elution method, with mixtures of hexane and ethyl acetate in ratios ranging from 2:1 to 1:1 by volume as the eluent, to give 1.29 g of the title compound, melting at 97–99° C. (softening).

PREPARATION 46

5-[4-(2,2-Diethoxyethoxy)benzyl]thiazolidine-2,4-dione 530 mg of 5-(4-hydroxybenzyl)thiazolidine-2,4-dione were added to a suspension of 260 mg of sodium hydride (as a 55% by weight dispersion in mineral oil, and which had previously been washed with toluene) in 5 ml of dimethylformamide, whilst cooling with ice, and the resulting mixture was stirred at room temperature for 30 minutes. At the end of this time, 0.73 ml of bromoacetaldehyde diethyl acetal was added to the mixture, whilst cooling with ice, and the resulting mixture was stirred at 50° C. for 3 hours. The reaction mixture was freed from dimethylformamide by distillation under reduced pressure. The resulting residue was diluted with water and the aqueous mixture was adjusted to a pH of from 2 to 3 by the addition of 1 N aqueous hydrochloric acid, after which it was extracted with ethyl acetate. The extract was washed with a saturated aqueous solution of sodium chloride and dried over anhydrous sodium sulfate, after which the solvent was removed by distillation under reduced pressure. The resulting residue was purified by column chromatography through silica gel, using a 2:1 by volume mixture of hexane and ethyl acetate as the eluent, to give 600 mg of the title compound having Rf=0.46 (on silica gel thin layer chromatography using a 2:1 by volume mixture of hexane and ethyl acetate as the developing solvent).

PREPARATION 47

5-[4-(2-Oxoethoxy)benzyl]thiazolidine-2,4-dione 20 ml of 6 N aqueous hydrochloric acid were added to a solution of 10.07 g of 5-[4-(2,2-diethoxyethoxy)benzyl] thiazolidine-2,4-dione (prepared as described in Preparation 46) in 80 ml of tetrahydrofuran, and the resulting mixture was allowed to stand overnight at room temperature. At the end of this time, the reaction mixture was freed from the solvent by distillation under reduced pressure. The residue was diluted with water, after which it was extracted with ethyl acetate. The extract was dried over anhydrous sodium sulfate and the solvent was removed by distillation under reduced pressure. The resulting residue was purified by column chromatography through silica gel, using a 2:3 by volume mixture of hexane and ethyl acetate as the eluent, to give 5.92 g of the title compound having Rf=0.37 (on silica gel thin layer chromatography using a 1:2 by volume mixture of hexane and ethyl acetate as the developing solvent).

PREPARATION 48

2-Hydroxymethyl-3H-imidazo[5,4-d]pyrimidine 8.58 g of ethyl glycolate were added to 2.27 g of 4,5-diaminopyrimidine, and the resulting mixture was stirred at 140° C. for 2 hours. At the end of this time, the reaction mixture was freed from ethyl glycolate by distillation under reduced pressure. The residue thus obtained was decolorized by activated charcoal and crystallized by trituration with ethanol, to give 1.81 g of the title compound having Rf=0.27 (on silica gel thin layer chromatography using a 10:1 by volume mixture of ethyl acetate and methanol as the developing solvent).

PREPARATION 49

2-t-Butyldimethylsilyloxymethyl-3H-imidazo[5,4-d] pyrimidine

A mixture of 1.81 g of 2-hydroxymethyl-3H-imidazo-[5,4-d]pyrimidine (prepared as described in Preparation 48), 2.71 g of t-butyldimethylsilyl chloride, 2.45 g of imidazole and 100 ml of dimethylformamide was stirred at room temperature for 1 hour. At the end of this time, the reaction mixture was freed from dimethylformamide by distillation under reduced pressure. The residue thus obtained was diluted with water, after which it was extracted with ethyl acetate. The extract was washed with an aqueous solution of sodium chloride and dried over anhydrous sodium sulfate, after which the solvent was removed by distillation under reduced pressure. The resulting residue was purified by column chromatography through silica gel, using ethyl acetate as the eluent, to give 1.89 g of the title compound, melting at 104–107° C.

PREPARATION 50

2-Hydroxymethyl-3-methylimidazo[5,4-d] pyrimidine

A procedure similar to that described in Preparation 15 was repeated, except that 1.89 g of 2-t-butyl-dimethylsilyloxymethyl-3H-imidazo[5,4-d]pyrimidine (prepared as described in Preparation 49), 0.37 g of sodium hydride (as a 55% by weight dispersion in mineral oil), 490 μl of methyl iodide and 30 ml of dimethylformamide were used. At the end of this time, the reaction mixture was freed from dimethylformamide by distillation under reduced pressure. The residue thus obtained was treated with 3 N aqueous hydrochloric acid and subsequently made alkaline by the addition of aqueous ammonia. The aqueous mixture was evaporated to dryness, and the resulting residue was purified by column chromatography through silica gel, using a 6:1 by volume mixture of ethyl acetate and ethanol as the eluent, to give 0.37 g of the title compound, melting at 122–125° C.

PREPARATION 51

5-{4-(3-Methylimidazo[5,4-d]pyrimidin-2-ylmethoxy)-benzyl}-3-triphenylmethylthiazolidine-2,4-dione A procedure similar to that described in Preparation 4 was repeated, except that 0.37 g of 2-hydroxymethyl-3-methylimidazo[5,4-d]pyrimidine (prepared as described in Preparation 50), 2.51 g of 5-(4-hydroxybenzyl)-3-triphenylmethylthiazolidine-2,4 dione, 1.34 ml of tributylphosphine, 1.36 g of 1,1'-(azodicarbonyl) dipiperidine and 50 ml of benzene were used, to give the title compound as a crude product. This crude product was purified by column chromatography through silica gel, using a gradient elution method, with mixtures of hexane and ethyl acetate in a ratio of 2:1 by volume, and then in ratios ranging from 1:1 to 1:2 by volume, and subsequently a 6:1 by volume mixture of ethyl acetate and ethanol as the eluent. The desired fractions were collected and concentrated by evaporation under reduced pressure. The concentrate was further purified by preparative reverse-phase high speed liquid chromatography through YMC-Pack ODS-A (a product of YMC Inc.) using a 100:100:1:1 by volume mixture of acetonitrile, water, acetic acid and triethylamine as the eluent, to give 0.24 g of the title compound, melting at 55–65° C. (softening).

PREPARATION 52

2-(4-Chlorobenzyl)amino-3-nitropyridine

A mixture of 10.3 g of 2-hydroxy-3-nitropyridine and 25.5 ml of thionyl chloride was heated under reflux for 2.5 hours, after which 1.1 ml of dimethylformamide were rapidly added to the mixture, which was then heated under reflux for 2.5 hours. At the end of this time, the reaction mixture was freed from the solvent by evaporation under reduced pressure. 80 ml of toluene and 19.1 g of sodium carbonate were added to the residue thus obtained, and then a solution of 12.3 ml of 4-chlorobenzylamine in 20 ml of toluene was added dropwise to the resulting mixture, which was then stirred at 85° C. for 4 hours. At the end of this time, the insoluble material in the reaction mixture was removed by filtration. The filtrate was washed with water and dried over anhydrous sodium sulfate, after which the solvent was removed by distillation under reduced pressure. The resulting residue was crystallized by trituration with 2-propanol, to give 12.0 g of the title compound, melting at 95–96° C.

PREPARATION 53

3-Amino-2-(4-chlorobenzyl)aminopyridine

A procedure similar to that described in Preparation 42 was repeated, except that 5.00 g of 2-(4-chlorobenzyl)amino-3-nitropyridine (prepared as described in Preparation 52), 21.4 g of tin(II) chloride dihydrate, 0.36 g of sodium borohydride and 150 ml of a 9:1 by volume mixture of ethyl acetate and 2-methyl-2-propanol were used, to give the title compound as a crude product. This crude product was crystallized by trituration with a mixture of ethyl acetate and hexane, to give 3.55 g of the title compound, melting at 123–125° C.

PREPARATION 54

2-Hydroxymethyl-3-(4-phenylbenzyl)imidazo[5,4-b]pyridine 3.74 g of 2-hydroxymethyl-3H-imidazo[5,4-b]pyridine were added to a suspension of 1.1 g of sodium hydride (as a 55% by weight dispersion in mineral oil, and which had previously been washed with hexane) in 100 ml of dimethylformamide, and the resulting mixture was stirred at room temperature for 2 hours. After that, a solution of 5.07 g of 4-(chloromethyl)biphenyl in 20 ml of dimethylformamide was added dropwise to the mixture, whilst cooling with ice, and the resulting mixture was stirred at room temperature for 2 hours. It was then allowed to stand overnight. At the end of this time, the reaction mixture was freed from dimethylformamide by distillation under reduced pressure. The resulting residue was purified by column chromatography through silica gel, using a 1:3 by volume mixture of hexane and ethyl acetate as the eluent, to give 0.8 g of the title compound, melting at 163–165° C.

PREPARATION 55

5-[4-{3-(4-Phenylbenzyl)imidazo[5,4-b]pyridin-2-ylmethoxy}benzyl]-3-triphenylmethylthiazolidine-2,4-dione A procedure similar to that described in Preparation 4 was repeated, except that 0.5 g of 2-hydroxymethyl-3-(4-phenylbenzyl)imidazo[5,4-b]pyridine (prepared as described in Preparation 54), 0.738 g of 5-(4-hydroxybenzyl)-3-triphenylmethylthiazolidine-2,4-dione, 0.43 ml of tributylphosphine, 0.4 g of 1,1'-(azodicarbonyl)dipiperidine and 20 ml of benzene were used, to give the title compound as a crude product. This crude product was purified by column chromatography through silica gel, using a gradient elution method, with mixtures of hexane and ethyl acetate in ratios ranging from 1:2 to 1:3 by volume as the eluent, to give 0.95 g of the title compound having Rf=0.44 (on silica gel thin layer chromatography using a 1:3 by volume mixture of hexane and ethyl acetate as the developing solvent).

PREPARATION 56

2-Amino-5-bromo-3-nitropyridine 100 ml of concentrated sulfuric acid were added to 25.0 g of 2-amino-5-bromopyridine, and 8.9 ml of concentrated nitric acid were then added dropwise to the mixture at a temperature of 50 to 60° C. over a period of 1 hour. The mixture was then stirred at 60° C. for 30 minutes. At the end of this time, the reaction mixture was poured into ice-water and neutralized by the addition of an aqueous solution of sodium hydroxide. The crystals which precipitated were collected by filtration and washed with ethanol, to give 19.1 g of the title compound, melting at 180–182° C.

PREPARATION 57

5-Bromo-2,3-diaminopyridine

A procedure similar to that described in Preparation 42 was repeated, except that 12.0 g of 2-amino-5-bromo-3-nitropyridine (prepared as described in Preparation 56), 62.1 g of tin(II) chloride dihydrate, 1.04 g of sodium borohydride and 300 ml of a 9:1 by volume mixture of ethyl acetate and 2-methyl-2-propanol were used, to give the title compound as a crude product. This crude product was crystallized by trituration with a mixture of ethyl acetate and hexane, to give 7.46 g of the title compound, melting at 135–137° C.

PREPARATION 58

6-Bromo-2-hydroxymethyl-3H-imidazo[5,4-b]pyridine

A procedure similar to that described in Preparation 43 was repeated, except that 7.00 g of 5-bromo-2,3-diaminopyridine (prepared as described in Preparation 57) and 8.50 g of glycolic acid were used, to give the title compound as a crude product. This crude product was purified by column chromatography through silica gel, using a 10:1 by volume mixture of ethyl acetate and methanol as the eluent, to give 7.05 g of the title compound, melting at 230–233° C.

PREPARATION 59

6-Bromo-2-hydroxymethyl-3-methylimidazo[5,4-b]pyridine

A procedure similar to that described in Preparation 15 was repeated, except that the reaction was conducted using 3.00 g of 6-bromo-2-hydroxymethyl-3H-imidazo-[5,4-b]pyridine (prepared as described in Preparation 58), 0.58 g of sodium hydride (as a 55% by weight dispersion in mineral oil), 0.92 ml of methyl iodide and 60 ml of dimethylformamide. After completion of the reaction with methyl iodide, the reaction mixture was freed from dimethylformamide by distillation under reduced pressure. The residue was diluted with water, after which it was extracted with ethyl acetate. The extract was washed with an aqueous solution of sodium chloride and dried over anhydrous sodium sulfate, after which the solvent was removed by distillation under reduced pressure. The resulting residue was purified by column chromatography through silica gel, using a 50:1 by volume mixture of ethyl acetate and methanol as the eluent, to give 1.40 g of the title compound, melting at 142–144° C.

PREPARATION 60

5-{4-(6-Bromo-3-methylimidazo[5,4-b]pyridin-2-ylmethoxy)benzyl}-3-triphenylmethylthiazolidine-2,4-dione A procedure similar to that described in Preparation 4 was repeated, except that 1.35 g of 6-bromo-2-hydroxymethyl-3-methylimidazo[5,4-b]pyridine (prepared as described in Preparation 59), 2.60 g of 5-(4-hydroxybenzyl)-3-triphenylmethylthiazolidine-2,4-dione, 1.39 ml of tributylphosphine, 1.41 g of 1,1'-(azodicarbonyl)dipiperidine and 35 ml of toluene were used, to give the title compound as a crude product. This crude product was purified by column chromatography through silica gel, using a 1:1 by volume mixture of hexane and ethyl acetate as the eluent, to give 3.43 g of the title compound, melting at 97–100° C. (softening).

PREPARATION 61

2-Amino-5-chloro-3-nitropyridine

A procedure similar to that described in Preparation 56 was repeated, except that 25.0 g of 2-amino-5-chloropyridine, 100 ml of concentrated sulfuric acid and 12.5 ml of concentrated nitric acid were used, to give 18.5 g of the title compound, melting at 138–139° C.

PREPARATION 62

5-Chloro-2,3-diaminopyridine

A procedure similar to that described in Preparation 42 was repeated, except that 12.5 g of 2-amino-5-chloro-3-nitropyridine (prepared as described in Preparation 61), 82.0 g of tin(II) chloride dihydrate, 1.35 g of sodium borohydride and 300 ml of a 9:1 by volume mixture of ethyl acetate and 2-methyl-2-propanol were used, to give the title compound as a crude product. This crude product was crystallized by trituration with a mixture of ethyl acetate and hexane, to give 8.14 g of the title compound, melting at 164–165° C.

PREPARATION 63

6-Chloro-2-hydroxymethyl-3H-imidazo[5,4-b]pyridine

A procedure similar to that described in Preparation 43 was repeated, except that 7.67 g of 5-chloro-2,3-diaminopyridine (prepared as described in Preparation 62) and 18.6 g of glycolic acid were used, to give the title compound as a crude product. This crude product was purified by column chromatography through silica gel, using a 10:1 by volume mixture of ethyl acetate and methanol as the eluent, to give 8.83 g of the title compound, melting at 209–211° C.

PREPARATION 64

6-Chloro-2-hydroxymethyl-3-methylimidazo[5,4-b]pyridine

A procedure similar to that described in Preparation 59 was repeated, except that 3.00 g of 6-chloro-2-hydroxymethyl-3H-imidazo[5,4-b]pyridine (prepared as described in Preparation 63), 0.71 g of sodium hydride (as a 55% by weight dispersion in mineral oil), 1.03 ml of methyl iodide and 50 ml of dimethylformamide were used, to give the title compound as a crude product. This crude product was purified by column chromatography through silica gel, using a gradient elution method, with mixtures of ethyl acetate and methanol in ratios ranging from 1:0 to 50:1 by volume as the eluent, to give 0.87 g of the title compound, melting at 141–142° C.

PREPARATION 65

5-{4-(6-Chloro-3-methylimidazo[5,4-b]pyridin-2-ylmethoxy)benzyl}-3-triphenylmethylthiazolidine-2,4-dione A procedure similar to that described in Preparation 4 was repeated, except that 0.52 g of 6-chloro-2-hydroxymethyl-3-methylimidazo[5,4-b]pyridine (prepared as described in Preparation 64), 1.23 g of 5-(4-hydroxybenzyl)-3-triphenylmethylthiazolidine-2,4-dione, 0.66 ml of tributylphosphine, 0.67 g of 1,1'-(azodicarbonyl)dipiperidine and 20 ml of toluene were used, to give the title compound as a crude product. This crude product was purified by column chromatography through silica gel, using a 1:1 by volume mixture of hexane and ethyl acetate as the eluent, to give 1.51 g of the title compound, melting at 82–84° C. (softening).

PREPARATION 66

6-Chloro-2-methylamino-3-nitropyridine 20.0 ml of a 30% ethanolic solution of methylamine were added dropwise to a mixture of 29.0 g of 2,6-dichloro-3-nitropyridine, 300 ml of ethanol and 36.6 g of sodium carbonate, whilst cooling with ice, and the resulting mixture was stirred at room temperature for 8 hours. At the end of this time, the reaction mixture was freed from ethanol by distillation. The residue was diluted with water, after which it was extracted with ethyl acetate. The extract was washed with an aqueous solution of sodium chloride and dried over anhydrous sodium sulfate, after which the solvent was removed by distillation under reduced pressure. The residue was crystallized by trituration with ethanol, to give 22.3 g of the title compound, melting at 114° C.

PREPARATION 67

6-Methoxy-2-methylamino-3-nitropyridine 19 ml of a 28% methanolic solution of sodium methoxide were added dropwise to a solution of 6.00 g of 6-chloro-2-methylamino-3-nitropyridine (prepared as described in Preparation 66) in 120 ml of methanol at room temperature, and the resulting mixture was stirred at room temperature for 3 hours. At the end of this time, the reaction mixture was poured into water, after which it was extracted with ethyl acetate. The extract was washed with an aqueous solution of sodium chloride and dried over anhydrous sodium sulfate, after which the solvent was removed by distillation under reduced pressure. The residue was crystallized by trituration with ethanol, to give 5.34 g of the title compound, melting at 152–153° C.

PREPARATION 68

3-Amino-6-methoxy-2-methylaminopyridine

A procedure similar to that described in Example 6 was repeated, except that 3.45 g of 6-methoxy-2-methylamino- 3-nitropyridine (prepared as described in Preparation 67), 0.70 g of 10% w/w palladium-on-charcoal and 50 ml of dioxane were used, to give 2.66 g of the title compound having Rf=0.12 (on silica gel thin layer chromatography using a 1:1 by volume mixture of hexane and ethyl acetate as the developing solvent).

PREPARATION 69

2-Hydroxymethyl-5-methoxy-3-methylimidazo[5,4-b]pyridine

A solution of 2.20 g of 3-amino-6-methoxy-2-methylaminopyridine (prepared as described in Preparation 68) and 3.30 g of glycolic acid in 40 ml of toluene was heated under reflux for 4 hours. At the end of this time, the reaction mixture was poured into water, after which it was extracted with ethyl acetate. The extract was washed with an aqueous solution of sodium chloride and dried over anhydrous sodium sulfate, after which the solvent was removed by distillation under reduced pressure. The residue was purified by column chromatography through silica gel, using a 30:1 by volume mixture of ethyl acetate and methanol as the eluent, to give 620 mg of the title compound, melting at 138–140° C.

PREPARATION 70

5-{4-(5-Methoxy-3-methylimidazo[5,4-b]pyridin-2-ylmethoxy)benzyl}-3-triphenylmethylthiazolidine-2.4-dione A procedure similar to that described in Preparation 4 was repeated, except that 0.25 g of 2-hydroxymethyl-5-methoxy-3-methylimidazo[5,4-b]pyridine (prepared as described in Preparation 69), 0.66 g of 5-(4-hydroxybenzyl)-3-triphenylmethylthiazolidine-2,4-dione, 0.35 ml of tributylphosphine, 0.36 g of 1,1'-(azodicarbonyl)dipiperidine and 15 ml of toluene were used, to give the title compound as a crude product. This crude product was purified by column chromatography through silica gel, using a 1:1 by volume mixture of hexane and ethyl acetate as the eluent, to give 0.70 g of the title compound, melting at 80–85° C. (softening).

PREPARATION 71

2-t-Butyldimethylsilyloxymethyl-1H-imidazo[4,5-c]pyridine

A procedure similar to that described in Preparation 49 was repeated, except that 5.00 g of 2-hydroxymethyl-1H-imidazo[4,5-c]pyridine, 6.85 g of imidazole, 7.58 g of t-butyldimethylsilyl chloride and 100 ml of dimethylformamide were used, to give the title compound as a crude product. This crude product was purified by column chromatography through silica gel, using a 10:1 by volume mixture of ethyl acetate and methanol as the eluent, to give 7.40 g of the title compound, melting at 53–55° C.

PREPARATION 72

2-t-Butyldimethylsilyloxymethyl-1-methylimidazo[4,5-c]pyridine

A procedure similar to that described in Preparation 59 was repeated, except that 7.4 g of 2-t-butyldimethylsilyloxymethyl-1H-imidazo[4,5-c]pyridine (prepared as described in Preparation 71), 1.23 g of sodium hydride (as a 55% by weight dispersion in mineral oil), 2.0 ml of methyl iodide and 200 ml of dimethylformamide were used, to give the title compound as a crude product. This crude product was purified by column chromatography through silica gel, using a 10:1 by volume mixture of ethyl acetate and methanol as the eluent, to give 3.30 g of the title compound, melting at 93–95° C.

PREPARATION 73

2-Hydroxymethyl-1-methylimidazo[4,5-c]pyridine

A solution of 3.00 g of 2-t-butyldimethylsilyloxymethyl-1-methylimidazo[4,5-c]pyridine (prepared as described in Preparation 72) in 60 ml of a 1:1:1 by volume mixture of tetrahydrofuran, acetic acid and water was stirred at room temperature for 1 hour and then at 60° C. for 5 hours. At the end of this time, the reaction mixture was freed from the solvent by distillation. The resulting residue was mixed with an aqueous solution of sodium hydrogencarbonate and then concentrated by evaporation under reduced pressure. The concentrate was purified by column chromatography through silica gel, using a 10:1 by volume mixture of ethyl acetate and methanol as the eluent, to give 1.97 g of the title compound, melting at 285–290° C.

PREPARATION 74

5-{4-(1-Methylimidazo[4,5-c]pyridin-2-ylmethoxy)benzyl}-3-triphenylmethylthiazolidine-2,4-dione A procedure similar to that described in Preparation 4 was repeated, except that 1.94 g of 2-hydroxymethyl-1-methylimidazo[4,5-c]pyridine (prepared as described in Preparation 73), 5.71 g of 5-(4-hydroxybenzyl)-3-triphenylmethylthiazolidine-2,4-dione, 3.1 ml of tributylphosphine, 3.09 g of 1,1'-(azodicarbonyl)dipiperidine and 50 ml of toluene were used, to give the title compound as a crude product. This crude product was purified by column chromatography through silica gel, using a gradient elution method, with mixtures of ethyl acetate and methanol in ratios ranging from 1:0 to 10:1 by volume as the eluent, to give 3.55 g of the title compound having Rf=0.08 (on silica gel thin layer chromatography using ethyl acetate as the developing solvent).

PREPARATION 75

2-Chloro-3-formylpyridine 200 ml of a 1.02 M hexane solution of diisobutylaluminum hydride were added to a solution of 16.7 g of 2-chloro-3-cyanopyridine in 200 ml of tetrahydrofuran at a temperature of −30° to 20° C. over a period of 30 minutes, after which the resulting mixture was stirred at room temperature for 1 hour. At the end of this time, hydrochloric acid was added to the reaction mixture at 0° C., and then the mixture was extracted with ethyl acetate. The extract was washed with a saturated aqueous solution of sodium carbonate and with a saturated aqueous solution of sodium chloride, in that order, and then dried over anhydrous sodium sulfate, after which the solvent was removed by distillation under reduced pressure. The residue was purified by column chromatography through silica gel, using a gradient elution method, with mixtures of hexane and ethyl acetate in ratios ranging from 6:1 to 5:1 by volume as the eluent, to give 7.0 g of the title compound having Rf=0.50 (on silica gel thin layer chromatography using a 2:1 by volume mixture of hexane and ethyl acetate as the developing solvent).

PREPARATION 76

Ethyl 2-azido-3-(2-chloropyridin-3-yl)-3-hydroxypropionate

A mixture of 2.0 g of 2-chloro-3-formylpyridine (prepared as described in Preparation 75), 7.5 g of ethyl azidoacetate and 87 ml of a 65 mM ethanolic solution of sodium ethoxide was stirred at 0° C. for 2 hours. At the end of this time, the reaction mixture was poured into water, after which it was extracted with ethyl acetate. The extract was washed with a saturated aqueous solution of ammonium chloride and a saturated aqueous solution of sodium chloride, in that order, and dried over anhydrous sodium sulfate, after which the solvent was removed by distillation under reduced pressure. The residue was purified by column chromatography through silica gel, using a 3:1 by volume mixture of hexane and ethyl acetate as the eluent, to give 2.83 g of the title compound having Rf=0.61 (on silica gel thin layer chromatography using a 2:1 by volume mixture of hexane and ethyl acetate as the developing solvent).

PREPARATION 77

Ethyl 2-azido-3-t-butyldimethylsilyloxy-3-(2-chloropyridin-3-yl)propionate

A procedure similar to that described in Preparation 49 was repeated, except that 3.90 g of ethyl 2-azido-3-(2-chloropyridin-3-yl)-3-hydroxypropionate (prepared as described in Preparation 76), 8.6 g of t-butyldimethylsilyl chloride, 10 g of imidazole and 80 ml of dimethylformamide were used, to give the title compound as a crude product. This crude product was purified by column chromatography through silica gel, using a 8:1 by volume mixture of hexane and ethyl acetate as the eluent, to give 5.6 g of the title compound having Rf=0.31 (on silica gel thin layer chromatography using a 3:1 by volume mixture of hexane and ethyl acetate as the developing solvent).

PREPARATION 78

Ethyl 2-amino-3-t-butyldimethylsilyloxy-3-(2-chloropyridin-3-yl)propionate

A mixture of 5.6 g of ethyl 2-azido-3-t-butyldimethylsilyloxy-3-(2-chloropyridin-3-yl)propionate (prepared as described in Preparation 77), 7.5 g of triphenylphosphine and 18 ml of a 8:1 by volume mixture of tetrahydrofuran and water was stirred at room temperature for 3 hours. At the end of this time, the reaction mixture was freed from the solvent by distillation. The residue was purified by column chromatography through silica gel, using a 5:1 by volume mixture of hexane and ethyl acetate and subsequently a 50:1 by volume mixture of methylene chloride and methanol as the eluent, to give 5.9 g of the title compound having Rf=0.59 (on silica gel thin layer chromatography using a 15:1 by volume mixture of methylene chloride and methanol as the developing solvent).

PREPARATION 79

Ethyl 3-t-butyldimethylsilyloxy-3-(2-chloropyridin-3-yl)-2-methylaminopropionate 182 mg of 35% formalin, 0.1 ml of acetic acid and 121 mg of sodium cyanoborohydride were added to a solution of 0.7 g of ethyl 2-amino-3-t-butyldimethylsilyloxy-3-(2-chloropyridin-3-yl)propionate (prepared as described in Preparation 78) in 4 ml of a 3:2 by volume mixture of methylene chloride and water at 0° C., and the resulting mixture was stirred at 0° C. for 15 minutes. At the end of this time, a saturated aqueous solution of sodium hydrogencarbonate was added to the reaction mixture, after which it was extracted with ethyl acetate. The extract was washed with an aqueous solution of sodium chloride and dried over anhydrous sodium sulfate, after which the solvent was removed by distillation under reduced pressure. The residue was purified by column chromatography through silica gel, using a gradient elution method, with mixtures of hexane and ethyl acetate in ratios ranging from 8:1 to 1:1 by volume as the eluent, to give 200 mg of the title compound having Rf=0.38 (on silica gel thin layer chromatography using a 3:1 by volume mixture of hexane and ethyl acetate as the developing solvent).

PREPARATION 80

Ethyl 1-methyl-7-azaindole-2-carboxylate

A solution of 994 mg of ethyl 3-t-butyldimethylsilyloxy-3-(2-chloropyridin-3-yl)-2-methylaminopropionate (prepared as described in Preparation 79) and 393 mg of 1,5-diazabicyclo[4.3.0]non-5-ene in 5 ml of dimethylformamide was stirred at 150° C. for 5 hours. At the end of this time, the reaction mixture was poured into a saturated aqueous solution of ammonium chloride, after which it was extracted with ethyl acetate. The extract was washed with an aqueous solution of sodium chloride and dried over anhydrous sodium sulfate, after which the solvent was removed by distillation under reduced pressure. The residue was purified by column chromatography through silica gel, using a gradient elution method, with mixtures of hexane and ethyl acetate in ratios ranging from 9:1 to 5:1 by volume as the eluent, to give 150 mg of the title compound having Rf=0.40 (on silica gel thin layer chromatography using a 3:1 by volume mixture of hexane and ethyl acetate as the developing solvent).

PREPARATION 81

2-Hydroxymethyl-1-methyl-7-azaindole

A procedure similar to that described in Preparation 2 was repeated, except that 130 mg of ethyl 1-methyl-7-azaindole-2-carboxylate (prepared as described in Preparation 80), 23 mg of lithium aluminum hydride and 2 ml of tetrahydrofuran were used, to give 110 mg of the title compound having Rf=0.47 (on silica gel thin layer chromatography using a 3:1 by volume mixture of hexane and ethyl acetate as the developing solvent).

PREPARATION 82

5-[4-(1-Methyl-7-azaindol-2-ylmethoxy)benzyl]-3-triphenylmethylthiazolidine-2,4-dione A solution of 103 mg of 2-hydroxymethyl-1-methyl-7-azaindole (prepared as described in Preparation 81), 346 mg of 5-(4-hydroxybenzyl)-3-triphenylmethylthiazolidine-2,4-dione, 166 mg of diethyl azodicarboxylate and 250 mg of triphenylphosphine in 3 ml of tetrahydrofuran was stirred at room temperature for 15 hours. At the end of this time, the reaction mixture was freed from the solvent by distillation. The resulting residue was purified by column chromatography through silica gel, using a gradient elution method, with mixtures of hexane and ethyl acetate in ratios ranging from 5:1 to 4:1 by volume as the eluent, to give 277 mg of the title compound having Rf=0.41 (on silica gel thin layer chromatography using a 1:1 by volume mixture of hexane and ethyl acetate as the developing solvent).

PREPARATION 83

3-Nitro-2-phenylaminopyridine

A procedure similar to that described in Preparation 66 was repeated, except that 15 g of 2-chloro-3-nitropyridine, 13.22 g of aniline and 25.07 g of sodium carbonate were reacted in 180 ml of toluene. After working up the product as described in Preparation 66, the resulting crude product was purified by column chromatography through silica gel, using a 1:5 by volume mixture of ethyl acetate and hexane, to give 6.9 g of the title compound, melting at 66–68° C.

PREPARATION 84

3-Amino-2-phenylaminopyridine

A procedure similar to that described in Example 6 was repeated, except that 6.9 g of 3-nitro-2-phenylaminopyridine (prepared as described in Preparation 83) was hydrogenated in a mixture of 150 ml of ethanol and 50 ml of dioxane in the presence of 1.38 g of 10% w/w palladium-on-charcoal. After working up the product as described in Example 6, 4.2 g of the title compound, melting at 137–140° C., were obtained.

PREPARATION 85

2-Hydroxymethyl-5,7-dimethyl-3H-imidazo[5,4-b]pyridine

A mixture of 13.72 g of 2,3-diamino-4,6-dimethylpyridine and 25 g of glycolic acid in 200 ml of toluene was heated under reflux for 3.5 hours, whilst distilling off azeotropically the water formed in the course of the reaction. At the end of this time, the reaction mixture was freed from the toluene by decantation and the oily residue was purified by column chromatography through silica gel, using a gradient elution method, with mixtures of ethanol and ethyl acetate in ratios ranging from 2:3 to 1:1 by volume as a eluent, to give 2.7 g of the title compound, melting at 244–246° C.

PREPARATION 86

2-Hydroxymethyl-3,5,7-trimethylimidazo[5,4-b]pyridine

A procedure similar to that described in Preparation 15 was repeated, except that 2.6 g of 2-hydroxymethyl-5,7-dimethyl-3H-imidazo[5,4-b]pyridine (prepared as described in Preparation 85), 0.64 g of sodium hydride (as a 55% by weight dispersion in mineral oil), 2.2 g of iodomethane and 80 ml of dimethylformamide were used. After working up the product as described in Preparation 15, the resulting crude product was purified by column chromatography through silica gel, using a 1:6 by volume mixture of ethanol and ethyl acetate as the eluent, followed by recrystallization from ethyl acetate, to give 1.5 g of the title compound, melting at 178–179° C.

PREPARATICN 87

5-{4-(3,5,7-Trimethylimidazo[5,4-b]pyridin-2-ylmethoxy)benzyl}-3-triphenylmethylthiazolidine-2,4-dione A procedure similar to that described in Preparation 4 was repeated, except that 1.47 g of 2-hydroxymethyl-3,5,7-trimethylimidazo[5,4-b]pyridine (prepared as described in Preparation 86), 3.58 g of 5-(4-hydroxybenzyl)-3-triphenylmethylthiazolidine-2,4-dione, 1.87 g of tributylphosphine, 2.33 g of 1,1'-(azodicarbonyl)dipiperidine and 50 ml of toluene were used. After working up the product as described in Preparation 4, the resulting crude product was purified by column chromatography through silica gel, using a 1:1 by volume mixture of hexane and ethyl acetate as the eluent, to give 3.5 g of the title compound, melting at 96–99° C. (softening).

PREPARATION 88

2-Methylamino-3-nitro-6-phenylthiopyridine 3.6 ml of thiophenol were added dropwise to a suspension of 1.54 g of sodium hydride (as a 55% by weight dispersion in mineral oil, and which had previously been washed with hexane) in 30 ml of dimethylformamide, and the resulting mixture was stirred for 1 hour at room temperature. The mixture was then added dropwise to a solution of 6.00 g of 6-chloro-2-methylamino-3-nitropyridine (prepared as described in Preparation 66) in dimethylformamide, whilst cooling with ice, and then the mixture was stirred at 5° C. for 2 hours. At the end of this time, the reaction mixture was freed from the dimethylformamide by distillation under reduced pressure. The residue was mixed with water and the aqueous mixture was extracted with ethyl acetate. The extract was washed with an aqueous solution of sodium chloride and dried over anhydrous sodium sulfate, after which the solvent was removed by distillation under reduced pressure. The residue was purified by column chromatography through silica gel, using a 3:1 by volume mixture of hexane and ethyl acetate as the eluent, to give 8.40 g of the title compound having Rf=0.67 (on silica gel thin layer chromatography using a 3:1 by volume mixture of hexane and ethyl acetate as the developing solvent).

PREPARATION 89

3-Amino-2-methylamino-6-phenylthiopyridine

A procedure similar to that described in Example 6, was repeated, except that 5.40 g of 2-methylamino-3-nitro-6-phenylthiopyridine (prepared as described in Preparation 88) were hydrogenated in 80 ml of methanol in the presence of 1.10 g of 10% w/w palladium-on-charcoal. After working up the product as described in Example 6, 4.00 g of the title compound having Rf=0.69 (on silica gel thin layer chromatography using ethyl acetate as the developing solvent) were obtained.

PREPARATION 90

2-Hydroxymethyl-3-methyl-5-phenylthioimidazo[5,4-b]pyridine

A procedure similar to that described in Preparation 43 was repeated, except that 2.62. g of 3-amino-2-methylamino-6-phenylthiopyridine (prepared as described in Preparation 89) and 2.58 g of glycolic acid were used, and that the product was purified by column chromatography through silica gel, using a gradient elution method, with mixtures of ethyl acetate and methanol in ratios ranging from 50:1 to 10:1 by volume as the eluent, to give 1.80 g of the title compound, melting at 119–120° C.

PREPARATION 91

5-{4-(3-Methyl-5-phenylthioimidazo[5,4-b]pyridin-2-ylmethoxy)benzyl}-3-triphenylmethylthiazolidine-2,4-dione A procedure similar to that described in Preparation 4 was repeated, except that 0.70. g of 2-hydroxymethyl-3-methyl-5-phenylthioimidazo[5,4-b]pyridine (prepared as described in Preparation 90), 1.20 g of 5-(4-hydroxybenzyl)-3- triphenylmethylthiazolidine-2,4-dione, 0.64 ml of tributylphosphine, 0.65 g of 1,1'-(azodicarbonyl) dipiperidine and 25 ml of toluene were used, and that the product was purified by column chromatography through silica gel, using a 1:1 by volume mixture of hexane and ethyl acetate as the eluent, to give 1.61 g of the title compound, melting at 90–95° C. (softening).

PREPARATION 92

6-Benzyloxy-2-methylamino-3-nitropyridine

A procedure similar to that described in Preparation 88 was repeated, except that 7.00 g Of 6-chloro-2-methylamino-3-nitropyridine (prepared as described in Preparation 66), 1.79 g of sodium hydride (as a 55% by weight dispersion in mineral oil), 4.3 ml of benzyl alcohol and 150 ml of dimethylformamide were used. After working up the product as described in Preparation 88, the resulting crude product was crystallized by trituration with isopropanol, to give 9.02 g of the title compound, melting at 149° C.

PREPARATION 93

3-Amino-6-benzyloxy-2-methylaminopyridine 21.4 g of zinc were added to a solution of 8.50 of 6-benzyloxy-2-methylamino-3-nitropyridine (prepared as described in Preparation 92) in 360 ml of methanol, and then 8.5 ml of acetic acid were added dropwise. The resuluting mixture was then stirred at room temperature for one hour. At the end of this time, the reaction mixture was filtered to remove insoluble material. The filtrate was freed from the solvent by distillation under reduced pressure, and the resulting residue was dissolved in ethyl acetate. The solution was washed with an aqueous solution of sodium hydrogencarbonate and with a saturated aqueous solution of sodium chloride, in that order. The organic layer was dried over anhydrous sodium sulfate and the solvent was removed by distillation under reduced pressure, to give 7.50 g of the title compound having Rf=0.63 (on silica gel thin layer chromatography using ethyl acetate as the developing solvent).

PREPARATION 94

5-Benzyloxy-2-hydroxymethyl-3-methylimidaz[5,4-b]pyridine

A procedure similar to that described in Preparation 43 was repeated, except that 7.50 g of 3-amino-6-benzyloxy-2-methylaminopyridine (prepared as described in Preparation 93) and 7.46 g of glycolic acid were reacted. After working up the product as described in Preparation 43, the resulting crude product was purifying by column chromatography through silica gel, using a 10:1 by volume mixture of ethyl acetate and methanol as the eluent, and was then crystallized by trituration with ethyl acetate, to give 4.10 g of the title compound, melting at 133–135° C.

PREPARATION 95

5-{4-(5-Benzyloxy-3-methylimidazo[5,4-b]pyridin-2-ylmethoxy)benzyl}-3-triphenylmethylthiazolidine-2,4-dione A procedure similar to that described in Preparation 4 was repeated, except that 3.15 g of 5-benzyloxy-2-hydroxymethyl-3-methylimidazo[5,4-b]pyridine (prepared as described in Preparation 94), 5.50 g of 5-(4-hydroxybenzyl)-3-triphenylmethylthiozolidine-2,4-dione, 2.91 ml of tributylphosphine, 2.95 g of 1,1'-(azodicarbonyl) dipiperidine and 100 ml of toluene were used, and that the product was purified by column chromatography through silica gel, using a gradient elution method, with mixtures of hexane and ethyl acetate in ratios ranging from 1:1 to 1:2 by volume as the eluent, to give 7.10 g of the title compound, melting at 88–92° C. (softening).

PREPARATION 96

6-Ethoxy-2-methylamino-3-nitropyridine

A procedure similar to that described in Preparation 88 was repeated, except that 6.00 g of 6-chloro-2-methylamino-3-nitropyridine (prepared as described in Preparation 66), 1.54 g of sodium hydride (as a 55% by weight dispersion in mineral oil), 2.1 ml of ethanol and 150 ml of dimethylformamide were used. After working up the product as described in Preparation 88, the resulting crude product was crystallized by trituration with ethanol, to give 5.10 g of the title compound, melting at 101° C.

PREPARATION 97

3-Amino-6-ethoxy-2-methylaminopyridine

A procedure similar to that described in Example 6 was repeated, except that 4.95 g of 6-ethoxy-2-methylamino-3-nitropyridine (prepared as described in Preparation 96) were hydrogenated in 100 ml of 1,4-dioxane in the presence of 1.00 g of 10% w/w palladium-on-charcoal. After working up the product as described in Example 6, 4.20 g of the title compound having Rf=0.57(on silica gel thin layer chromatography using ethyl acetate as the developing solvent) were obtained.

PREPARATION 98

5-Ethoxy-2-hydroxymethyl-3-methylimidazo[5,4-b]pyridine

A procedure similar to that described in Preparation 43 was repeated, except that 4.15 g 3-amino-6-ethoxy-2-methylaminopyridine (prepared as described in Preparation 97), and 5.66 g of glycolic acid were used, and that the product was purified by column chromatography through silica gel, using a 10:1 by volume mixture of ethyl acetate and methanol as the eluent, to give 3.20 g of the title compound, melting at 161° C.

PREPARATION 99

5-{4-(5-Ethoxy-3-methylimidazo[5,4-b]pyridin-2-yl-methoxy)benzyl}-3-triphenylmethylthiazolidine-2,4-dione A procedure similar to that described in Preparation 4 was repeated, except that 1.00 g of 5-ethoxy-2-hydroxymethyl-3-methylimidazo[5,4-b]pyridine (prepared as described in Preparation 98), 2.25 g of 5-(4-hydroxybenzyl)-3-triphenylmethylthiozolidine-2,4-dione, 1.2 ml of tributylphosphine, 1.22 g of 1,1'-(azodicarbonyl) dipiperidine and 60 ml of toluene were used, and that the product was purified by column chromatography through silica gel, using a 1:1 by volume mixture of hexane and ethyl acetate as the eluent, to give 2.81 g of the title compound, melting at 88–100° C. (softening).

PREPARATION 100

6-Isopropoxy-2-methylamino-3-nitropyridine

A procedure similar to that described in Preparation 88 was repeated, except that 6.00 g of 6-chloro-2-methylamino- 3-nitropyridine (prepared as described in Preparation 66), 1.54 g of sodium hydride (as a 55% by weight dispersion in mineral oil), 2.7 ml of isopropanol and 150 ml of dimethylformamide were used. After working up the product as described in Preparation 88, the resulting crude product was crystallized by trituration with isopropanol, to give 6.10 g of the title compound, melting at 75–76° C.

PREPARATION 101

3-Amino-6-isopropoxy-2-methylaminopyridine

A procedure similar to that described in Example 6 was repeated, except that 2.38 g of 6-isopropoxy-2-methylamino-3-nitropyridine (prepared as described in Preparation 100) were hydrogenated in 50 ml of methanol in the presence of 0.50 g of 10% w/w palladium-on-charcoal. After working up the product as described in Example 6, 2.00 g of the title compound having Rf=0.62 (on silica gel thin layer chromatography using ethyl acetate as the developing solvent) were obtained.

PREPARATION 102

5-Isopropoxy-2-hydroxymethyl-3-methylimidazo[5,4-b]pyridine

A procedure similar to that described in Preparation 43 was repeated, except that 1.90 g of 3-amino-6 -isopropoxy-2-methylaminopyridine (prepared as described in Preparation 101), and 2.39 g of glycolic acid were used, and that the product was purified by column chromatography through silica gel, using a 10:1 by volume mixture of ethyl acetate and methanol, to give 0.58 g of the title compound, melting at 125–127° C.

PREPARATION 103

5-{4-(5-Isopropoxy-3-methylimidazo[5,4-b]pyridin-2-ylmethoxy)benzyl}-3-triphenylmethylthiazolidine-2,4-dione A procedure similar to that described in Preparation 4 was repeated, except that 0.33 g 5-isopropoxy-2-hydroxymethyl-3-methylimidazo[5,4-b]pyridine (prepared as described in Preparation 102), 0.69 g of 5-(4-hydroxybenzyl)-3-triphenylmethylthiazolidine-2,4-dione, 0.37 ml of tributylphosphine, 0.38 g of 1,1'-(azodicarbonyl) dipiperidine and 20 ml of toluene were used, and that the product was purified by column chromatography through silica gel, using a 1:1 by volume mixture of hexane and ethyl acetate as the eluent, to give 0.85 g of the title compound, melting at 90–100° C. (softening).

PREPARATION 104

2-Methylamino-3-nitropyridine

A procedure similar to that described in Preparation 66 was repeated, except that 24.9 g of 2-chloro-3-nitropyridine, 41.7 g of sodium carbonate, 22.7 ml of a 30% ethanolic solution of methylamine were reacted in 250 ml of toluene. After working up the product as described in Preparation 66, the resulting crude product was crystallized by trituration with isopropanol, to give 24.0 g of the title compound, melting at 52–53° C.

PREPARATION 105

3-Amino-2-methylaminopyridine

A procedure similar to that described in Example 6 was repeated, except that 5.00 g of 2-methylamino-3-nitropyridine (prepared as described in Preparation 104) were hydrogenated in 80 ml of 1,4-dioxane in the presence of 1.00 g of 10% w/w palladium-on-charcoal. After working up the product as described in Example 6, 3.87 g of the title compound, melting at 90–92° C. were obtained.

PREPARATION 106

5-{4-[2-(1,3-Dioxolan-2-yl)ethoxy]benzyl}-thiazolidine-2,4-dione

A procedure similar to that described in Preparation 46 was repeated, except that 15.0 g of 5-(4-hydroxybenzyl) thiazolidine-2,4-dione, 8.80 g of sodium hydride (as a 55% by weight dispersion in mineral oil), 17 ml of 2-(2-bromoethyl)-1,3-dioxolane and 80 ml of dimethylformamide were used, and that the product was purified by column chromatography through silica gel, using a 1:1 by volume mixture of hexane and ethyl acetate as the eluent, to give 6.67 g of the title compound, melting at 102–104° C.

PREPARATION 107

5-[4-(3-Oxopropoxy)benzyl]thiazolidine-2,4-dione

A solution of 6.30 g of 5-{4-[2-(1,3-dioxolan-2 -yl) ethoxy]benzyl}thiazolidine-2,4-dione (prepared as described in Preparation 106) in 50 ml of a 4:1 mixture of acetic acid and water was stirred at 60° C. for 6 hours. At the end of this time, the reaction mixture was freed from the solvent by distillation under reduced pressure. The resulting residue was purified by column chromatography through silica gel, using a 1:1 by volume mixture of hexane and ethyl acetate as the eluent, to give 2.20 g of the title compound, melting at 48–51° C.

PREPARATION 108

2-Methylamino-3-nitro-6-phenylpyridine 50 ml of a 2 N aqueous solution of sodium carbonate and 0.34 g of 20% w/w palladium hydroxide on charcoal were added to a solution of 5.0 g of 6-chloro-2-methylamino-3-nitropyridine (prepared as described in Preparation 66) and 3.9 g of phenyl borate in 80 ml of a 1:1 by volume mixture of ethanol and toluene, and the resulting mixture was stirred at 105° C. for 4.5 hours. At the end of this time, the reaction mixture was filtered to remove the palladium hydroxide on charcoal. The filtrate was concentrated by evaporation under reduced pressure, and the concentrate was diluted with water, after which it was extracted with ethyl acetate. The extract was washed with water and dried over anhydrous sodium sulfate, after which the solvent was removed by distillation under reduced pressure. The residue was crystallized by trituration with ethanol, to give 4.75 g of the title compound, melting at 98–99° C.

PREPARATION 109

3-Amino-2-methylamino-6-phenylpyridine

A procedure similar to that described in Example 6 was repeated, except that 5.7 g of 2-methylamino-3-nitro-6-phenylpyridine (prepared as described in Preparation 108) were hydrogenated in 200 ml of a 1:1 by volume mixture of ethanol and 1,4-dioxane in the presence of 1.14 g of 10% w/w palladium-on-charcoal. After working up the product as described in Example 6, 4.9 g of the title compound having Rf=0.08 (on silica gel thin layer chromatography using a 1:5 by volume mixture of ethyl acetate and hexane as the developing solvent) were obtained.

PREPARATION 110

2-Hydroxymethyl-3-methyl-5-phenylimidazo[5,4-b]pyridine

A procedure similar to that described in Preparation 43 was repeated, except that 4.9 g of 3-amino-2-methylamino-6-phenylpyridine (prepared as described in Preparation 109) and 5.6 g of glycolic acid were used, and that the product was purified by column chromatography through silica gel, using a gradient elution method, with mixtures of ethyl acetate and ethanol in ratios ranging from 1:0 to 10:1 by volume as the eluent, to give 0.9 g of the title compound, melting at 174–177° C.

PREPARATION 111

5-{4-(3-Methyl-5-henylimidazo[5,4-b]pyridin-2-ylmethoxy)benzyl}-3-triphenylmethylthiazolidine-2.4-dione A procedure similar to that described in Preparation 4 was repeated, except that 0.5 g of 2-hydroxymethyl-3-methyl-5-phenylimidazo[5,4-b]pyridine (prepared as described in Preparation 110), 0.97 g of 5-(4-hydroxybenzyl)-3-triphenylmethylthiazolidine-2,4-dione, 0.57 ml of tributylphosphine, 0.53 g of 1,1'-(azodicarbonyl)dipiperidine and 50 ml of benzene were used. After working up the product as described in Preparation 4, the resulting crude product was purified by column chromatography through silica gel, using a 1:1 by volume mixture of hexane and ethyl acetate as the eluent, to give 0.9 g of the title compound having Rf=0.26 (on silica gel thin layer chromatography using a 1:1 by volume mixture of ethyl acetate and hexane as the developing solvent).

PREPARATION 112

2-(4-Formylphenoxymethyl)-3-methylimidazo[5,4-b]pyridine

A procedure similar to that described in Preparation 4 was repeated, except that 500 mg of 3-methylimidazo[5,4-b]pyridin-2-ylmethanol (prepared as described in Preparation 15), 374 mg of 4-hydroxybenzaldehyde, 0.76 ml of tributylphosphine, 773 mg of 1,1'-(azodicarbonyl)dipiperidine and 12 ml of toluene were used, and that the product was purified by column chromatography through silica gel, using a gradient elution method, with mixtures of ethyl acetate and methanol in ratios ranging from 1:0 to 50:1 by volume as the eluent, to give 0.37 g of the title compound, melting at 124–125° C.

We claim:

1. A compound of formula (I):

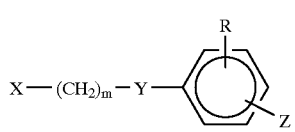

wherein:

X represents an azaindolyl, azaindolinyl, imidazopyridyl or imidazopyrimidinyl group which is unsubstituted or is substituted by at least one substituent selected from the group consisting of substituents α defined below;

Y represents an oxygen atom or a sulfur atom;

Z represents a group of formula, (iv) or (v):

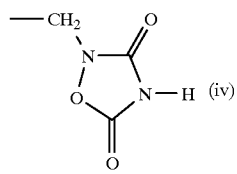 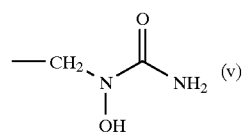

R represents a hydrogen atom, an alkyl group having from 1 to 4 carbon atoms, an alkoxy group having from 1 to 4 carbon atoms, a halogen atom, a hydroxy group, a nitro group, an aralkyl group in which an alkyl group having from 1 to 5 carbon atoms is substituted by an aryl group having from 6 to 10 ring carbon atoms, or a group of formula —NR$^a$R$^b$, wherein R$^a$ and R$^b$ are the same or different and each represents a hydrogen atom, an alkyl group having from 1 to 8 carbon atoms, an aralkyl group in which an alkyl group having from 1 to 5 carbon atoms is substituted by an aryl group having from 6 to 10 ring carbon atoms, an aryl group having from 6 to 10 ring carbon atoms, an aliphatic carboxylic acyl group having from 1 to 11 carbon atoms, an aliphatic carboxylic acyl group which has from 2 to 6 carbon atoms and which is substituted by an aryl group having from 6 to 10 ring carbon atoms, or an aromatic carboxylic acyl group in which the aryl part has from 6 to 10 ring carbon atoms, m is an integer of from 1 to 5;

each of said substituents α represents an alkyl group having from 1 to 4 carbon atoms, an aryl group having from 6 to 10 carbon atoms, a trifluoromethyl group, an alkylthio group having from 1 to 4 carbon atoms, an alkoxy group having from 1 to 4 carbon atoms, a benzyloxy group, a halogen atom, a hydroxy group, an acetoxy group, a phenylthio group, a nitro group, an aralkyl group, or a group of formula —NR$^a$R$^b$, wherein R$^a$ and R$^b$ are as defined above;

said aryl groups and the aryl parts of said aralkyl groups included in substituents α are carbocyclic aromatic groups having from 6 to 10 ring carbon atoms and are unsubstituted or are substituted at least one substituent selected from the group consisting of substituents β, defined below;

each of said substituents β represents an alkyl group having from 1 to 4 carbon atoms, an alkoxy group having from 1 to 4 carbon atoms, a halogen atom, a hydroxy group, a nitro group, a phenyl group, a trifluoromethyl group, or a group of formula —NR$^a$R$^b$, wherein R$^a$ and R$^b$ are as defined above;

and salts thereof.

2. The compound of claim 1, wherein X represents an azaindolyl, imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, provided that, if R$^a$ or R$^b$ represents an aryl group or represents a group including an aryl group, that aryl group is not itself further substituted by a group of formula —NR$^a$R$^b$;

or an aralkyl group having from 7 to 11 carbon atoms which is unsubstituted or is substituted by at least one substituent selected from the group consisting of substituents β.

3. The compound of claim 1, wherein X represents an imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by at least one substituent selected from the group consisting of substituents β.

4. The compound of claim 1, wherein X represents an imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by from 1 to 3 substituents selected from the group consisting of substituents β.

5. The compound of claim 1, wherein X represents an indolinyl or imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group or a phenyl group.

6. The compound of claim 1, wherein X represents an imidazopyridyl group, which is unsubstituted or is substituted by from 1 to 3 of substituents α, defined below;

substituent α represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group or a phenyl group.

7. The compound of claim 1, wherein R represents a hydrogen atom, an alkyl group having from 1 to 4 carbon atoms, an alkoxy group having from 1 to 4 carbon atoms or a halogen atom.

8. The compound of claim 1, wherein R represents a hydrogen atom, a methoxy group, an ethoxy group, a fluorine atom or a chlorine atom.

9. The compound of claim 1, wherein R represents a hydrogen atom or a methoxy group.

10. The compound of claim 1, wherein R represents a hydrogen atom.

11. The compound of claim 1, wherein Y represents an oxygen atom.

12. The compound of claim 1, wherein Z represents a 3,5-dioxooxadiazolidin-2-ylmethyl group.

13. The compound of claim 1, wherein Z represents a N-hydroxyureidomethyl group.

14. The compound of claim 1, wherein:

X represents azaindolyl, imidazopyridyl or imidazopyrimidinyl group, which is unsubstituted or is substituted by from 1 to 3 substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, provided that, if R$^a$ or R$^b$ represents an aryl group or represents a group including an aryl group, that aryl group is not itself further substituted by a group of formula —NR$^a$R$^b$;

or an aralkyl group having from 7 to 11 carbon atoms which is unsubstituted or is substituted by at least one substituent selected from the group consisting of substituents β;

Y represents an oxygen or sulfur atom;

Z represents a 3,5-dioxooxadiazolidin-2-ylmethyl or N-hydroxyureidomethyl group;

R represents a hydrogen atom, an alkyl group having from 1 to 4 carbon atoms, an alkoxy group having from 1 to 4 carbon atoms or a halogen atom;

m is an integer of from 1 to 5.

15. The compound of claim 1, wherein:

X represents an imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by at least one substituent selected from the group consisting of substituents β;

Y represents an oxygen atom;

R represents a hydrogen atom, an alkyl group having from 1 to 4 carbon atoms, an alkoxy group having from 1 to 4 carbon atoms or a halogen atom; and m is an integer of from 1 to 5.

16. The compound of claim 1, wherein:

X represents an imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by from 1 to 3 substituents selected from the group consisting of substituents β;

Y represents an oxygen atom;

R represents a hydrogen atom, a methoxy group, an ethoxy group, a fluorine atom or a chlorine atom; and m is an integer of from 1 to 5.

17. The compound of claim 1, wherein:

X represents an imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group or a phenyl group;

Y represents an oxygen atom;

R represents a hydrogen atom or a methoxy group; and m is an integer of from 1 to 5.

18. The compound of claim 1, wherein:

X represents an imidazopyridyl group, which is unsubstituted or is substituted by from 1 to 3 of substituents α, defined below;

substituent α represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group or a phenyl group;

Y represents an oxygen atom;

R represents a hydrogen atom; and m is an integer of from 1 to 5.

19. A pharmaceutical composition for the treatment or prophylaxis of diabetes or hyperlipemia and complications thereof, which composition comprises an effective amount of an active compound in admixture with a pharmaceutically acceptable carrier or diluent, wherein said active compound is selected from the group consisting of compounds of formula (I) and salts thereof, as claimed in claim 1.

20. The composition of claim 19, wherein:

X represents an azaindolyl, imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, provided that, if $R^a$ or $R^b$ represents an aryl group or represents a group including an aryl group, that aryl group is not itself further substituted by a group of formula —$NR^aR^b$;

or an aralkyl group having from 7 to 11 carbon atoms which is unsubstituted or is substituted by at least one substituent selected from the group consisting of substituents β;

Y represents an oxygen or sulfur atom;

Z represents a 3,5-dioxooxadiazolidin-2-ylmethyl or N-hydroxyureidomethyl group;

R represents a hydrogen atom, an alkyl group having from 1 to 4 carbon atoms, an alkoxy group having from 1 to 4 carbon atoms or a halogen atom;

m is an integer of from 1 to 5.

21. The composition of claim 19, wherein:

X represents an imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, or an aralkyl group having from 7 to 11 carbon atoms which is unsubstituted or is substituted by at least one substituent selected from the group consisting of substituents β;

Y represents an oxygen atom;

R represents a hydrogen atom, an alkyl group having from 1 to 4 carbon atoms, an alkoxy group having from 1 to 4 carbon atoms or a halogen atom; and m is an integer of from 1 to 5.

22. The composition of claim 19, wherein:

X represents an imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, or an aralkyl group having from 7 to 11 carbon atoms which is unsubstituted or is substituted by from 1 to 3 substituents selected from the group consisting of substituents β;

Y represents an oxygen atom;

R represents a hydrogen atom, a methoxy group, an ethoxy group, a fluorine atom or a chlorine atom; and m is an integer of from 1 to 5.

23. The composition of claim 19, wherein:

X represents an imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group or a phenyl group;

Y represents an oxygen atom;

R represents a hydrogen atom or a methoxy group; and m is an integer of from 1 to 5.

24. The composition of claim 19, wherein:

X represents an imidazopyridyl group, which is unsubstituted or is substituted by from 1 to 3 of substituents α, defined below;

substituent α represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group or a phenyl group;

Y represents an oxygen atom;

R represents a hydrogen atom; and m is an integer of from 1 to 5.

25. A method for the treatment or prophylaxis of diabetes or hyperlipemia and complications thereof in a mammal, which may be human, which method comprises administering to said mammal an effective amount of an active compound, wherein said active compound is selected from the group consisting of compounds of formula (I) and salts thereof, as claimed in claim 1.

26. The method of claim 25, wherein:

X represents an azaindolyl, imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, provided that, if $R^a$ or $R^b$ represents an aryl group or represents a group including an aryl group, that aryl group is not itself further substituted by a group of formula —$NR^aR^b$;

or an aralkyl group having from 7 to 11 carbon atoms which is unsubstituted or is substituted by at least one substituent selected from the group consisting of substituents β;

Y represents an oxygen or sulfur atom;

Z represents a 3,5-dioxcoxadiazolidin-2-ylmethyl or N-hydroxyureidomethyl group;

R represents a hydrogen atom, an alkyl group having from 1 to 4 carbon atoms, an alkoxy group having from 1 to 4 carbon atoms or a halogen atom;

m is an integer of from 1 to 5.

27. The method of claim 25, wherein:

X represents an imidazopyridyl or imidazopyrimidinyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, or an aralkyl group having from 7 to 11 carbon atoms which is unsubstituted or is substituted by at least one substituent selected from the group consisting of substituents β;

Y represents an oxygen atom;

R represents a hydrogen atom, an alkyl group having from 1 to 4 carbon atoms, an alkoxy group having from 1 to 4 carbon atoms or a halogen atom; and m is an integer of from 1 to 5.

28. The method of claim 25, wherein:

X represents an imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aromatic-substituted alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by from 1 to 3 substituents selected from the group consisting of substituents β;

Y represents an oxygen atom;

R represents a hydrogen atom, a methoxy group, an ethoxy group, a fluorine atom or a chlorine atom; and m is an integer of from 1 to 5.

29. The method of claim 25, wherein:

X represents an imidazopyridyl group, which is unsubstituted or is substituted by from 1 to 3 of substituents α, defined below;

substituent α represents an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group or a phenyl group;

Y represents an oxygen atom;

Z represents a 2,4-dioxothiazolidin-5-ylmethyl group;

R represents a hydrogen atom or a methoxy group; and m is an integer of from 1 to 5.

30. The method of claim 25, wherein:

X represents an imidazopyridyl group, which is unsubstituted or is substituted by from 1 to 3 of substituents α, defined below;

substituent α represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group or a phenyl group;

Y represents an oxygen atom;

R represents a hydrogen atom; and m is an integer of from 1 to 5.

* * * * *

UNITED STATES PATENT AND TRADEMARK OFFICE
CERTIFICATE OF CORRECTION

PATENT NO.     : 5,962,470
DATED          : October 5, 1999
INVENTOR(S)    : Fujita et al.

It is certified that error appears in the above-identified patent and that said Letters Patent is hereby corrected as shown below:

Column 77,
Cpd. No. 2-6, in the structural formula delete "H" and insert -- Me --.
Cpd. No. 2-8, in the structural formula delete "Me" and insert -- Et --.

Column 167,
Cpd. No. 5-103, under the column heading "m", delete "3" and insert -- 2 --.

Column 226,
Line 32, (claim 1), delete "a" and insert -- α --.

Column 228,
Line 25, (claim 5), delete "indolinyl or".

Column 236,
Line 13, (claim 29), delete "Z represents a 2, 4-dioxothiazolidin-5-ylmethyl group;".

Signed and Sealed this

Eighteenth Day of September, 2001

*Attest:*

NICHOLAS P. GODICI
*Attesting Officer*    *Acting Director of the United States Patent and Trademark Office*